United States Patent
Popp et al.

(10) Patent No.: US 11,717,498 B2
(45) Date of Patent: *Aug. 8, 2023

(54) METHODS OF TREATMENT USING AMPHETAMINE CONTROLLED RELEASE, PRODRUG, AND ABUSE DETERRENT DOSAGE FORMS

(71) Applicant: CHEMAPOTHECA, LLC, Delmar, NY (US)

(72) Inventors: Karl Popp, Schodack Landing, NY (US); Harold Meckler, Delmar, NY (US)

(73) Assignees: Pharmapotheca A, Inc., Delmar, NY (US); Chemapotheca, LLC, Delmar, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/066,488

(22) Filed: Oct. 9, 2020

(65) Prior Publication Data

US 2021/0030699 A1 Feb. 4, 2021

Related U.S. Application Data

(60) Continuation of application No. 16/941,534, filed on Jul. 29, 2020, now abandoned, and a continuation of application No. PCT/US2017/019285, filed on Feb. 24, 2017, and a continuation of application No. 15/441,424, filed on Feb. 24, 2017, now Pat. No. 11,123,310, which is a continuation-in-part of application No. 15/062,872, filed on Mar. 7, 2016, now Pat. No. 9,657,041, which is a division of application No. 14/189,630, filed on Feb. 25, 2014, now Pat. No. 9,278,904.

(60) Provisional application No. 62/299,108, filed on Feb. 24, 2016, provisional application No. 61/922,729, filed on Dec. 31, 2013.

(51) Int. Cl.
| | | |
|---|---|---|
| A61K 31/137 | (2006.01) | |
| A61K 47/64 | (2017.01) | |
| A61K 9/50 | (2006.01) | |
| A61K 47/54 | (2017.01) | |
| A61K 9/20 | (2006.01) | |
| A61K 9/28 | (2006.01) | |

(52) U.S. Cl.
CPC .......... *A61K 31/137* (2013.01); *A61K 9/2031* (2013.01); *A61K 9/2866* (2013.01); *A61K 9/5026* (2013.01); *A61K 9/5047* (2013.01); *A61K 47/542* (2017.08); *A61K 47/64* (2017.08)

(58) Field of Classification Search
CPC .... A61K 31/137; A61K 47/542; A61K 47/64; A61K 9/2031; A61K 9/2866; A61K 9/5026; A61K 9/5047

See application file for complete search history.

(56) References Cited

U.S. PATENT DOCUMENTS

| | | |
|---|---|---|
| 6,384,020 B1 | 5/2002 | Flanner |
| 6,399,828 B1 | 6/2002 | Boswell |
| 7,105,486 B2 | 9/2006 | Mickle |
| 7,655,630 B2 | 2/2010 | Mickle |
| 7,659,253 B2 | 2/2010 | Mickle |
| 7,662,787 B2 | 2/2010 | Mickle |
| 7,705,184 B2 | 4/2010 | Buenger |
| 8,487,134 B2 | 7/2013 | Meudt |
| 9,278,904 B2 | 3/2016 | Meckler |
| 9,321,794 B2 | 4/2016 | Meckler |
| 9,657,041 B2 | 5/2017 | Meckler |
| 10,087,202 B2 | 10/2018 | Meckler |
| 11,123,310 B2 * | 9/2021 | Popp .................... A61K 9/5026 |
| 2011/0159100 A1 | 6/2011 | Anderson |
| 2015/0183716 A1 | 7/2015 | Meckler et al. |

FOREIGN PATENT DOCUMENTS

| | | |
|---|---|---|
| FR | 59265 | 4/1969 |
| WO | WO 2007/054105 | 5/2007 |
| WO | WO 2011/084098 | 7/2011 |
| WO | WO 2015/130660 | 6/2015 |
| WO | WO 2015/130661 | 6/2015 |
| WO | WO2017147375 | 7/2017 |
| WO | WO 2020/180825 | 3/2020 |
| WO | WO 2020/180825 | 10/2020 |
| WO | WO 2020/180825 | 8/2021 |

OTHER PUBLICATIONS

Aziridine_phosphoramidate_-_Google_Scholar.pdf (Year: 2022).*
Fact Sheet for Dextroamphetamine from PubChem, from http pubchem,ncbi,nlm,nih,gov pp. 1-14, 2018.
Kojima, Scifinder Cas Registry 1485-13-8 for 2-methyl-3-phenyl-aziridine, Kojima 1959 et al, 1959.
Allen and Ely, Synthetic Methods for Amphetamines, Crime Scene magazine, p. 15-25 Spring 2011, 2011.
Zwierzak, A,; Brylikowska-Piotrowicz, J.; "Alkylation of Diethyl Phosphoramidates—A Simple Route from Primary Amines to Secondary Amines" *Angew. Chem. Int. Ed. Engl.* 1977, 16, 107, 1977.
Mekenyan, Scifinder 2010:1165579 ACS, Aziridine Use of Genotoxicity Information . . . , Chem Res Tox vol. 23 Issue 10 pp. 1519-1540, 2010, 2010.

(Continued)

*Primary Examiner* — Michael P Cohen
(74) *Attorney, Agent, or Firm* — Juneau & Mitchell; Todd L. Juneau

(57) ABSTRACT

The invention also relates to pharmaceutical compositions comprising highly pure amphetamine and amphetamine-class compounds resulting from the synthesis of chiral and racemic amphetamine derivatives by stereospecific, regioselective cuprate addition reaction with aziridine phosphoramidate compounds, and to methods of manufacturing, delivering, and using the amphetamine compounds resulting from the synthesis of chiral and racemic amphetamine derivatives by stereospecific, regioselective cuprate addition reaction with aziridine phosphoramidate compounds.

32 Claims, No Drawings

(56) References Cited

OTHER PUBLICATIONS

Sakurai, Scifinder 2000-630740 ACS, Aziridine Recommendation of Occupational exposure limits, J Occup Health, vol. 42, Issue 4, pp. 213-228, 2000, 2000.
Koleva, Scifinder 2011-1058228 ACS, Modelling of Acute Oral . . . aziridine toxicity, Toxicology InVitro, vol. 25, Issue 7, pp. 1281-1293, 2011, 2011.
Lambrechts, Leuckart-specific impurities in amphetamine, Bulletin on Narcotics, UNODC Everywhere, pp. 47-57, Jan. 1, 1984, 1984.
D'Ambra, Scifinder Search Results for D'Ambra patents (allergy drugs, regioselectivity) Accession 2002-52000, from US20020007068, 1999, 1999.
Rege et al. Drug Metabolism and Disposition, vol. 30 No. 12, pp. 1337-1343, Irreversible Inhibition of CYPD by (−) Chloroephedrine (impurity), 2002, 2002.
EMEA Committee for Medical Products, Grignard Solvents Committee, Feb. 10, 2005, pp. 1-7, 2005.
FDA CDER Guidance for Industry, (genotox guidance) Dec. 2008, 2008.
Skinner, Methamphetamine Synthesis via Hydriodic . . . , Forensic Sci Int'l, 48 (1990) 123-134, red phos method, 1990.
Anderson, Development of a Harmonized Method for Profiling . . . , Forensic Sci Int'l 169 (2007) pp. 50-63, GC method, 2007.
Anderson, Development of a Harmonized Method for Profiling . . . , Forensic Sci Int'l 169 (2007) pp. 64-76, GC method, 2007.
Stojanovska, A Review of Impurity Profiling . . . , Forensic Sci Int'l 224 (2013) 8-26, 2013.
Power, An Unusual Presentation of Customs Seizure, Forensic Sci Int'l 234 (2014) e10-e13, 2014.
Barker, A Study of the Use of Ephedra, Forensic Sci Int'l 166 (2007) 102-109, 2007.
Humphrey, Keeping Afloat in a Sea of Impurities, Global Safety Assessment, Astra Zeneca Jul. 6, 2007, 2007.
EMEA Solvent (Grignard) impurities, ICH Topic Q3C (R4), pp. 1-22, 2010, 2010.
Funel and Abele, Diels Alder Reactions Part 1, Angewandte Reviews, Angew. Chem Int 2013 vol. 52, 1-44, 2013, 2013.
Funel and Abele, Diels Alder Reactions Part 3, Angewandte Reviews, Angew. Chem Int 2013 vol. 52, 1-44, 2013, 2013.
Funel and Abele, Diels Alder Reactions Part 2, Angewandte Reviews, Angew. Chem Int 2013 vol. 52, 1-44, 2013, 2013.
Funel and Abele, Diels Alder Reactions Part 4, Angewandte Reviews, Angew. Chem Int 2013 vol. 52, 1-44, 2013, 2013.
Stephans, Substituted Aziridines, Prep and Properties, J Chem Engin, vol. 8, No. 4, pp. 625-626, Oct. 1963, 1963.
Stephans, Relative rates of Reaction and Direction of Ring Opening, J Chem Engin, vol. 14, No. 1, pp. 114-115, Jan. 1969, 1969.
Borkovec, Insect Chemosterilants, Aziridnylphosphine Oxides, JMedChem vol. 9, pp. 522-526, Feb. 1966, 1966.
Hata, Fragmentation Reaction of Ylide, JACS vol. 98-19, pp. 6033-6036, Sep. 1976, 1976.
Poshkus, the Reaction of Neutral Esters of Trivalent Phosphorus Acids, JACS vol. 79, pp. 6127-6129, 1957, 1957.
Jessing, Aziridines in Synthesis, Baran Lab Jan. 2007, 2007.
Hassner, A.; Galle, J. E.; "Ring Opening of Aziridine Phosphonates. Correlation of Structure, Nuclear Magnetic Resonance Spectra and Reactivity" J. Org. Chem., 1976, 41, 2273-2276, 1976.
Stromberg, Comparative GC Analysis, J Chromatography 106 (1975) 335-342, amphet sulfate, 1975.
Lambrechts, Profiling of Impurities in Illicit Amphetamine, 1986 J Chromatography vol. 369 (1976) pp. 365-377 HPLC impurities, 1986.
Allen, Methamphetamines from Ephedrine, J Forensic Sci vol. 32, No. 4, Jul. 1987, pp. 953-962, 1987.
Milstein, Friedel Crafts Reactions of Htree Member Heterocycles, J Het Chem vol. 5, pp. 339-241, Mar. 1968, 1968.
Hassner, Regiospecificity: A Useful Terminology, JOC vol. 33, No. 7 pp. 2684-2686 Jul. 1968, 1968.
Todd, Aneurin, A Synthesis of Thiochrome, J Chem Soc 1936, pp. 1601-1605, 1936.
Hider, Prep of Evidence in Amphet Prosecutions, J Forensic Sci pp. 75-79 1960's, 1960.
Anandasankar, Scifinder 7763-71-5, referring to WO 2011 130726, priority to US 2011-32804, and 2010-61325236, 2011.
Osowska-Pacewicka, N-Phosphorylated Aziridines—new reagents for electrophilic amination, Polish J Chem 68-6 pp. 1263-1264 1994, 1994.
Pramanik, An Efficient Scalable Process for Benzphetamine HCI, JACS J Org Process Res Dev 2014 vol. 18 pp. 495-500, 2014.
Giles, A Improved Process for the N-Alkylation of Indoles Using Chiral N-Protected 2-Mehtylaziridines J. Org Proc Res Dev, 2003 vol. 7, pp. 22-24.
Snodin, Potentially Mutagenic Impurities, J Org Process Res Dev 2014, vol. 18, pp. 836-839 Racemic, 2014.
Raman, Regulatory Expectations Towards Genotoxic, J Org Process Res Dev 2014 vol. 18 pp. 834-835, 2014.
Teasdale, Regulatory Highlights, J Org Process Res Dev 2014 vol. 18, 458-472, 2014.
Jawahar, Direct Stereospecific Synthesis of Unprotected N-H and N-Me Aziridines from Olefins, Sciences 343, 61 pp. 61-65, 2014, 2014.
Koziara, A.; Oleiniczak, B.; Osowska, K.; Zwierzak, A."Phosphoramidomercuration-Demercuration: A Simple Two-Step Conversion of Alkenes into Alkanamines" Synthesis 1982, 918-920, 1982.
Osowska-Pacewicka, Reactions of N-Phosphorylated Aziridines with Dianions Derived from Ethyl Aceotacetate and 1,3 Diketones, Synth. Common. Org. Chem. vol. 28:7, 1127-1137 1998, 1998.
Gajda, Synthesis of Primary sec-Alkylamines via Nucleophilic Ring-opening of N-Phosphorylated Aziridines, Tetrahedron Letters, 53:13, 4935-4946 1997, 1997.
Breque, A.; Savignac P.; "Derives Phosphoryles des Methyl-1 et Methyl-2 Amino-2 Ethanethiols" Phosphorus and Sulfur. 1980, 89-94.
US Pharmacopeia; "Dextroamphetamine Sulfate Tablets" Official Monographs. 2014, 2570-2571, 2014.
Herbrink, M.; Thijssen, B.; Hillebrand, M.J.X.; Rosing, H.; Schellen, J.H.M.; Nuijen, B.; Beijnen, J.H.; "Development and validation of a high-performance liquid chromatography-tandem mass spectrometry assay for the quantification of Dexamphetamine in human plasma" Journal of Pharmaceutical and Biomedical Analysis. 2018. 259-264, 2018.

* cited by examiner

METHODS OF TREATMENT USING AMPHETAMINE CONTROLLED RELEASE, PRODRUG, AND ABUSE DETERRENT DOSAGE FORMS

CROSS-REFERENCE TO RELATED APPLICATIONS

Provided by ADS.

BACKGROUND OF THE INVENTION

Field of Invention

The invention relates to pharmaceutical compounds, more particularly to the formulation and use thereof of compositions resulting from the synthesis of chiral and racemic amphetamine derivatives by stereospecific, regioselective cuprate addition reaction with aziridine phosphoramidate compounds, including, but not limited to traditional immediate, sustained and controlled release, as well as abuse deterrent and prodrug compositions.

Background

The background of synthesis and use of amphetamine compositions has been well documented in the published and patent literature. The initial synthesis of amphetamine was described by Edeleano in the late 1880's. [Ber. 20,616 (1887)]—[source Merck Index]. Synthesis routes have been described in patents, such as U.S. Pat. No. 1,921,424, and in the literature, such as the Journal of the American Chemical Society. [Hartung, W. H and Munch, J. C., J. Amer. Chem. Soc. 53,1875 (1931)].

Synthetic Pathways

Amphetamine-type substances (ATS), like other synthetically derived compounds, can be produced by a multitude of synthetic pathways using a variety of precursors and reagents, resulting in a large number of possible contaminants (by-products, intermediates and impurities). Review articles describe the common contaminants found in preparations of methylamphetamine (MA), 3,4-methylenedioxymethylamphetamine (MDMA), amphetamine (AP), N,N-dimethylamphetamine (DMA) and p-methoxyamphetamine (PMA) synthesized via common synthetic pathways including reductive amination, Leuckart method, Nagai method, Emde method, Birch reduction, "Moscow" method, Wacker process, "Nitrostyrene" method and the Peracid oxidation method. Contaminants can facilitate identification of the synthetic route, origin of precursors and may suggest information as to the location of manufacture of these illicit drugs [*Forensic Sci Int*. 2013 Jan. 10; 224(1-3):8-26. doi: 10.1016/j.forsciint.2012.10.040. Epub 2012 Nov. 24].

Prior Formulations

Formulation compositions of amphetamine type substances have also been well described in the published art. The US Food and Drug Administration Orange Book, for example, cites a number of patents pertaining to compositions that are encompassed in approved drug applications with the earliest being approved prior to Jan. 1, 1982 and the most recent on Oct. 15, 2015.

Since amphetamines are known to stimulate the central nervous system (CNS), they have been used medicinally to treat various disorders including attention deficit hyperactivity disorder (ADHD), obesity, and narcolepsy. In children with ADHD, potent CNS stimulants have been used for several decades as a drug treatment given either alone or as an adjunct to behavioral therapy. While methylphenidate (Ritalin®) has been the most frequently prescribed stimulant, the prototype of the class, amphetamine (alpha-methyl phenethylamine) has been used all along and increasingly so in recent years. (Bradley C, Bowen M, "Amphetamine (benzedrine) therapy of children's behavior disorders." American Journal of Orthopsychiatry 11: 92-103 (1941). [Reference U.S. Pat. No. 7,723,305]

Amphetamine type substances are also used as components of prodrugs. One such example is lisdexamfetamine dimesylate.

An alternate synthesis method for amphetamine type substances was developed by Meckler et al. [Reference: US Application 20150183716 and US Application 20150183810.]

Amphetamine Stereochemistry

The commercial importance of amphetamine derivatives has led to the development of numerous synthetic methods for their synthesis and their derivatization. One problem with amphetamine synthesis is the undesired production of toxic aziridine derivatives. Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes (+) and (−) or d and l are employed to designate the sign of rotation of plane-polarized light by the compound, with (−) and l meaning that the compound is levorotatory. A compound prefixed with (+) and d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture. Stereochemical purity is of importance in the field of pharmaceuticals, where 12 of the 20 most prescribed drugs are optically active. One example is the l-form of propranolol, which is about 100 times more potent than the d-form. Optical purity is important since certain isomers may be deleterious rather than simply inert. Another example is d-thalidomide that appears to be a safe and effective sedative for controlling morning sickness during pregnancy; whereas, l-thalidomide is thought to be a potent teratogen. Amphetamine and derivatives have been marketed as racemic mixtures comprising optical isomers, especially since in some derivatives there are two chiral centers. Previous studies aimed at investigating the pharmacology of these isomers have found significant differences in potency or efficacy on the one hand, and toxicity on the other hand.

Commercial production of 2-methyl-3-phenyl-aziridine produces isomeric forms, including R—R—, S—S—, and R—S— forms. However, only the R—S— of these is the desired active, the others being undesired impurities. Amphetamine production may also include other undesired impurities. These undesired aziridine impurities are considered mutagenic, and while healthy adult populations of patients may tolerate such impurities within the therapeutic compounds being administered, many patient populations such as pediatric patients cannot be exposed to such impurities. Accordingly, there is a need for dosage forms for amphetamine-related compounds having a statistically significant absence of such impurities.

Another problem with amphetamine synthesis is that amphetamines have a stereo-defined amine center, which can be subject to racemization. Accordingly, only stereospecific methods are useful. However, stereospecific methods do not provide the economic requirements of high yields, high selectivity and low process costs. Typically such reactions involve a coupling agent, such as Grignard or organolithium reagents. Conventional teaching requires that the use such organometallics requires that the reaction temperature be maintained at a cold temperature, such as an ice bath at less than 10 degrees Celsius.

To complicate the amphetamine marketplace, there are established formulations which require racemic amphetamine to obtain an extended release of elevated blood levels of the drug. This racemic material can be obtained by mixing equal parts of the dextrorotary and levorotary stereos isomers or running a synthetic sequence which only produces racemic amphetamine.

Toxicity and Synthetic Issues

Another problem with amphetamine synthesis is that the intermediates are toxic as well as flammable. This requires special handling such as double-walled drums and safety accommodations to protect manufacturing personnel.

The prior art in U.S. Pat. No. 6,399,828 teaches the production of amphetamine using various methods. In one approach norephedrine is refluxed with hydrogen iodide and red phosphorous. In another approach norephedrine is chlorinated using thionyl chloride and then catalytically hydrogenated. In U.S. Pat. No. 7,705,184, amphetamine synthesis is disclosed using hydrogenation of a chlorinated phenyl-propanolamine. Aziridine chemistry, and specifically aziridine phosphoramidates are not taught in the amphetamine synthesis prior art.

Zwierzak et al. disclose a method of reacting N-phosphorylated aziridines with copper-modified Grignard reagents as a new route to substituted pyrrolines and pyrrolidines. However, Zwierzak et al discloses this method as being regiospecific, which it is not. Int'l J. for Rapid Commun. of Syn. Org. Chem., 28:7, 1127-1137 (1998). Accordingly, where the prior art contained an erroneous teaching, it was surprising to discover otherwise.

Additionally, the use of protecting groups and leaving groups is well known. However, it has been discovered that there is significant variation among the various protecting groups. Specifically, where a carbonyl is used as a protecting group, the reaction must be kept at below -10 degrees Celsius or the carbonyl will react with the Grignard reagent. Where a sulfonyl is used as a protecting group, it is impossible to remove the protecting group without destroying the molecule.

Accordingly, there is a need for controlled release, prodrug, and abuse-deterrent pharmaceutical dosage forms that are manufactured from highly pure amphetamine and its derivatives which are made using synthetic processes which have high chemical yield, high selectivity, low cost, lower toxicity, have less impurities, and are less dangerous to handle.

BRIEF SUMMARY OF THE INVENTION

The present invention addresses one or more of the shortcomings of the prior art by providing a controlled release, prodrug, and abuse-deterrent pharmaceutical composition comprising highly pure amphetamine and/or amphetamine-class compounds resulting from the synthesis of chiral and racemic amphetamine derivatives by cuprate addition reaction with aziridine phosphoramidate compounds, and to methods of manufacturing, delivering, and using the amphetamine compounds.

In another preferred embodiment, the invention provides a controlled release, prodrug, and abuse-deterrent pharmaceutical composition comprising a substituted amphetamine or a pharmaceutically acceptable salt, solvate, prodrug, or mixture of two or more thereof, as the active pharmaceutical ingredient, and not more than 0.1% by weight of amphetamine-process related impurity, wherein the substituted amphetamine is produced by a process that comprises the steps of performing a stereospecific cuprate addition reaction upon an aziridine phosphoramidate compound to obtain a chiral aryl or aryl-alkyl phosphoramidate amphetamine precursor, and deprotecting the chiral aryl or aryl-alkyl phosphoramidate amphetamine precursor under acidic conditions effective to produce a substituted amphetamine.

In another aspect, the invention provides wherein the amphetamine-process related impurity is 2-methyl-3-phenyl-aziridine.

METHODS OF USE

In a preferred embodiment, the invention also comprises a method of treating a disorder which comprises administering to a patient in need thereof an effective amount of the pharmaceutical composition which comprises a drug product prepared by the process of synthesis of an amphetamine derivative comprising the step of performing a organo cuprate addition reaction upon an aziridine phosphoramidate compound to obtain an aryl or aryl-alkyl phosphoramidate amphetamine precursor and deprotecting under acidic conditions to obtain an amphetamine product having a regioisomeric purity >98%. In additional embodiments >99%.

In another preferred embodiment, the invention comprises wherein the organo cuprate addition reaction is stereospecific cuprate addition reaction upon an aziridine phosphoramidate compound to obtain a chiral aryl or aryl-alkyl phosphoramidate amphetamine precursor and deprotecting under acidic conditions to obtain a chiral amphetamine product having a regioisomeric purity >98%. In additional embodiments >99%.

The phrases an "effective amount" or a "therapeutically effective amount" of an active agent or ingredient, or pharmaceutically active agent or ingredient, which are synonymous herein, refer to an amount of the pharmaceutically active agent sufficient enough to have a positive effect on the patient. Accordingly, these amounts are sufficient to modify the disorder, condition, or appearance to be treated but low enough to avoid serious side effects, within the scope of sound medical advice.

A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

In a preferred embodiment, the invention comprises wherein the patient is a mammal, especially where in the mammal is between the ages of about 2 and 75 years of age, preferably between about 4 and 60. In another embodiment, the composition of the present invention is administered to a patient as a component of a therapeutic treatment regimen along with at least one additional therapeutic agent.

In a preferred embodiment, the invention comprises wherein the disorder is selected from the group consisting of diseases involving behavior, metabolism, drug absorption, drug excretion, and drug distribution in the body.

In a preferred embodiment, the invention comprises wherein said administering of said pharmaceutical composition results in an improvement of patient's condition, a change in behavior, reduction of symptoms, an improvement in patient's appearance, or a combination thereof.

In a preferred embodiment, the invention comprises wherein the disorder is selected from the group consisting of attention deficit hyperactivity disorder (ADHD), binge eating disorder, diet control, obesity and narcolepsy.

In a preferred embodiment, the invention comprises wherein said improvement of patient's condition, a change in behavior, reduction of symptoms, an improvement in patient's appearance, or a combination thereof can be measured.

In a preferred embodiment, the invention comprises wherein the symptoms improved are selected from the group consisting of inattentiveness, hyperactivity, and impulsivity, wherein Inattention is defined as comprising one or more of the following signs: Failure to pay attention to details or making careless mistakes; Unable to keep attention on tasks; Difficulty listening when spoken to directly; Inability to finish tasks or follow instructions; Trouble organizing activities; Avoidance of things that require long periods of mental effort; Losing things you need; Being easily distracted; Forgetting things in daily activities; and wherein Hyperactivity is defined as comprising one or more of the following signs: Fidgeting with hands and feet; Difficulty with quiet leisure activities; Unable to remain seated when it is expected; Feeling restless; Talking excessively; and wherein Impulsivity is defined as comprising one or more of the following signs: Blurting out answers before the question is finished; Unable to wait your turn; Interrupting other people's conversations.

In a preferred embodiment, the method comprises wherein the amphetamine employed is at least about 85% pure.

In a preferred embodiment, the method comprises wherein the impurity concentration is not more than about 0.015%.

In a preferred embodiment, the method comprises wherein the impurity is selected from the group consisting of an aziridinyl impurity, an amine impurity (such as but not limited to betamethylphenethyl amine), an organic impurity with potential pharmacologic effects.

In a preferred embodiment, the method comprises wherein the concentration of the impurity is less than 0.01% on a weight basis.

In a preferred embodiment, the method comprises wherein said pharmacologically active agent has a purity of at least 93% and not more than 100% at time of manufacture.

In a preferred embodiment, the method comprises wherein said administered dosage form is prepared using concentration of the present invention contains degradation product(s) less than about 7% of the starting concentration of said pharmacologically active agent.

In a preferred embodiment, the method comprises wherein said administered dosage form is prepared using concentration of the present invention contains degradation product(s) less than about 5% of the starting concentration of said pharmacologically active agent.

In a preferred embodiment, the method comprises wherein the symptoms are selected from the group consisting of inattentiveness, hyperactivity, and impulsivity.

In a preferred embodiment, the method comprises wherein the drug affects a receptor in an organ of the patient, especially wherein the drug affects a receptor in an organ of the patient wherein the organ is selected from the group consisting of the brain, and more particularly wherein the receptor is involved in the patient's neuropathic pathway.

In a preferred embodiment, the method comprises wherein the delivery of therapeutic or sub-therapeutic quantities of the above ingredient compositions may be accomplished through administration of single or multiple units given at one time or multiple times throughout the day.

In a preferred embodiment, the method comprises where in the composition is a pharmaceutically acceptable dosage form, and specifically wherein the composition is a dosage form selected from the group capsules, caplets, tablets, pills, powders, dissolving tablet or strip, a gum, wafer, cookie, solid in a gelatin capsule, soft gelatin capsule, liquid filled gelatin capsule, an aerosol, inhaler, and granules. The solid dosage forms of tablets, capsules, powders, and granules can also be prepared with coatings and shells such as enteric coatings and other coatings well known in the pharmaceutical formulating art.

In a preferred embodiment, the method comprises where the effective amount of the pharmaceutical composition is combined with one or more of a pharmaceutically acceptable excipient.

In a preferred embodiment, the method comprises where the dosage form employs a soft mass. The soft mass may be comprised of pharmaceutically acceptable thickener selected from the group of gelatin, natural gums, carbomer, glycols including polyethylene, propylene and glycerin, natural and synthetic oils.

In a preferred embodiment, the method comprises wherein solid compositions described above may also be employed as fillers in soft and hard-filled gelatin capsules using such excipients as lactose or milk sugar as well as high molecular weight polyethylene glycols and the like.

In a preferred embodiment, the method comprises wherein pharmaceutical composition is included in a dosage form for consumption by a mammal wherein the release the active ingredient(s), occurs in a certain part of the intestinal tract.

In a preferred embodiment, the method comprises wherein the release of the pharmaceutical composition is immediate, delayed, sustained, or combinations thereof.

In a preferred embodiment, the method comprises wherein the solid dosage form can be coated to mask or improve the taste, improve appearance or to alter the release rate.

In a preferred embodiment, the method comprises wherein one or more of the actives are in a microencapsulated form.

In a preferred embodiment, the method comprises wherein the dosage form is in a flowable state.

In a preferred embodiment, the method comprises wherein the flowable state is a preferably a liquid and more preferably a pharmaceutically acceptable emulsions, solutions, suspensions, syrups and elixirs. Besides inert diluents, the oral compositions can also include adjuvants such as wetting agents, emulsifying and suspending agents, sweetening, flavoring, and perfuming agents.

In a preferred embodiment, the method comprises wherein the composition employs an abuse deterrent technology, especially wherein the abuse deterrent technology is selected from the group of physical barriers, chemical barriers, agonist/antagonist combinations, aversive compounds, prodrugs, depot injections, a surface applied device, an implantable device, an aerosol, or combinations thereof.

In a preferred embodiment, the method comprises where the patient is given storage stable, composition for treating a disorder as described herein.

In a preferred embodiment, the invention comprises a storage stable amphetamine composition wherein the amount of degradation of said amphetamine or amphetamine derivative produced after storage at 1, 3 or 24 months at a temperature of approximately 25 or 30 deg. C. is less than 1, 3, 5, or 10% of the amount of amphetamine derivative in said storage stable amphetamine composition present at the time of manufacture of the dosage form.

In a preferred embodiment, the method comprises wherein the dosage form is storage stable, and as used herein, "storage stable" refers to the ability of the present compositions to have a long shelf life, including time spent on the shelf at a pharmacy as well as the entire time period after sale of the composition, during which time the composition maintains its effectiveness and pharmaceutically acceptable appearance. Accordingly, the present compositions are stable in that they exhibit a minimum amount of degradation during an extended period of storage.

In a preferred embodiment, the invention comprises wherein the amount of degradation of said pharmaceutical composition after storage for 26 months at 30.degree. C. is <1% of the total amount of composition (amphetamine) present at the time of manufacture of the dosage form and wherein the amount of degradation of said composition (amphetamine) after storage at 25.degree. C. for 30 months is <3% of the total amount of the pharmaceutical composition (amphetamine) present at the time of manufacture of the dosage form.

In a preferred embodiment, the method comprises wherein the composition of the present invention is packaged in a container suitable for storage and delivery of pharmaceutical composition.

In a preferred embodiment, the method comprises wherein the composition contains less than 10 ppm of an organic solvent, and especially where the organic solvent is selected from the group consisting of isopropanol and methyl tertiary butyl ether.

In a preferred embodiment, the method comprises a composition that contains an inorganic impurity from 0% to not more than 0.002% on a weight basis.

In a preferred embodiment, the drug substance preparation comprises a substituted amphetamine or a pharmaceutically acceptable salt, solvate, or mixture of two or more thereof, as the active pharmaceutical ingredient, and not more than 0.1% by weight of amphetamine-process related impurity, wherein the substituted amphetamine is produced by a process that comprises the steps of performing a stereospecific cuprate addition reaction upon an aziridine phosphoramidate compound to obtain a chiral aryl or aryl-alkyl phosphoramidate amphetamine precursor, and deprotecting the chiral aryl or aryl-alkyl phosphoramidate amphetamine precursor under acidic conditions effective to produce a substituted amphetamine.

In a preferred embodiment, the drug substance preparation comprises wherein the amphetamine-process related impurity is 2-methyl-3-phenyl-aziridine.

In another aspect, the invention provides wherein the substituted amphetamine is a racemic mixture of amphetamine isomers is comprised of equal parts amphetamine aspartate monohydrate (25%), amphetamine sulfate (25%), dextroamphetamine saccharate (25%), and dextroamphetamine sulfate (25%).

In another aspect, the invention provides wherein the substituted amphetamine is comprised of equal parts amphetamine aspartate hemihydrate (25%), amphetamine sulfate (25%), dextroamphetamine saccharate (25%), and dextroamphetamine sulfate (25%).

In another aspect, the invention provides wherein the substituted amphetamine is (2S)-1-phenylpropan-2-amine.

In another aspect, the invention provides a pharmaceutical composition comprising a drug preparation of highly pure active pharmaceutical ingredient, described herein, and one or more excipients.

In another aspect, the invention provides a drug product or dosage form comprising the pharmaceutical composition described herein and one or more additional excipients.

In another aspect, the invention provides wherein the drug product or dosage form is a tablet formulated to orally administer at least about 5 mg of the active pharmaceutical ingredient, or the molar equivalent amount of a salt thereof.

In another aspect, the invention provides wherein the drug product or dosage form is a tablet formulated to orally administer between about 1 mg and about 100 mg of the active pharmaceutical ingredient, or the molar equivalent amount of a salt thereof.

In another aspect, the invention provides a drug preparation of highly pure active pharmaceutical ingredient comprising not more than about 1000 ppm of the amphetamine process-related impurity.

In another aspect, the invention provides a drug preparation of highly pure active pharmaceutical ingredient comprising not more than about 500 ppm of the amphetamine process-related impurity.

In another aspect, the invention provides a drug preparation of highly pure active pharmaceutical ingredient wherein the amphetamine process-related impurity comprises a residual solvent in an amount of not more than about 0.3%, by weight, diethyl ether, tetrahydrofuran or 2-methyltetrahydrofuran.

In another aspect, the invention provides a drug preparation of highly pure active pharmaceutical ingredient, wherein the amphetamine process-related impurity comprises a residual metal in an amount of not more than about 10 ppm.

In another aspect, the invention provides a unit dosage form comprising 55-90%, by weight, of the highly pure active pharmaceutical ingredient herein and 10-45% total, by weight, of one or more excipients, wherein said unit dosage form contains at least about 5 mg of the active pharmaceutical ingredient, or the molar equivalent amount of a salt thereof.

In another aspect, the invention provides a drug preparation of highly pure active pharmaceutical ingredient comprising a substituted amphetamine or a pharmaceutically acceptable salt, solvate, prodrug, or mixture thereof, as the active pharmaceutical ingredient, and not more than 0.1% by weight of amphetamine-process related impurity, wherein the substituted amphetamine is selected from the group consisting of: dex-amphetamine; dex-N-methylamphetamine; dex-N-ethylamphetamine, and a racemic mixture of amphetamine isomers, wherein the dex-amphetamine is made according to the process comprising the steps 1a and 2a:

(1a) providing a compound of Formula 5:

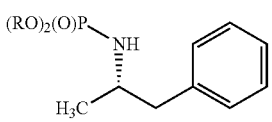

wherein R is alkyl or aryl; and (2a) deprotecting the compound of Formula 5 under acidic conditions effective to produce (2S)-1-phenylpropan-2-amine of Formula I:

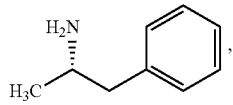

and wherein the racemic mixture of amphetamine isomers is made according to the process comprising the steps 1b and 2b:

(1b) providing a compound of Formula 6:

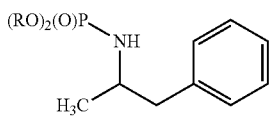

wherein R is alkyl or aryl; and (2b) deprotecting the compound of Formula 6 under acidic conditions effective to produce a racemic mixture of amphetamine isomers of Formula 7:

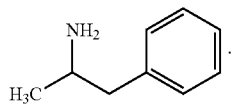

In another aspect, the invention provides wherein the acidic conditions of step 2a or 2b are aqueous hydrochloric, sulfuric or phosphoric acids.

In another aspect, the invention provides wherein the acidic conditions of step 2a or 2b are aqueous hydrochloric, sulfuric or phosphoric acids and wherein the aqueous acid water content is in an amount of 50% to 90%.

In another aspect, the invention provides wherein R in step 1a or 1b is R=methyl, ethyl, isopropyl or phenyl.

In another aspect, the invention provides wherein the step 1a of providing a compound of Formula 5 comprises the steps of:

Step (1)(a)(1) providing a compound of Formula 4:

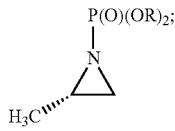

wherein R is alkyl or aryl and

Step (1)(a)(2) reacting the compound of Formula 4 with phenylmagnesium halide and a copper halide catalyst under solvent and temperature conditions effective to produce a compound of Formula 5 in a purity substantially free of any regioisomeric impurities.

In another aspect, the invention provides wherein the amphetamine-process related impurity is 2-methyl-3-phenyl-aziridine.

In another aspect, the invention provides wherein the regioisomeric purity of Formula 5 is >99% and the regioisomer is <0.1%.

In another aspect, the invention provides wherein R in Step (1)(a)(1) is R=methyl, ethyl, isopropyl or phenyl.

In another aspect, the invention provides wherein the copper halide catalyst in Step (1)(a)(2) is CuCl, CuCl$_2$, CuBr, CuF, Cu(OAc)$_2$, Cu(acac)$_2$, Cu(OMe)$_2$, Copper turnings or Copper nanoparticles.

In another aspect, the invention provides wherein the solvent in Step (1)(a)(2) is selected from the group consisting of an organic ether, a solvent that contains an organic ether, tetrahydrofuran, tetrahydrofuran mixed with 2-methyltetrahydrofuran, tetrahydrofuran mixed with methyl tert-butyl ether, and tetrahydrofuran mixed with toluene.

In another aspect, the invention provides wherein the temperature in Step (1)(a)(2) is a temperature of from about −10° C. to about 70° C.

In another aspect, the invention provides wherein said providing a compound of Formula 4 comprises the steps:

Step (1)(a)(1)(a)—providing a compound of Formula 3:

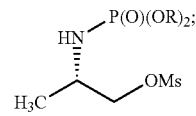

wherein R is alkyl or aryl; and

Step (1)(a)(1)(b)—reacting the compound of Formula 3 with the base under conditions effective to produce a compound of Formula 4.

In another aspect, the invention provides wherein the R in Step (1)(a)(1)(a) is R=methyl, ethyl, isopropyl or phenyl.

In another aspect, the invention provides wherein the base in Step (1)(a)(1)(b) is potassium hydroxide or potassium carbonate.

In another aspect, the invention provides wherein the Step (1)(a)(1)(a) of providing a compound of Formula 3 comprises the steps of:

Step (1)(a)(1)(a)(1)—providing a compound of Formula 2:

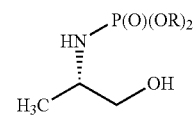

wherein R is alkyl or aryl; and

Step (1)(a)(1)(a)(2)—reacting the compound of Formula 2 with methanesulfonyl chloride and a base under conditions effective to produce a compound of Formula 3.

In another aspect, the invention provides wherein the R in Step 1a1a1 is R=methyl, ethyl, isopropyl or phenyl.

In another aspect, the invention provides wherein said providing a compound of Formula 2 comprises the steps:

Step (1)(a)(1)(a)(1)(a) providing a compound of Formula 1:

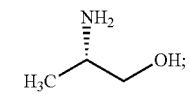

and

Step (1)(a)(1)(a)(1)(b) reacting the compound of Formula II with the appropriate

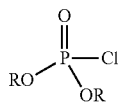

wherein R=alkyl or aryl under conditions effective to produce a compound of Formula 2.

In another aspect, the invention provides wherein the R in Step 1a1a1b is R=methyl, ethyl, isopropyl or phenyl.

In another aspect, the invention provides wherein the dex-N-methylamphetamine, is made by a process comprising:

providing a compound of Formula 8:

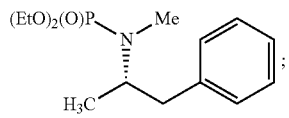

and deprotecting the compound of Formula 8 under acidic conditions effective to produce dex-N-methylamphetamine of Formula 9:

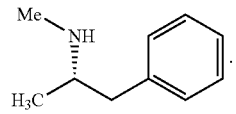

In another aspect, the invention provides wherein the acidic conditions are aqueous hydrochloric, sulfuric or phosphoric acids.

In another aspect, the invention provides wherein the step of providing a compound of Formula 8 comprises the steps of:

providing a compound of Formula 5b

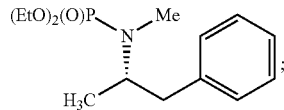

and reacting the compound of Formula 5b with a methyl alkylating agent and a base.

In another aspect, the invention provides wherein the dex-N-ethylamphetamine is made by a process comprising:

providing a compound of Formula 10:

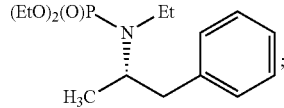

and deprotecting the compound of Formula 10 under acidic conditions effective to produce dex-N-ethylamphetamine of Formula 11:

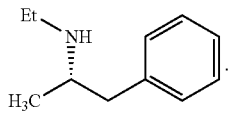

In another aspect, the invention provides, wherein the acidic conditions are aqueous hydrochloric, sulfuric or phosphoric acids.

In another aspect, the invention provides wherein the step of providing a compound of Formula 10 comprises the steps of:

providing a compound of Formula 5b

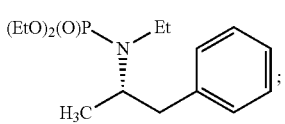

and reacting the compound of Formula 5b with a ethyl alkylating agent and a base.

In another aspect, the invention provides a drug substance preparation, wherein the active pharmaceutical ingredient is selected from the group consisting of: (S)-dimethyl (1-phenylpropan-2-yl)phosphoramidate (5a); (S)-diethyl (1-phenylpropan-2-yl)phosphoramidate (5b); (S)-diisopropyl (1-phenylpropan-2-yl)phosphoramidate (5c); (S)-diphenyl (1-phenylpropan-2-yl)phosphoramidate (5d); diethyl (1-phenylpropan-2-yl)phosphoramidate (6a); diphenyl (1-phenylpropan-2-yl)phosphoramidate (6b); dimethyl (1-phenylpropan-2-yl)phosphoramidate (6c); and diisopropyl (1-phenylpropan-2-yl)phosphoramidate (6d).

DETAILED DESCRIPTION OF THE INVENTION

Accordingly, the present invention comprises a controlled release, prodrug, or abuse-deterrent pharmaceutical composition, drug substance preparation, or dosage form for substituted amphetamines that are substantially free of process-related impurity(s). This aspect of being substantially free of process-related impurity(s) is made possible by the specific processes described herein for the manufacture of substituted amphetamines by synthesizing aziridine phosphoramidate compounds in specified solvents, at specified temperatures, and then converting to a novel aryl or aryl-alkyl phosphoramidate precursors using a modified organometallic compound such as a organocopper reagent, where the novel aryl or aryl-alkyl phosphoramidate precursor is then easily converted to the target compounds using known reactions, e.g. acidification, methylation of the nitrogen followed by dephosphorylation, etc. The specified solvents include an organic ether, a solvent mixture that contains an organic ether, tetrahydrofuran, tetrahydrofuran mixed with 2-methyltetrahydrofuran, a solvent mixture that contains tetrahydrofuran mixed with methyl tert-butyl ether, and a solvent mixture that contains tetrahydrofuran mixed with toluene. The specified temperatures include wherein aziridine-based process reaction is heated to above 40 degrees C., preferably above about 45 degrees C., and more preferably above about 48 degrees C. In one embodiment, the temperature is maintained from 48-51 deg. C. for about 30 minutes and then brought to room temperature.

Abuse Deterrent Compositions:

The invention comprises pharmaceutical compositions resistant to abuse and methods of making and using such compositions. The pharmaceutical compositions described herein include an outer shell and a drug composition containing one or more active drug substances. The drug composition included in the pharmaceutical compositions described herein may be a matrix composition, and the terms "drug composition" and "matrix composition" are used interchangeably herein.

The invention comprises abuse deterrent formulations in six categories, including: physical/chemical barriers, agonist/antagonist combinations, aversion, delivery system, prodrug, or a combination of the aforementioned.

Configurations, materials, and methods for producing abuse resistant pharmaceutical compositions having an outer shell positioned over a drug composition are detailed herein. In certain embodiments, the pharmaceutical compositions are provided as unit dosage forms suitable for oral administration.

The shell included in the pharmaceutical compositions described herein can be formulated to resist physical tampering, such as by chewing, crushing, chipping, grinding, or other applications of mechanical force that may compromise the physical integrity of the of the composition or result in particle size reduction. In certain embodiments, the shell included in the pharmaceutical compositions described herein is formulated to exhibit a hardness that resists physical tampering. In other embodiments, the shell is configured to resist physical tampering, such as by inclusion of one or more reinforcement elements. In still other embodiments, the shell is formulated and/or configured to maintain adherence between the shell and the drug composition, such that deformation and separation of the drug composition from the shell is made more difficult.

Of course, it will be understood that the shell included in the pharmaceutical compositions described herein may incorporate each of the features of the embodiments described herein. The shell included in the pharmaceutical compositions described herein, therefore, can be formulated and configured to resist chewing, crushing, chipping, grinding and other methods that may otherwise result in particle size reduction of the pharmaceutical composition and, thereby, provides a pharmaceutical composition that is resistant to abuse.

The drug composition included in the pharmaceutical compositions described herein may be formulated to resist abuse. For example, the drug composition may be formulated in such a way that the composition maintains a desired release profile of drug substance even if the pharmaceutical composition is subjected to physical tampering. In some embodiments, the drug composition may incorporate a gelling agent, which can render the pharmaceutical composition unfit for injection if attempts are made to introduce the composition into a liquid solution. In addition, or alternatively, the drug composition included in the pharmaceutical compositions described herein may include an antagonist to the drug substance to be delivered by the pharmaceutical composition. In such an embodiment, the drug composition is formulated such that the antagonist is only released when the pharmaceutical composition is subjected to physical and/or chemical tampering.

The above discussion is provided to present the utility of traditional or abuse deterrent compositions and not met, in any way, to limit the scope of this invention.

Physical/Chemical Barriers

Physical barriers like a polymer matrix can prevent chewing, pulverizing, cutting, grating, or grinding. Chemical polymer barriers can resist extraction of the active using common solvents like water, alcohol, or other organic solvents. Physical and chemical barriers can change the physical form of an oral drug rendering it less amenable to abuse.

Suitable matrix agents are natural or synthetic polymers capable of providing increased resistance to pulverizing or grinding. The matrix agent may be selected from the group consisting of agar, alamic acid, alginic acid, carmellose, carboxymethylcellulose sodium, chitosan, copovidone, dextrin, gelatin, hydroxyethyl cellulose, hydroxypropyl cellulose, hydroxypropyl methylcellulose, methylcellulose derivatives, microcrystalline cellulose, polyacrylic acid, polyalkalene oxide (e.g., polymethylene oxide, polyethylene oxide and polypropylene oxide), polyvinyl alcohol, povidone, propylene glycol alginate, polyvinylcaprolactam-polyvinyl acetate-polyethylene glycol graft copolymers, sodium alginate, starch, and vinylpyrrolidone-vinyl acetate copolymers. In one embodiment, the matrix agent is a polyethylene oxide. Polyethylene oxide is a non-ionic, water soluble polymer that is readily available in a wide range of molecular weight grades.

In another preferred embodiment, the invention comprises an abuse-deterrent pharmaceutical composition that comprises a block copolymer. Such a block copolymer may include a hydrophilic block copolymer, a hydrophobic block copolymer, or a combination thereof.

According to one embodiment of the present invention, the block copolymer may comprise the block in an amount of 20 to 95% by weight, and more specifically 40 to 95% by weight, based on the total weight of the copolymer. In addition, the block copolymer may comprise a hydrophilic or hydrophobic block in an amount of 5 to 80% by weight, and more specifically 5 to 60% by weight, based on the total weight of the copolymer.

The block copolymer may have a number average molecular weight of 1,000 to 50,000 Daltons, and more preferredly 1,500 to 20,000 Daltons.

According to one embodiment of the present invention, the polymer is biocompatible and may comprise one or more selected from the group consisting of polyethylene glycol or derivatives thereof, polyvinylpyrrolidone, polyvinyl alcohol, polyacrylamide, polylactide, polyglycolide, polymandelic acid, polycaprolactone, polydioxan-2-one, polyamino acid, polyorthoester, polyanhydride, polycarbonate and combinations thereof. Certain polymers, such as PLA, PGA, PLGA are known to have fast-release profiles, whereas other polymers such as polyanhydrides are known to have linear release profiles.

According to another embodiment of the invention, the active can be complexed with biocompatible polymers including those listed, but may also be bound as a dimer with biocompatible polymers.

The amphetamine is bound to one or more chemical moieties, denominated X and Z. A chemical moiety can be any moiety that decreases the pharmacological activity of amphetamine while bound to the chemical moiety as compared to unbound (free) amphetamine. The attached chemical moiety can be either naturally occurring or synthetic. Exemplary chemical moieties include, but are not limited to, peptides, including single amino acids, dipeptides, tripeptides, oligopeptides, and polypeptides; glycopeptides; carbohydrates; lipids; nucleosides; nucleic acids; and vitamins.

Exhaustive lists of moieties, abuse-resistant approaches, etc. contemplated for conjugation to the highly pure amphetamines of the present invention are referenced in U.S. Pat. Nos. 7,105,486, 7,659,253, 7,655,630, and 7,662,787, each of which is incorporated herein in its entirety.

Polynucleotides, polypeptides, polyaminoacids, and chemically modified variants are contemplated for dimerization to control administration and reduce abuse. For example, polynucleotide-amphetamine or polypeptide-amphetamine.

Drug-Polymer Matrix Layering

Where an active is encapsulated in multiple layers, a different drug-polymer mixture is contemplated for each layer. In one embodiment, an outer shell comprises a drug-polymer matrix that is hydrophilic and fast release such as PLGA-amphetamine, followed by one or more inner cores or inner shells having a drug-polymer matrix using a hydrophobic and linear release such as polyanhydride-amphetamine.

The matrix agent should be capable of ensuring the formation of a solid dosage form by extrusion, spray deposition, or by other processes; capable of aiding with extended release of the active substance, and/or capable of preventing abuse via pulverization or small volume extraction. The matrix agent can have a molecular weight of about 50K, 75K, 100K, 125K, 150K, 175K, 200K, 250K, 300K, 350K, 400K, 450K, 500K, 550K, 600K, 650K, 700K, 750K, 800K, 850K, 900K, 950K or 1000K Daltons. These values can also be used to define a range, such as about 75K Daltons to about 175K Daltons.

Agonist/Antagonist Combinations, and Aversion Technologies

An drug antagonist can be added to interfere with, reduce, or defeat the euphoria associated with abuse. The antagonist can be sequestered and released only upon manipulation of the product. For example, a drug product may be formulated such that the substance that acts as an antagonist is not clinically active when the product is swallowed but becomes active if the product is crushed and injected or snorted.

Aversion

Substances can be combined to produce an unpleasant effect if the dosage form is manipulated prior to ingestion or a higher dosage than directed is used.

The invention includes pharmaceutically acceptable surfactants that are useful in the practice of the present invention have solubility in oils, co-solvents, or aqueous media. The surfactant component helps in modulating the solubility of the compound as well in reducing the abuse potential by a dual mechanism by eliciting an irritant response when administered "as is" by nasal or injection routes, and, by co-eluting with the drug when extracted with the commonly used solvents such as aqueous and organic solvents. Surfactants produce tissue irritation when applied to nasal mucosa and will cause local irritation at an injection site.

Surfactants

Types of surfactants that may be useful in the practice of the present invention include non-ionic surfactants including fatty acid esters of glycerol or sorbitol; ethoxylated sorbitan fatty acid esters; polyethylene glycol fatty acid esters; polyethyleneglycol esters and polyethyleneglycol ethers; and polyethoxylated carboxylic acids. Additional surfactants that may be useful include vitamin E and derivatives thereof, e.g., PEGylated derivatives of vitamin E.

High molecular weight polymers may also be used to increase viscosity and encapsulate an active ingredient to cause an extended release profile to develop upon tampering with a drug-matrix.

Delivery System Including Depot Injectable Formulations and Implants

Certain drug release designs or the method of drug delivery can offer resistance to abuse. For example, a sustained-release depot injectable formulation that is administered intramuscularly or a subcutaneous implant can be more difficult to manipulate.

Polymer Shell Encapsulated Liquid Matrix

In one preferred embodiment, the invention comprises biodegradable polymer shell, an organic liquid matrix, and an active drug where the drug is soluble or otherwise conjugated or combined in the liquid matrix and the liquid is encapsulated by the shell. Upon injection, the polymer degrades over time, providing a primary extended release profile, and releasing the liquid matrix containing the drug. As the liquid matrix migrates through tissue and is itself degraded, a secondary extended release profile is developed for the drug. In one example, the shell is a polymer as described herein, and the liquid matrix is a suitable polar aprotic organic liquid such as, for example, those having an amide group, an ester group, a carbonate group, a ketone, an ether, a sulfonyl group, or a combination thereof. In one embodiment, the organic liquid is selected from N-methyl-2-pyrrolidone, 2-pyrrolidone, propylene glycol, polyethylene glycol, ethanol, acetone, tetrahydrofurfuryl alcohol, dimethyl isosorbide, acetic acid, lactic acid, methyl lactate, ethyl lactate, monomethyl succinate acid, monomethyl citric acid, glycofurol, glycerol formal, isopropylidene glycol, 2,2-dimethyl-1,3-dioxolone-4-methanol, dimethylformamide, dimethylacetamide, N,N-dimethylformamide, propylene carbonate, triacetin, dimethylsulfoxide, dimethylsulfone, epsilon-caprolactone, butyrolactone, caprolactam, and a mixture of two or more thereof.

Prodrug

A prodrug that lacks drug activity until transformed in the body (lung, liver, G.I., kidney, tissue) can be unattractive for intravenous injection or intranasal routes of abuse. In one preferred embodiment, the invention comprises both intracellular and extracellular prodrug bioactivation.

Tissue based bioactivation can be accomplished using an ester linkage that is removed by localized esterases. Lung enzymes have their own specific substrates.

Liver Prodrugs

In one preferred embodiment, the invention conjugates a drug with a polymer or chemical moiety that is not released until acted upon by liver cytochrome enzymes. For example, aromatic rings are metabolized by CYP2A6. CYP metabolism also includes dealkylation, dehydrogenation, reduction, hydrolysis, and oxidation.

Kidney Prodrugs

In one preferred embodiment, the invention contemplates conjugating drug to L-gamma-glutamyl or N-acetyl-L-gamma glutamic moieties so that they are metabolized by gamma-glutamyl transpeptidase before they are bioactive. Alternatively, conjugating to alkylglucoside moieties also provides for glycosylation based prodrugs.

Digestive Prodrugs

Formulating drug into microspheres or nanospheres that do not degrade until the spheres are subjected to an acidic pH is one digestive prodrug mechanism. Adding various chemical moieties is another mechanism. For example, formulating a prodrug with an amide will resist biochemical degradation until colonic pH is achieved. Conjugating the drug with a linear polysaccharide such as pectin will also delay activation until the combination reaches the bacteria in the colon.

Prodrugs from "Chiral Compound 5" and "Racemic Compound 6"

Prodrugs may also include compounds from synthetic pathways. Chiral compounds 5a-d, and racemic compounds 6a-d (the dimethyl-, diethyl-, diisopropyl-, and diphenyl-derivatives) are exemplary prodrugs.

Specifically, chiral compound 5a is (S)-dimethyl (1-phenylpropan-2-yl)phosphoramidate, Compound 5b is (S)-diethyl (1-phenylpropan-2-yl)phosphoramidate, Compound 5c is (S)-diisopropyl (1-phenylpropan-2-yl)phosphoramidate, and Compound 5d is (S)-diphenyl (1-phenylpropan-2-yl)phosphoramidate.

Specifically, racemic Compound 6a is diethyl (1-phenylpropan-2-yl)phosphoramidate, Compound 6b is diphenyl (1-phenylpropan-2-yl)phosphoramidate, Compound 6c is dimethyl (1-phenylpropan-2-yl)phosphoramidate, and Compound 6d is diisopropyl (1-phenylpropan-2-yl)phosphoramidate.

Combinations of Abuse Deterrent Technologies

Two or more of the above methods can be combined to deter abuse.

Combination Treatments

Combinations of therapeutic agents are administered according to aspects of the present invention. According to aspects of methods of the present invention, a composition of the present invention is administered to a patient as a component of a therapeutic treatment regimen along with at least one additional therapeutic agent.

The term "additional therapeutic agent" is used herein to denote a chemical compound, a mixture of chemical compounds, a biological macromolecule, such as a nucleic acid, an antibody, a protein or portion thereof, e.g., a peptide, or an extract made from biological materials such as bacteria, plants, fungi, or animal, particularly mammalian, cells or tissues which is a biologically, physiologically, or pharmacologically active substance, or substances, that acts locally or systemically in a patient to provide a beneficial effect in treatment of an amphetamine responsive condition.

According to aspects, combination therapies include: (1) pharmaceutical compositions of the present invention in combination with one or more additional therapeutic agents; and (2) co-administration of a pharmaceutical composition of the present invention with one or more additional therapeutic agents wherein the pharmaceutical composition of the present invention and the one or more additional therapeutic agents have not been formulated in the same composition. When using separate formulations, the pharmaceutical composition of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the pharmaceutical composition of the present invention and the one or more additional therapeutic agents used in methods of the present invention.

Commercial Packages

Commercial packages provided herein include a pharmaceutical composition of the present invention in a container suitable for storage and delivery of the dosage form.

A container suitable for storage and delivery of the pharmaceutical composition can be any of various sizes or shapes useful for containing and/or delivering the composition exemplified by, but not limited to, a jar, bottle, tube, vial, packet, sachet, pouch and can.

Optionally, the container is comprised of a ferrous alloy, aluminum, glass, plastic, laminates, or combinations thereof. The container further optionally includes one or more protective coatings.

A container for a pharmaceutical composition of the present invention optionally includes at least two separate compartments wherein the composition of the present invention is contained in one or more of the compartments. A second therapeutic agent may be contained in a second compartment, separate from the composition of the present invention, and may be dispensed therefrom for administration, or may be dispensed with the composition of the present invention prior to use. For example, a barrier between separate compartments may be pierced or removed to allow for co-mingling of composition of the present invention and the material in a second compartment.

Instructions for use of the present invention composition are optionally included in a commercial package, wherein the instructions are directed to a physician and/or to the patient. Included instructions to the patient optionally include instructions to regarding directions for use, warnings, precautions, and over dose treatment guidance.

Composition for use claims would follow a similar discussion as their method of use.

Definition: Substituted Amphetamines

Substituted Amphetamines means the class of compounds that include the parent compound, amphetamine, and compounds that feature a phenethylamine core with a methyl group attached to the alpha carbon and from 1-3 substitutions at various locations on the alpha-methyl-phenethylamine parent.

Substitutions contemplated herein include without limitation alpha-position substituents comprising alkyl groups as defined herein but especially C1-C3 alkyl, N-position substituents comprising alkyl groups as defined herein but especially C1-C3 alkyl, beta-position substituents comprising alkyl groups as defined herein but especially hydroxy or keto-, phenyl substituents at positions 2-5 comprising any alkyl or aryl group as defined herein, and combinations of substituents at one or more positions thereof.

Substituted Amphetamines also includes the optical isomers, such as D-amphetamine or L-amphetamine, of such compounds as well as enantiomerically pure compositions, and racemic mixtures in both equal and unequal amounts thereof. Enantiomeric forms, such as R—, S—, R—R—, S—S—, and R—S—, and prodrug forms, such as for example lisdexamfetamine, are also contemplated as included within the inventive subject matter.

Definition: Organic Moieties

Alkyl means any C1-C10 straight or branched chain alkyl, wherein said alkyl, is optionally substituted with C1-C6 alkyl, C2-C6 alkenyl, hydroxy, amino, halo, haloalkyl, thiocarbonyl, ester, thioester, alkoxy, alkenoxy, cyano, nitro, imino, alkylamino, aminoalkyl, sulfhydryl, thioalkyl, or sulfonyl.

Aryl means any alicyclic or aromatic, mono-, bi- or tricyclic, carbo- or heterocyclic ring, wherein the ring is either unsubstituted or substituted with one or more substituent(s) independently selected from the group including, but not limited to, alkylamino, amido, amino, aminoalkyl, azo, benzyloxy, C1-C9 straight or branched chain alkyl, C1-C9 alkoxy, C2-C9 alkenyloxy, C2-C9 straight or branched chain alkenyl, C3-C8 cycloalkyl, C5-C7 cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties, including alicyclic and aromatic structures; wherein the individual ring size is 5-8 members; wherein said heterocyclic ring contains 1-6 heteroatom(s) independently selected from the group consisting of O, N, and S; and wherein said aromatic or tertiary alkyl amine is optionally oxidized. Useful carbo- and heterocyclic rings include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

R may also be in certain preferred embodiments any C2-C10 straight or branched chain alkenyl or C1-C10 alkoxy, unsubstituted or optionally substituted with moieties listed above.

Non-limiting examples of substituted amphetamines as described herein include: α-Methyl-phenethylamine; β-Ketoamphetamine; β-Hydroxyamphetamine, (1S,2S)—; β-Hydroxyamphetamine, (1R,2S)—; α-Methylamphetamine; N-Propylamphetamine; N-Methylamphetamine, (1R,2S)—; N-iso-Propylamphetamine; N-Ethylamphetamine; N-(2-chlorobenzyl)-1-phenylpropan-2-amine; 4-Methylthioamphetamine; 4-Methylamphetamine; 4-Methoxyamphetamine; 4-Iodoamphetamine; 4-Hydroxyamphetamine; 4-Fluoroamphetamine; 4-Ethoxyamphetamine; 4-Chloroamphetamine; 4-Bromoamphetamine; 3-Trifluoromethylamphetamine; 3-Methylamphetamine; 3-Fluoroamphetamine; 2-Methylamphetamine; 2-Fluoroamphetamine; β-Keto-N-methylamphetamine; β-Keto-N-ethylamphetamine; β-Hydroxy-N-methylamphetamine, (1 S,2S)—; β-Hydroxy-N-methylamphetamine, (1R,2S)—; α,β-Dimethylamphetamine; X,X-Dimethoxyamphetamine; N-Methyl-α-methylamphetamine; N-Methyl-N-propargylamphetamine, (R)—N-Benzyl-N-methylamphetamine; N,N-Dimethylamphetamine; 4-Methyl-N-methylamphetamine; 4-Methoxy-N-methylamphetamine; 4-Methoxy-N-ethylamphetamine; 4-Hydroxy-N-methylamphetamine; 4-Fluoro-N-methylamphetamine; 4-Chloro-α-methylamphetamine; 3-Trifluoromethyl-N-ethylamphetamine, (S)—; 3-Trifluoromethyl-N-ethylamphetamine; 3-Methoxy-4-methylamphetamine; 3,4-Methylenedioxyamphetamine; 3,4-Dimethylamphetamine; 3,4-Dihydroxyamphetamine; 2-Chloro-α-methylamphetamine; β-Keto-N,N-dimethylamphetamine; β-Keto-N,N-diethylamphetamine; β-Keto-4-methyl-N-methylamphetamine; β-Keto-4-methoxy-N-methylamphetamine; β-Keto-4-fluoro-N-methylamphetamine; β-Keto-4-bromo-N-methylamphetamine; β-Keto-3-chloro-N-tert-butylamphetamine; β,4-Dihydroxy-N-methylamphetamine; β,3,4-Trihydroxyamphetamine; (R)—X,X,X-Trimethoxyamphetamine; 4,5-Methylenedioxy-3-methylamphetamine; 3-Methoxy-4,5-methylenedioxyamphetamine; 3,4-Methylenedioxy-N-methylamphetamine; 3,4-Methylenedioxy-N-hydroxyamphetamine; 3,4-Methylenedioxy-N-ethylamphetamine; 3,4-Methylenedioxy-2-methylamphetamine; 2,5-Dimethoxy-4-trifluoromethylamphetamine; 2,5-Dimethoxy-4-propylamphetamine; 2,5-Dimethoxy-4-nitroamphetamine; 2,5-dimethoxy-4-methylthioamphetamine; 2,5-Dimethoxy-4-methylamphetamine; 2,5-Dimethoxy-4-iodoamphetamine; 2,5-Dimethoxy-4-fluoroethylamphetamine; 2,5-Dimethoxy-4-fluoroamphetamine; 2,5-Dimethoxy-4-ethylamphetamine; 2,5-Dimethoxy-4-chloroamphetamine; and 2,5-Dimethoxy-4-bromoamphetamine.

Definition: Impurity

Impurity means product-related impurity(s), process-related impurity(s), and other impurity(s). Impurities that are structurally similar to the active pharmaceutical ingredient ("API") are commonly referred to as "product-related impurities." In the case of APIs containing chiral centers where one enantiomer shows therapeutic effect, while the other enantiomer shows either no effect, minimal effect, or an undesirable effect, the latter enantiomer represents a type of product-related impurity, commonly referred to as an "enantiomeric impurity."

Impurities that are not structurally similar to the API, and are introduced by the process(es) used to make the API, are commonly referred to as "process-related impurities." Process-related impurities can comprise such things as unreacted starting materials, materials added to purify the API, by-products of side reactions, and the like, which do not structurally resemble the API. Process-related impurities may also comprise residual solvents and heavy metals. However, due to their known toxic properties, residual solvents and heavy metals are often considered apart from other types of process-related impurities. Although the copper and magnesium used in the reaction should not in theory carry forward into the product, even producing a bluish color if the wash step is ineffective and providing an indicator of a problem, the amphetamine product may comprise copper impurities at less than 20 ppm and magnesium impurities at less than 20 ppm.

Thus, in one aspect, the invention provides a pharmaceutical composition or drug substance preparation containing dextroamphetamine, i.e. (2S)-1-phenylpropan-2-amine, or a pharmaceutically acceptable salt, solvate, ester or prodrug thereof, as the API, and limited amounts of specific product-related impurities such as levoamphetamine, i.e. (2R)-1-phenylporpan-2amine, and limited amounts of process-related impurities such as 2-methyl-3-phenyl-aziridine.

In one embodiment of this aspect, all of the impurities present in these drug substance preparations are limited to about 5%, 4%, 3%, 2%, 1%, or less of the total weight of the drug substance preparation (i.e., [sum of weight(s) of one or more impurities]/[total weight of drug substance preparation]×100% is less than 5%, 4%, 3%, 2%, 1%, or less).

In another embodiment, the invention provides a drug substance preparation containing (2S)-1-phenylpropan-2-amine, or a pharmaceutically acceptable salt, solvate, ester or prodrug thereof, as the API, and about 2%, 1%, 0.5%, 0.25%, 0.1%, 0.05%, 0.025%, 0.01%, 0.005%, 0.0025%, or 0.001% of the total weight of the drug substance preparation as product-related impurities.

In another embodiment, the invention provides a drug substance preparation having from 0.001%-0.01%, 0.005%-0.05%, 0.01%-0.1%, 0.05%-0.5%, or 0.1%-1%, of any one specific impurity, by weight. In another embodiment, the invention provides a drug substance preparation having from 0.001%-0.01%, 0.005%-0.05%, 0.01%-0.1%, 0.05%-0.5%, 0.1%-1%, or 0.5%-5%, by weight, of the specific product-related impurities, process-related impurities, identified herein.

In a preferred aspect as it relates to pediatric toxicity, a non-limiting example of an impurity as defined herein is 2-methyl-3-phenyl-aziridine. In another preferred aspect, other non-limiting examples of impurities as defined herein include: any aziridine compounds, as well as specifically cis/trans 2-methyl-3-phenylaziridine; cis/trans-1,2-dimethyl-3-phenylaziridine; Phenyl-2-propanone; DiMethyl-AMP; PhenylPropanolamine; Ephedrine; Methyl-Ephedrine; 1,3-dimethyl-2-PhenylNaphthalene; 1-Benzyl-3-MethylNaphthalene; 4-methyl-5-phenyl-pyrimidine; N-formyl-AMP; 1,3-Diphenyl-2-propylamine; N,N-Di-(b-phenylisopropyl)methylamine, isomer 1; N,N-Di-(b-phenylisopropyl)methylamine, isomer 2; 1-Benzyl-3-methyl-naphthalene; 1,3-Dimethyl-2-phenylnaphthalene; 2,6-Dimethyl-3,5-diphenylpyridine; 2,4-Dimethyl-3,5-diphenylpyridine; 2,6-Diphenyl-3,4-dimethylpyridine; N,N-Di-(b-phenylisopropyl)formamide, isomer 1; N,N-Di-(b-phenylisopropyl)formamide, isomer 2; 2-Benzyl-2-methyl-5-phenyl-2,3-dihydropyrid-4-one; Pyridine 14a; Pyridine 7a; Pyridine Xa; Phenyl-2-propanol; Acetylamphetamine; N-(b-Phenylisopropyl)benzaldimine; Benzylamphetamine; 1-Oxo-1-phenyl-2-(b-phenylisopropylimino)propane; Benzoylamphetamine; 2-Oxo-1-phenyl-(b-phenylisopropylamine)ethane; 2-Methyl-3-phenylaziridine; Dimethyl-3-phenylaziridine; 2-Phenylmethylaziridine; Phenyl-2-propanoxime, isomer one; and Phenyl-2-propanoxime, isomer two.

Copper

Copper catalyst used in the process includes CuCl, CuCl2, CuBr, CuF, Cu(OAc)2, Cu(acac)2, Cu(Ome)2, copper nanoparticles, copper turnings, copper grit, copper powder, copper shot, copper foil, copper flake, copper disk, copper precipitate, copper mist, copper dust, copper granules, and copper slug. Copper nanoparticles means particles having an average diameter of about 1 nm-100 nm.

Alkyl Phosphonic Group

Alkyl Phosphonic Acid Protecting group means any group attached to the aziridine nitrogen having one or more alkyl groups attached to a phosphorous atom thereby having the formula P—O—(OR)$_2$, where R1 and R2 can be the same or different, and include without limitation any alkyl, alkoxy or aryl group as defined herein, and including any and all equivalents thereof.

Definition: Solvent

Solvents, as used and exemplified herein, are not intended to be limiting and may include without limitation solvents selected from Ligroine, Pentane, Hexane, Heptane, Octane, Cyclopentane, Cyclohexane, Cycloheptane, Cyclooctane, Dichloromethane, Chloroform, Carbon tetrachloride, 1,2-Dichloroethane, 1,1,2,2-Tetrachloroethane, Methylacetate, Ethylacetate, Propylacetate, Butylacetate, Dimethylformamide, Diethylformamide, Dimethylacetamide, Diethylacetamide, Diethylether, Diisopropylether, methyl tert-Butyl ether, THF, Dioxane, Acetonitrile, Sulfolane, DMSO, HMPT, NMP or mixtures of these solvents. Preferred solvents are Dichloromethane, Chloroform, Ethyl acetate, Propyl acetate, Butyl acetate, Dimethylformamide, Diethylformamide, Dimethylacetamide, Diethylacetamide, Diisopropylether, methyl tert-Butyl ether, THF, Dioxane, Acetonitrile or mixtures of these. Especially preferred solvents are Dichloromethane, Chloroform, Ethyl acetate, Butyl acetate, Dimethylformamide, Dimethylacetamide, methyl tert-Butyl ether, THF, Dioxane, Acetonitrile or mixtures of these.

Definition: Regiospecific

The amphetamine and amphetamine derivatives made by the process herein are stereospecific and regioselective. The process chemistry does not operate at the chiral center.

The term(s) regioselective or regioselectivity, means without limitation, by way of explanation, the preference of one direction of chemical bond making or breaking over all other possible directions. It can often apply to which of many possible positions a reagent will affect, such as which proton a strong base will abstract from an organic molecule, or where on a substituted benzene ring a further substituent will add. Because of the preference for the formation of one product over another, the reaction is selective. This reaction is regioselective because it selectively generates one constitutional isomer rather than the other.

The term regiospecific is used if one product is formed exclusively. Whereas, a reaction that selectively generates one possible product over another is called regioselective, that is, a choice of final product exists, regiospecific reactions are those reactions where the same choice isn't there. A regiospecific reaction exclusively gives only one, specific product.

The term(s) stereoselective or stereoselectivity, means without limitation, by way of explanation, the property of a chemical reaction in which a single reactant forms an unequal mixture of stereoisomers during the non-stereospecific creation of a new stereocenter or during the non-stereospecific transformation of a pre-existing one. The selectivity arises from differences in steric effects and electronic effects in the mechanistic pathways leading to the different products.

The term stereospecific means the property of a reaction mechanism that leads to different stereoisomeric reaction products from different stereoisomeric reactants, or which operates on only one (or a subset) of the stereoisomers.

The literature, Zwierzak, incorrectly states that the product from the cuprate addition to the aziridine phosphoramidate is always regiospecific, but this is not the case, as evidenced and acknowledged by the U.S. Patent & Trademark Office in the grant of U.S. Pat. Nos. 9,278,904, and 9,321,794. The prior art appears to confuse the term regiospecificity, a detail of chemistry understood by Examiner Chen in the granting of the above patents. In attempting to copy the literature process, it has also been discovered that the process 3-5% of 6 (a,b,c or d) in the crude product, that it could not be removed later in the synthetic sequence. The presence of two products means that the process is not regiospecific, and by stating that it was regiospecific when it is not, the literature does not recognize the problem of the existence of the impurity. It was also found that if you used a single solvent (5b crystallizes from heptane or petroleum ether), then you did not remove the corresponding 6b. It is required to leave a residue of the reaction solvent (THF) in the mixture to separate the 5b from 6b.

Interestingly, it has been discovered that a ratio of specific solvents yielded the most preferred embodiment. This ratio comprises about 7 part heptane and 1 part THF for 5b, and the other versions of 5 (a, c or d) needed other solvent mixtures, but the common item was that it was required to leave a residue of THF in the mixture.

Accordingly, the chiral process relates to processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursor using an organometallic compound such as a copper salt, where the novel aryl or aryl-alkyl phosphoramidate precursor is then easily converted to the target compounds using known reactions, e.g. acid dephosphorylation, methylation of the nitrogen followed by acid dephosphorylation, etc.

Dosage Forms

In still another aspect, the invention provides dosage forms comprising therapeutically effective amounts of substituted amphetamine, or a pharmaceutically acceptable salt thereof, as the API with limited quantities of impurities arising from the drug substance used to prepare the pharmaceutical compositions used to make these dosage forms. These dosage forms can be designed for oral administration, and, in such instances, may take any acceptable form, including tablets, capsules, caplets, powders, and various granular forms. These dosage forms comprise pharmaceutical compositions that, in turn, comprise the drug substance preparations of the invention, which contain substituted amphetamine, or a pharmaceutically acceptable salt thereof, as the API, and limited amounts of impurities, as discussed above.

Drug Preparations

As used herein, the terms "drug substance" and "drug substance preparation," refers to the API-containing material that is used to formulate, along with excipients, the pharmaceutical compositions, dosage forms, and drug products of the invention. It is composed of the API, and limited quantities of specific product-related impurities, and process-related impurities.

The term "excipient," as used herein, refers to those components of a pharmaceutical composition, dosage form, or drug product, other than the drug substance, that are intentionally included in the composition or formulation to either facilitate manufacture, enhance stability, control the release of the API from the drug product, assist in product identification, or enhance any other product characteristics, including, for example, the pharmacokinetics of the drug product. Generally, excipients may be thought of as the "inactive ingredients" of the pharmaceutical composition, dosage form, or drug product, in the sense that they exert no direct therapeutic effect. However, excipients can have a significant effect on the pharmacokinetic characteristics of pharmaceutical compositions, dosage forms, or drug products containing the API, by influencing such parameters as dissolution, and release of the API.

As used herein, the term "pharmaceutical composition" is used to refer to compositions of matter comprising the drug substance and one or more pharmaceutically acceptable excipients. Additionally, these terms are meant to refer to compositions of matter (containing the drug substance and one or more excipients) that are used to prepare drug products or dosage forms, along with one or more additional excipients.

As used herein, the terms "drug product," "dosage form," or "finished product" are used interchangeably to refer to a finished pharmaceutical product or medicament that is suitable for administration to a human patient. The drug product or dosage form comprises the drug substance and pharmaceutically acceptable excipients, and can also be thought of as comprising a pharmaceutical composition in combination with one or more additional excipients. One example of a drug product or dosage form is a "tablet dosage form," or "tablet," which is formulated and manufactured for the gastrointestinal administration of the API by an oral route (i.e., oral administration).

Pharmaceutical Compositions

In another aspect, the present invention provides pharmaceutical compositions comprising the drug substance preparations described above.

As described above, substituted amphetamine-containing drug substance preparations include limited product-related impurities, and process-related impurities. Since these drug substance preparations are used to prepare the pharmaceutical compositions of the invention, the pharmaceutical compositions of the invention also include limited product-related impurities, and process-related impurities.

Consequently, in embodiments of this aspect of the invention, the pharmaceutical compositions of the invention comprise substituted amphetamine as the API, and further comprise limited quantities of product-related impurities and/or process-related impurities.

Pharmaceutical Composition Ranges

In certain embodiments, the invention provides pharmaceutical compositions having substituted amphetamine, or a pharmaceutically acceptable salt thereof, as the API, and one or more pharmaceutically acceptable excipients, with substituted amphetamine comprising about 30%, 35%, 40%, 45%, 50%, or 55% or more of the total weight of the unit dosage form. According to these embodiments, the drug substance preparation used in the compositions and dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, and/or process-related impurities.

Composition Impurities Ranges

In these embodiments, the present invention provides pharmaceutical compositions in which all of the impurities deriving from the drug substance preparations of the invention represent about 2%, 1%, 0.5%, 0.25% 0.1%, 0.05%, 0.025%, 0.01%, or less of the total weight of the pharmaceutical composition (i.e., [sum of weight(s) of impurities deriving from the drug substance preparation]/[total weight of pharmaceutical composition]×100%). In certain embodiments of this aspect, the invention provides pharmaceutical compositions containing substituted amphetamine, or a pharmaceutically acceptable salt thereof, as the API, and about 0.5%, 0.25%, 0.1%, 0.05%, 0.025%, 0.01%, or 0.005% or less of the total weight of the pharmaceutical compositions as impurities arising from the drug substance preparation used to prepare the composition. In other embodiments, the invention provides a pharmaceutical composition having from 0.001%-0.01%, 0.01%-0.1%, or 0.1%-1% of one or more impurities, by weight, wherein the impurities derive from the drug substance preparation used to prepare the pharmaceutical composition. In another embodiment, the invention provides a pharmaceutical composition having from 0.001%-0.01%, 0.01%-0.1%, or 0.1%-1%, by weight, of the specific product-related impurities and/or process-related impurities identified herein.

Composition Active Weight Ranges

In certain embodiments of this aspect, the invention provides a pharmaceutical composition having a drug substance preparation component containing substituted amphetamine, or a pharmaceutically acceptable salt thereof, as the API, admixed with one or more pharmaceutically acceptable excipients, wherein the weight of the drug substance preparation is more than about 30%, 35%, 40%, 45%, 50%, or 55% of the total weight of the pharmaceutical composition, and further having limited amounts of the impurities arising from the drug substance preparation described above. In certain embodiments of this embodiment, the drug substance preparation component can be 57% or more, 60% or more, or 63% or more of the total weight of the pharmaceutical composition. In some of these embodiments, the pharmaceutical composition is designed to contain about 2 mg or more, about 3 mg or more, about 4 mg or more, about 5 mg or more, about 6 mg or more, about 7 mg or more, about 8 mg or more, about 10 mg or more, about 15 mg or more, about 20 mg or more, about 25 mg or more, about 30 mg or more, about 35 mg or more, about 40 mg or more, and 50 mg or more, about 60 mg or more, about 70 mg or more, or a range of about 1-100 mg of substituted amphetamine as the API in the pharmaceutical composition.

Designed Composition Features

The invention also relates to pharmaceutical compositions and processes for making pharmaceutical compositions that exhibit one or more superior properties relative to other compositions comprising substituted amphetamine, or a pharmaceutically acceptable salt thereof, as the API. These superior properties include, but are not limited to, one or more of the following: improved bioavailability, improved solubility of the pharmaceutical composition, improved disintegration times for immediate release oral dosage forms, improved dissolution times for immediate release oral dosage forms, decreased tablet friability, increased tablet hardness, improved safety for oral dosage forms, reduced moisture content and/or hygroscopicity for oral dosage forms, improved composition wettability, improved particle size distribution of granules containing the API, improved composition compressibility, improved composition flow properties, improved chemical stability of the final oral dosage form, improved physical stability of the final oral dosage form, decreased tablet size, improved blend (or composition) uniformity, improved dose uniformity, increased granule density for wet granulated compositions, reduced water requirements for wet granulation, reduced wet granulation time, and/or reduced drying time for wet granulated mixtures.

Tablet Dosage Form

The unit dosage form of these embodiments can be provided as a unit dosage form specifically suited for oral administration (e.g., a tablet). This embodiment of the invention is manufactured using a pharmaceutical composition comprising substituted amphetamine, or a pharmaceutically acceptable salt thereof, as the API, that has from 30% to 90%, 35% to 90%, 40% to 90%, 45% to 90%, 50% to 90%, or 55% to 90% by weight API, and from 10% to 45% by weight inactive pharmaceutical ingredients, and from 2%-0.001% total (of the total weight of the dosage form) of the impurities arising from the drug substance preparation as described above. In a specific embodiment, the unit dosage form has from 55% to 85% by weight API and 15%-45% by weight inactive pharmaceutical ingredients. In another specific embodiment, the unit dosage form has from 55% to 75% by weight API and from 25% to 45% by weight inactive ingredients. In another specific embodiment, the unit dosage form has from 60% to 70% by weight API and from 30% to 40% by weight inactive pharmaceutical ingredients.

Tablet Dimensions Ranges

In another embodiment, the invention provides a tablet dosage form having between 320 to 480 mg substituted amphetamine, or therapeutically equivalent amount of a pharmaceutically acceptable salt thereof, as the API, where the long axis of the tablet is from about 0.50 to 0.90 inches, 0.55 to 0.8 inches, 0.6 to 0.8 inches, and the tablet width is from about 0.3 to 0.4 inches. According to this embodiment, the dosage form also has a limited amount of impurities arising from the drug substance preparation, wherein the total weight of these impurities is 1% or less of the total weight of tablet dosage form. In certain embodiments, the tablet dosage form is no longer than 0.82 inches, no longer than 0.80 inches, no longer than 0.77 inches, no longer than 0.72 inches, or no longer than 0.70 inches. In other embodiments, the tablet dosage form is no wider than 0.41 inches, no wider than 0.40 inches, no wider than 0.38 inches, or no wider than 0.35 inches. In yet another embodiment of the invention, the total volume of the tablet dosage form is less than 0.70 cm$^3$, less than 0.65 cm$^3$, less than 0.60 cm$^3$, less than 0.55 cm$^3$, less than 0.50 cm$^3$, or less than 0.45 cm$^3$.

Tablet Excipients

In some embodiment, each tablet has one or more excipients chosen from disintegrants, binders, diluents, glidants, lubricants, coloring agents, stabilizers, preservatives, and/or flavoring agents. In certain embodiments, each tablet has substituted amphetamine, or a pharmaceutically acceptable salt thereof, as the API, and limited amount of impurities arising from the drug substance preparation as described above, plus one or more binders, one or more diluents, one or more disintegrants, one or more glidants, one or more lubricants, and if desired, one or more optional ingredients. In certain embodiments, the tablet dosage form is coated. Excipients well-known in the art and included herein, may be found in the Handbook of Pharmaceutical Excipients, by Rowe, et al., Pharmaceutical Press 2012, incorporated herein by reference in its entirety.

Excipient Ranges

The excipients used to prepare the unit dosage forms of the invention include one or more excipients chosen from disintegrants, binders, diluents, glidants, and lubricants, as well as any desired optional ingredient. Thus, in one set of embodiments of the invention, the unit dosage form has an excipient that is a disintegrant. The amount of disintegrants in the dosage form of the invention can be 45% or less, 40% or less, 35% or less, 30% or less, or less than 25% of the total weight of the unit dosage form. In another set of embodiments of the invention, the unit dosage form has an excipient that is a binder. The amount of binder in the dosage form can be 20% or less, 15% or less, 10% or less, or less than 8% of the total weight of the unit dosage form. In yet another set of embodiments of the invention, the unit dosage form has an excipient that is a diluent. The amount of diluent in the unit dosage form can be 20% or less, 17% or less, 15% or less, or less than 12% of the total weight of the unit dosage form. In still another set of embodiments of the invention, the unit dosage form has an excipient that is a glidant. The amount of glidant in the unit dosage form can be 7% or less, 5% or less, 3% or less, or less than 2% of the total weight of the unit dosage form. In another set of embodiments of the invention, the unit dosage form has an excipient that is a lubricant. The amount of lubricant in the unit dosage form can be 10% or less, 5% or less, 3% or less, or less than 2% of the total weight of the unit dosage form.

Excipients Inactive Pharmaceutical Ingredients

The compositions and unit dosage forms of the invention can have a number of different ingredients besides the API. Depending on the dosage strength, a unit dosage form has an amount of API sufficient for achieving a therapeutic effect in a target population. However, "inactive pharmaceutical ingredients" may also need to be present to achieve a therapeutically effective release of the API. Thus, the amount and type of inactive ingredients help achieve a therapeutically effective release of the therapeutic agent. In one aspect of the invention, a tablet unit dosage form is provided having the following inactive ingredients: one or more disintegrants in an amount sufficient to facilitate break-up (disintegration) of the tablet after administration (e.g., providing an immediate release dissolution profile), one or more binders in an amount sufficient to impart adequate cohesiveness to the tablet and/or provide adequate free flowing qualities by formulation of granules of desired size and hardness, one or more diluents in an amount sufficient to impart satisfactory compression characteristics, one or more lubricants in an amount sufficient to provide an adequate flow rate of the granulation and/or prevent adhesion of the material to the die/punch, or to reduce interparticle friction, and/or facilitate ejection from the die, and if desired, various optional ingredients to impart desired characteristics to the dosage form.

Solid pharmaceutical formulations that are compacted into a dosage form, such as a tablet, may include excipients whose functions include helping to bind the API and other excipients together after compression.

Tablet Weight Ranges

In a specific embodiment, the invention provides a tablet dosage form containing about 400 mg substituted amphetamine, or a molar equivalent amount of a pharmaceutically acceptable salt thereof, and having about 30%, 35%, 40%, 45%, 50%, or 55%, or more, by weight, of substituted amphetamine in the tablet, and limited amounts of impurities arising from the drug substance preparations as described above, wherein the total weight of the impurities in the tablet is 0.1% or less of the total weight of the tablet. The tablet dosage forms of this embodiment are specifically suited for oral administration.

Capsules and Caplets

In a related embodiment, the unit dosage form is a capsule dosage form. In this embodiment, the capsule dosage form has substituted amphetamine, as the API, and limited amounts of impurities arising from the drug substance preparations used to make the pharmaceutical compositions that go into the capsules, and one or more pharmaceutically acceptable excipients as additional components.

With a capsule dosage form, the one or more excipients can be chosen from disintegrants, binders, diluents, glidants, lubricants, coloring agents, stabilizers, preservatives, and/or flavoring agents. In certain embodiments, the capsule dosage form comprises a hard gelatin capsule that contains a pharmaceutical composition of the invention.

In a related set of embodiments, the unit dosage form is a caplet dosage form.

Inactive Ingredients

The oral unit dosage forms of the present invention can contain any of the following inactive ingredients, or compounds of a similar nature: a diluent; a binder; a disintegrating agent (disintegrant); a lubricant; a glidant; and optional ingredients such as coloring agents, stabilizers, preservatives and/or flavoring agents or flavor masking agents. In addition, dosage forms of the invention can contain various other materials which modify the physical form of the dosage unit, for example, polymeric coatings (e.g., cellulosics, methacrylates, or acrylates), sugar coatings, shellac coatings, color coatings, wax coatings, or other types of coatings. In some preferred embodiments, the inactive ingredients are gelatin capsules, hydroxypropyl methylcellulose, methacrylic acid copolymer, opadry beige, sugar spheres, talc, and triethyl citrate. Gelatin capsules may also contain edible inks, kosher gelatin, and titanium dioxide.

Free Acid Forms

The unit dosage form of these embodiments of the invention is suited for gastrointestinal administration by an oral route (e.g., a tablet to be taken by mouth; oral administration). In some of these embodiments, substituted amphetamine is present as 57% or more, 60% or more, or 63% or more of the total weight of the of the unit dosage form. In some of these embodiments, the unit dosage form has about 2 mg or more, about 3 mg or more, about 4 mg or more, about 5 mg or more, about 6 mg or more, about 7 mg or more, about 8 mg or more, about 10 mg or more, about 15 mg or more, about 20 mg or more, about 25 mg or more, about 30 mg or more, about 35 mg or more, about 40 mg or more, and 50 mg or more, about 60 mg or more, about 70 mg or more, or a range of about 1-100 mg, substituted amphetamine in the free acid form (or a therapeutically equivalent amount of a pharmaceutically acceptable salt thereof) contained within each unit dosage form (i.e., tablet). In one specific embodiment, approximately 20 mg of substituted amphetamine is present in a tablet dosage form as the free acid, and comprises from 65% to 68% of the total weight of the tablet dosage form.

Active to Inactive Ranges by Weight

In other embodiments of this aspect of the invention, the invention provides a substituted amphetamine-containing tablet dosage forms having from 55% to 90% by weight substituted amphetamine and from 10% to 45% by weight inactive pharmaceutical ingredients. According to this embodiment, the drug substance preparation used in preparing the tablet dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, and/or process-related impurities. In these embodiments, the tablet dosage form is specifically designed for oral administration.

In other embodiments of this aspect of the invention, the substituted amphetamine-containing tablet dosage form has from 55% to 85% by weight substituted amphetamine, and from 15% to 45% by weight inactive pharmaceutical ingredients. In still other embodiments of this aspect of the invention, the substituted amphetamine-containing tablet dosage form has from 55% to 75% by weight substituted amphetamine, and from 25% to 45% inactive ingredients. In still other embodiments of this aspect of the invention, the substituted amphetamine-containing tablet dosage form has from 60% to 70% by weight substituted amphetamine and from 30% to 40% inactive pharmaceutical ingredients.

The substituted amphetamine-containing unit dosage forms of the present invention generally have 55% or more of the total weight of the unit dosage form as substituted amphetamine, with the remaining weight comprised of one or more pharmaceutically acceptable excipients. According to these embodiment, the drug substance used in the compositions used to manufacture the unit dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, and/or process-related impurities.

Coating

In another set of embodiments of the invention, the unit dosage form, containing substituted amphetamine, or a pharmaceutically acceptable salt thereof, and one or more excipients, is coated. In one set of embodiments of the invention, the weight of the coating is from 0.1% to 10% of the total weight of the unit dosage form. In another set of embodiments, the weight of the coating is from 0.1% to 8% of the total weight of the unit dosage form. In another set of embodiments, the weight of the coating is from 0.1% to 5% of the total weight of the unit dosage form.

Unit Dosage Forms and Pharmacokinetic Profiles

The present invention also relates to substituted amphetamine-containing unit dosage forms having 55% or more by weight of substituted amphetamine that yield a pharmacokinetic profile that is substantially bioequivalent to that known for existing commercial substituted amphetamine products. According to embodiment of this aspect of the invention, the drug substance used in the pharmaceutical compositions and dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, and/or process-related impurities.

As used herein, substantially bioequivalent refers to Cmax (maximum plasma concentration) and AUC (area under the curve; drug exposure) parameters within 80% to 125% of the reference parameter. The unit dosage forms of these embodiments are suited for oral administration (e.g., a tablet), and in certain embodiments, the unit dosage form is a coated tablet. Of course, it is understood by the skilled artisan that pharmacokinetic parameters can vary substantially depending on the subject (patient taking the drug) and that these values are representative of parameters obtained from a group of subjects, rather than from one individual.

Methods for Preparing Unit Dosage Forms

There are three general methods of tablet preparation: (1) the wet-granulation method; (2) the dry-granulation method; and (3) direct compression. These methods are well known to those skilled in the art. See, *Remington's Pharmaceutical Sciences,* 16th and 18th Eds., Mack Publishing Co., Easton, Pa. (1980 and 1990). See, also, *U.S. Pharmacopeia XXI*, U.S. Pharmacopeial Convention, Inc., Rockville, Md. (1985), or the *United States Pharmacopeia—National Formulary*, USP31-NF-25, The United States Pharmacopeia (USP), Rockville, Md. (2007).

In one embodiment, the substituted amphetamine tablets can be manufactured using a high shear wet granulation method, optionally incorporating pre-blending and pre-milling. Once granulated, the material can be dried, milled and blended again. The final powder blend can be compressed into tablets on a high-speed rotary press (or any other type of tablet press) and the resulting tablets coated in a perforated pan (or in a fluid bed coating apparatus).

Soft or hard gelatin capsules can be prepared that contain a mixture of the active pharmaceutical ingredient and vegetable oil or non-aqueous, water miscible materials such as, for example, polyethylene glycol and the like. Hard gelatin capsules may contain granules of the active pharmaceutical ingredient in combination with a solid, pulverulent carrier, such as, for example, lactose, saccharose, sorbitol, mannitol, potato starch, corn starch, amylopectin, cellulose derivatives, or gelatin.

Tablets are typically made by molding, by compression, or by generally accepted tablet forming methods. Accordingly, compressed tablets are usually prepared by large-scale production methods while molded tablets often involve small-scale operations.

In one specific embodiment, tablets for oral use are typically prepared in the following manner, although other techniques may be employed.

The solid substances are ground or sieved to a desired particle size, and the binding agent is homogenized and suspended in a suitable solvent. The active pharmaceutical ingredient and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size. The operating parameters of the machine may be selected by the skilled artisan.

Various tablet formulations may be made in accordance with the present invention. These include tablet dosage forms such as sugar-coated tablets, film-coated tablets, enteric-coated tablets, multiple-compressed tablets, prolonged action tablets and the like. Sugar-coated tablets (SCT) are compressed tablets that have a sugar coating applied to the surface of the tablets subsequent to tablet formation. Such coatings may be colored and are beneficial in masking drug substances possessing objectionable tastes or odors and in protecting materials sensitive to oxidation. Film-coated tablets (FCT) are compressed tablets that have a thin layer or film of a water-soluble (or insoluble) material applied to the surface of the tablets subsequent to tablet formation. A number of polymeric substances with film-forming properties may be used. The film coating imparts the same general characteristics as a sugar coating with the added advantage of a greatly reduced time period required for the coating operation. Enteric-coated tablets are also suitable for use in the present invention. Enteric-coated tablets (ECT) are compressed tablets coated with substances that resist dissolution in gastric fluid, but that disintegrate in the intestine. Enteric coating can be used for tablets containing drug substances that are inactivated or destroyed in the stomach, for drug substances that irritate the mucosa of the stomach, or as a means of delayed release of the medication.

Multiple compressed tablets (MCT) are compressed tablets made by more than one compression cycle, such as layered tablets or press-coated tablets. Layered tablets are prepared by compressing additional tablet granulation on a previously compressed granulation. The operation may be repeated to produce multilayered tablets of two, three, or more layers. Typically, special tablet presses are required to make layered tablets. See, for example, U.S. Pat. No. 5,213,738, which is incorporated by reference herein in its entirety.

Press coated tablets are another form of multiple compressed tablets. Such tablets, also referred to as dry-coated tablets, are prepared by feeding previously compressed tablets into a tabletting machine and compressing another granulation layer around the preformed tablets. These tablets have all the advantages of compressed tablets, i.e., slotting, monogramming, speed of disintegration, etc., while retaining the attributes of sugar coated tablets in masking the taste of the drug substance in the core tablet. Press-coated tablets can also be used to separate incompatible drug substances. Further, they can be used to provide an enteric coating to the core tablets. Both types of tablets (i.e., layered tablets and press-coated tablets) may be used, for example, in the design of prolonged-action dosage forms of the present invention.

In practical use, substituted amphetamine can be combined as the active pharmaceutical ingredient in intimate admixture with a pharmaceutically acceptable carrier according to conventional pharmaceutical compounding techniques. In preparing the compositions for oral dosage form, any of the usual pharmaceutical media or excipients may be employed. These include, for example, water, glycols, oils, alcohols, flavoring agents, preservatives, coloring agents, and the like, in the case of oral liquid preparations such as suspensions, elixirs and solutions; or aerosols; or excipients such as starches, sugars, microcrystalline cellulose, diluents, granulating agents, lubricants, binders, disintegrating agents, and the like, in the case of oral solid preparations such as powders, capsules, caplets, and tablets. Solid oral preparations are generally preferred over liquid ones, for a variety of reasons, including the enhanced stability often observed for APIs in solid preparations, as compared to liquid preparations. Because of their ease of administration, tablets and capsules represent the most advantageous oral dosage unit forms, in which case solid pharmaceutically acceptable excipients are obviously employed. If desired, tablets may be coated by standard aqueous or nonaqueous techniques. Preferred solid oral preparations are tablets and capsules.

Pharmaceutical stabilizers may be used to stabilize compositions comprising substituted amphetamine, or pharmaceutically acceptable salts, solvates, or prodrugs thereof.

In general, the compositions are prepared by uniformly and intimately admixing the active pharmaceutical ingredient with a liquid pharmaceutically acceptable carrier or a finely divided solid pharmaceutically acceptable carrier, or both, and then, if necessary, shaping the product into the desired presentation. For example, a tablet may be prepared by compression or molding, optionally with one or more accessory ingredients. Compressed tablets may be prepared by compressing in a suitable machine the active pharmaceutical ingredient in a free-flowing form such as powder or granules, optionally mixed with a binder, lubricant, inert diluent, disintegrating agent, and/or surface active or dispersing agent. Molded tablets may be made by molding in a suitable machine a mixture of the powdered compound moistened with an inert liquid diluent.

High Load, Low Impurity Formulations

The invention relates to the preparation of high drug load formulations, and processes of preparing high drug load formulations, having substituted amphetamine as the active ingredient and limited amounts of impurities. The inventors have discovered drug substance preparations of substituted amphetamine that allow for the production of substituted amphetamine unit dosage forms having 100 mg or more of API, excellent mechanical properties, therapeutically desirable dissolution and pharmacokinetic profiles, and limited amounts of impurities. The inventive formulations also allow for the production of tablets having 55% or more substituted amphetamine, by weight, yet having limited impurities. In particular, the invention relates to processes and drug substance preparations and processes useful in the preparation of such substituted amphetamine-containing unit dosage forms.

In a specific embodiment, substituted amphetamine-containing tablets can be manufactured using a high shear granulation method, optionally incorporating pre-blending and pre-milling. Once granulated, the material is dried, milled and blended again. The final powder blend (or composition) is then compressed into tablets on a high-speed rotary press and the resulting tablets are coated in a perforated pan. Bulk coated tablets are bulk-packed for shipping prior to intermediate packing for distribution to distribution centers or pharmacies, or final packaging for delivery to patients or patient caregivers.

Binders

Binders for solid pharmaceutical formulations include, but are not limited to, acacia, alginic acid, carbomer (e.g., carbopol), carboxymethylcellulose sodium, carrageenan, cellulose acetate phthalate, ceratonia, chitosan, confectioners sugar, cottonseed oil, dextrates, dextrin, dextrose, ethyl cellulose, gelatin, glucose, glyceryl behenate, guar gum, hydrogenated vegetable oil, hydroxyethyl cellulose, hydroxyethylmethyl cellulose, hydroxypropyl cellulose (e.g., Klucel®), hypromellose, hydroxypropyl methylcellulose (e.g., Methocel®), lactose, liquid glucose, magnesium aluminum silicate, maltodextrin, maltose, methylcellulose, microcrystalline cellulose, poloxamer, polydextrose, polyethylene oxide, polymethacrylates, povidone (e.g., Kollidon®, Plasdone®), pregelatinized starch, sodium alginate, starch, stearic acid, sucrose, sunflower oil, and zein.

Glidants

Glidants can be added to improve the flowability of a non-compacted solid formulation and to improve the accuracy of dosing. Excipients that may function as glidants include, but are not limited to, colloidal silicon dioxide, magnesium trisilicate, powdered cellulose, starch, talc and tribasic calcium phosphate. calcium silicate, magnesium silicate, magnesium trisilicate, and silicon dioxide.

Lubricants

When a dosage form such as a tablet is made by the compaction of a powdered formulation, the formulation is subjected to pressure from a punch and dye. Some excipients and active pharmaceutical ingredients have a tendency to adhere to the surfaces of the punch and dye, which can cause the product to have pitting and other surface irregularities. A lubricant can be added to the formulation to reduce adhesion and ease the release of the product from the dye. Lubricants include, but are not limited to, magnesium stearate, calcium stearate, glyceryl monostearate, glyceryl behenate, glyceryl palmitostearate, hydrogenated castor oil, hydrogenated vegetable oil, light mineral oil, magnesium lauryl sulfate, medium chain triglycerides, mineral oil, poloxamer, polyethylene glycol, sodium benzoate, sodium chloride, sodium lauryl sulfate, sodium stearyl fumarate, stearic acid, talc and zinc stearate.

Diluents

Examples of diluents include, but are not limited to, calcium carbonate, calcium phosphate, calcium sulfate, cellulose, cellulose acetate, compressible sugar, confectioner's sugar, dextrates, dextrin, dextrose, ethyl cellulose, fructose, fumaric acid, glyceryl palmitostearate, hydrogenated vegetable oil, kaolin, lactitol, lactose, magnesium carbonate, magnesium oxide, maltodextrin, maltose, mannitol, microcrystalline cellulose, polydextrose, polymethylacrylates, simethicone, sodium alginate, sodium chloride, sorbitol, starch, pregelantized starch, sterilizable maize, sucrose, sugar spheres, talc, tragacanth, trehalose, and xylitol.

Disintegrants

Examples of disintegrants include, but are not limited to, alginic acid, calcium phosphate, carboxymethyl cellulose calcium, croscarmellose, carboxymethyl cellulose sodium, powdered cellulose, chitosan, crospovidone, docusate sodium, guar gum, hydroxylpropyl cellulose, magnesium aluminum silicate, methylcellulose, povidone, sodium alginate, sodium starch glycolate, starch, and pregelantinized starch.

Salts

Examples of suitable pharmaceutically acceptable salts the API include, but are not limited to, aluminum, calcium, lithium, magnesium, potassium, sodium and zinc. In addition, organic salts may also be used including, but not limited to salts of lysine, N,N'-dibenzylethylenediamine, chloroprocaine, choline, diethanolamine, ethylenediamine, meglumine (N-methylglucamine), procaine and tromethamine.

Other Ingredients

Optional ingredients in the formulations of the invention include, but are not limited to, flavors, coloring agents, and stabilizers.

Flavoring agents and flavor enhancers make the dosage form more palatable to the patient. Common flavoring agents and flavor enhancers for pharmaceutical products that may be included in the formulation of the present invention include, but are not limited to, maltol, vanillin, ethyl vanillin, menthol, citric acid, fumaric acid, ethyl maltol and tartaric acid.

Solid and liquid formulations may also be dyed using any pharmaceutically acceptable colorant to improve their appearance and/or facilitate patient identification of the product and unit dosage level.

Definition: Degradation Product

As used herein, "degradation products" refers to the product(s) produced by decomposition of one or more of the active ingredients of the present compositions.

Experimental Introduction: Chiral Processes

The chiral process provides processes for the chiral synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursors using a modified organometallic compound such as a organocopper reagent, where the novel aryl or aryl-alkyl phosphoramidate precursor is then easily converted to the target compounds using known reactions, e.g. acidification, methylation of the nitrogen followed by dephosphorylation, etc.

In one preferred aspect of the chiral process the invention provides a synthetic pathway to amphetamine derivatives using an aziridine based process with an organometallic compound by heating the reactants in a first step, and then adding as a second step the Grignard reagent in a dosage controlled fashion. In a preferred embodiment of the chiral process, the reaction is heated to above 40 degrees C., preferably above about 45 degrees C., and more preferably above about 48 degrees C. In one embodiment, the temperature is maintained from 48-51 deg. C. for about 30 minutes and then brought to room temperature.

Dexamphetamine—Chiral

In another preferred embodiment of the chiral process, the invention provides a process of making the dexamphetamine, said process comprising:

providing a compound of Formula 5:

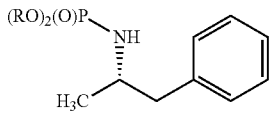

wherein R is alkyl or aryl; and deprotecting the compound of Formula 5 under acidic conditions effective to produce dexamphetamine of Formula I:

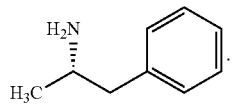

In preferred aspects of the chiral process, the dexamphetamine process comprises wherein the acidic conditions are aqueous hydrochloric, sulfuric or phosphoric acids.

In preferred aspects of the chiral process, the dexamphetamine process comprises wherein the aqueous acid water content is in an amount of 50% to 90%

In preferred aspects of the chiral process, the dexamphetamine process comprises wherein the R=methyl, ethyl, isopropyl or phenyl.

In preferred aspects of the chiral process, the dexamphetamine process comprises wherein said providing a compound of Formula 5 comprises:

providing a compound of Formula 4:

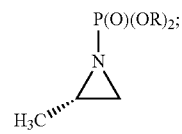

wherein R is alkyl or aryl and reacting the compound of Formula 4 with phenylmagnesium halide and a copper halide catalyst under solvent and temperature conditions effective to produce a compound of Formula 5 in a purity substantially free of any regioisomeric impurities.

In preferred aspects of the chiral process, the dexamphetamine process comprises wherein the regioisomeric purity of Formula 5 is >99% and the regioisomer is <0.1%.

In preferred aspects of the chiral process, the dexamphetamine process comprises wherein the R=methyl, ethyl, isopropyl or phenyl.

In preferred aspects of the chiral process, the dexamphetamine process comprises wherein the copper halide catalyst is CuCl, CuCl$_2$, CuBr or Copper nanoparticles.

In preferred aspects of the chiral process, the dexamphetamine process comprises wherein the solvent is an organic ether.

In preferred aspects of the chiral process, the dexamphetamine process comprises wherein the solvent is tetrahydrofuran or 2-methyltetrahydrofuran.

In preferred aspects of the chiral process, the dexamphetamine process comprises wherein said treating is carried out at a temperature of from about −10° C. to about 70° C.

In preferred aspects of the chiral process, the dexamphetamine process comprises wherein said treating is carried out at a temperature of from about 30° C. to about 60° C.

In preferred aspects of the chiral process, the dexamphetamine process comprises wherein said providing a compound of Formula 4 comprises:

providing a compound of Formula 3:

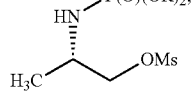

wherein R is alkyl or aryl; and reacting the compound of Formula 3 with the base under conditions effective to produce a compound of Formula 4.

In preferred aspects of the chiral process, the dexamphetamine process involving Formula 3 comprises a compound of Formula 3 wherein the R=methyl, ethyl, isopropyl or phenyl.

In preferred aspects of the chiral process, the dexamphetamine process comprises wherein the base is potassium hydroxide or potassium carbonate.

In preferred aspects of the chiral process, the dexamphetamine process comprises wherein said providing a compound of Formula 3 comprises:

providing a compound of Formula 2:

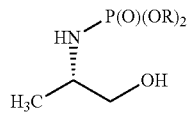

wherein R is alkyl or aryl; and reacting the compound of Formula 2 with methanesulfonyl chloride and a base under conditions effective to produce a compound of Formula 3.

In preferred aspects of the chiral process, the dexamphetamine process comprises a compound of Formula 2 wherein the R=methyl, ethyl, isopropyl or phenyl.

In preferred aspects of the chiral process, the dexamphetamine process comprises wherein said providing a compound of Formula 2 comprises:

providing a compound of Formula 1:

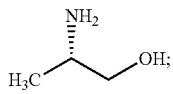

and reacting the compound of Formula II with the appropriate

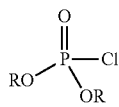

wherein R=alkyl or aryl under conditions effective to produce a compound of Formula 2.

In preferred aspects of the chiral process, the dexamphetamine process involving Formula 2 comprises wherein the R=methyl, ethyl, isopropyl or phenyl.

Dex-N-Methylamphetamine—Chiral

In another preferred embodiment of the chiral process, the invention provides a process of making the dex-N-methylamphetamine, said process comprising:

providing a compound of Formula 8:

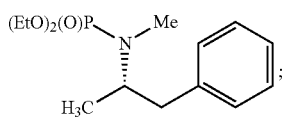

and deprotecting the compound of Formula 8 under acidic conditions effective to produce dex-N-methylamphetamine of Formula 9:

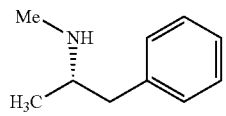

In preferred aspects of the chiral process, the dex-N-methylamphetamine process comprises wherein the acidic conditions are aqueous hydrochloric, sulfuric or phosphoric acids.

In preferred aspects of the chiral process, the dex-N-methylamphetamine process comprises wherein the aqueous acid water content is in an amount of 50% to 90%

In preferred aspects of the chiral process, the dex-N-methylamphetamine process comprises wherein said providing a compound of Formula 8 comprises:

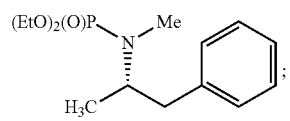

and reacting the compound of Formula 5b with a methyl alkylating agent and a base.

Dex-N-Ethylamphetamine—Chiral

In another preferred embodiment of the chiral process, the invention provides a process of making the dex-N-ethylamphetamine, said process comprising:

providing a compound of Formula 10:

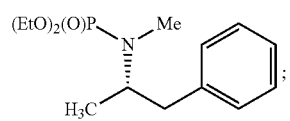

and deprotecting the compound of Formula 10 under acidic conditions effective to produce dex-N-ethylamphetamine of Formula 11:

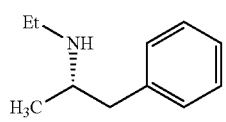

In preferred aspect of the chiral process, the dex-N-ethylamphetamine process comprises wherein the acidic conditions are aqueous hydrochloric, sulfuric or phosphoric acids.

In preferred aspects of the chiral process, the dex-N-ethylamphetamine process comprises wherein the aqueous acid water content is in an amount of 50% to 90%

In preferred aspects of the chiral process, the dex-N-ethylamphetamine process comprises wherein said providing a compound of Formula 10 comprises:

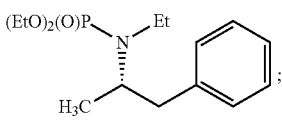

and reacting the compound of Formula 5b with a ethyl alkylating agent and a base In another preferred embodiment of the chiral process, the invention provides a compound of the formula:

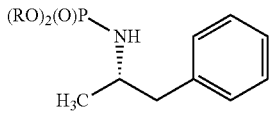

prepared according to one or more processes herein, in a regioisomeric purity of >1700:1
wherein:
R is alkyl or aryl In preferred aspects of the chiral process, the invention further comprises a compound of the formula:

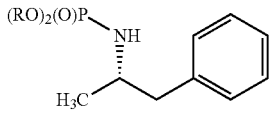

wherein the alkyl group is selected from the group consisting of methyl, ethyl or isopropyl In preferred aspects of the chiral process, the invention further comprises a compound of the formula:

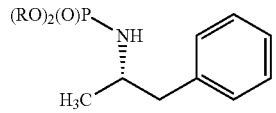

wherein the aryl group is phenyl.
Aziridine

In another preferred embodiment of the chiral process, the invention provides a compound of the formula:

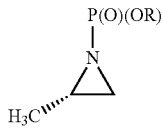

wherein: R is alkyl or aryl
In preferred aspects of the chiral process, the invention further comprises a compound of the formula:

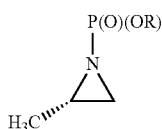

wherein the alkyl group is selected from the group consisting of methyl, ethyl or isopropyl.

In preferred aspects of the chiral process, the invention further comprises a compound of the formula:

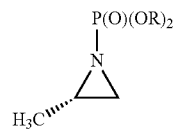

wherein the aryl group is phenyl.

General Process

In yet another preferred embodiment of the chiral process, there is provided a process for the synthesis of amphetamine derivatives comprising the step of performing a stereospecific cuprate addition reaction upon an aziridine phosphoramidate compound to obtain a chiral aryl or aryl-alkyl phosphoramidate amphetamine precursor.

Solvent Extraction

In yet another preferred embodiment of the chiral process, there is provided a process for solvent extraction of compounds 5a-d from a mixture of compounds 5a-d and 6a-d, comprising the step of performing a solvent extraction using a mixture of two or more solvents wherein at least one of the two or more solvents is THF.

Chiral Process Experimental Introduction

Unless otherwise noted, reagents and solvents were used as received from commercial suppliers.

NMR spectra: Proton nuclear magnetic resonance spectra were obtained on a Bruker AV 300 or a Bruker AV 500 spectrometer at 300 MHz and 500 MHz, respectively. Spectra are given in ppm ($\delta$) and coupling constants, J, are reported in Hertz. Tetramethylsilane was used as an internal standard for proton spectra.

HPLC analyses (achiral): Analyses were obtained on a Varian Prostar 210 HPLC system using a Prevail C18 column (53×7 mm, Alltech) with PDA detection at 208-210 nm and solvent gradient program Method A.

HPLC Method A:

| Time (min) | Flow (mL/min) | % A | % B |
|---|---|---|---|
| 0.0 | 2.0 | 95.0 | 5.0 |
| 10.0 | 2.0 | 5.0 | 95.0 |
| 11.5 | 2.0 | 5.0 | 95.0 |
| 11.6 | 2.0 | 95.0 | 5.0 |
| 13.0 | 2.0 | 95.0 | 5.0. |

A = Water with 0.05% v/v Trifluoroacetic Acid
B = Acetonitrile with 0.05% v/v Trifluoroacetic Acid HPLC analyses (chiral): Analyses were obtained on a Varian Prostar 210 HPLC system using a CR(−) CrownPak (150×4 mm, 5 um, Diacil Lot #CRMOCB-OK005) with PDA detection at 210-215 nm and isocratic solvent system Method B.

HPLC Method B
Flow rate: 0.7 mL/min
Run time: 35 min
Temp: ambient
Mobile phase: 90% water pH=1.5 (perchloric acid): 10% Methanol GC (FID): Analyses were obtained on a Varian CP 3800 GC using a Supleco (Cat #24048) SPB-5 30×0.320; 0.25 μm column.

Column temperature initial: 50° C.
Column temperature final: 275° C.
Ramp profile: 20.0 deg/min
Injector temperature: 250° C.
Detector temperature: 250° C.
Carrier Gas/flow rate: Helium, 2 mL/min Referring now to the following synthetic schemes, Chiral Scheme 1 provides:

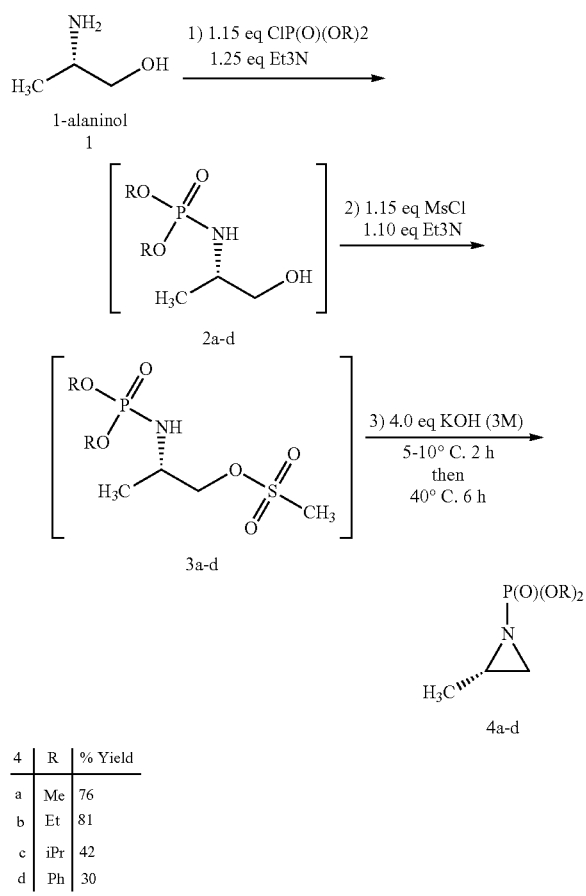

| 4 | R | % Yield |
|---|-----|---------|
| a | Me  | 76 |
| b | Et  | 81 |
| c | iPr | 42 |
| d | Ph  | 30 |

Chiral Process—Preparation of (S)-dimethyl (2-methylaziridin-1-yl)phosphonate (4a)

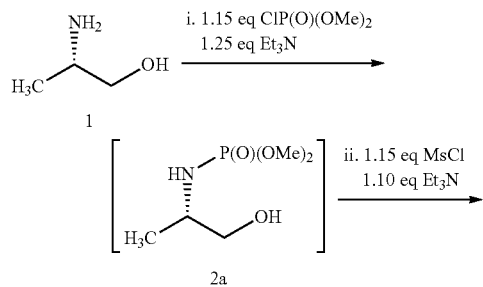

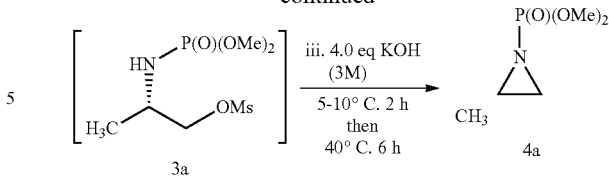

A 500 mL, 3-neck flask equipped with an overhead mechanical stirrer and pressure equalizing addition funnel was charged with L-alaninol (12.5 g, 166.4 mmol), triethylamine (29 mL, 208 mmol, 1.25 equiv) and dichloromethane (125 mL). The reaction solution was cooled to +2° C. and treated with dimethoxyphosphoryl chloride (20 mL, 183 mmol, 1.10 equiv) over 40 minutes while maintaining an internal temperature <+8° C. The reaction mixture was stirred with ice bath cooling for 1 hour at which point the reaction was complete by TLC analysis (silica gel, 93:6:1 DCM/MeOH/NH$_4$OH and 6/3/1 CHCl$_3$/MeOH/NH$_4$OH; KMnO$_4$ stain). Additional triethylamine (25.5 mL, 182.5 mmol, 1.10 equiv) was added to the reaction mixture and methanesulfonyl chloride (14.9 mL, 191 mol, 1.15 equiv) was added drop-wise over 45 minutes while maintaining an internal temperature <+10° C. The resulting reaction mixture was stirred with ice bath cooling for 1.0 hour after which time TLC analysis indicated the reaction was complete. Potassium hydroxide solution (3 M, 220 mL, 650 mmol, 4.0 equiv) was slowly added to the stirred reaction mixture while maintaining an internal temperature <+16° C. The reaction was continued with agitation for 6 hours, after which time the aqueous layer was separated and discarded. Saturated NaHCO$_3$ solution (35 mL) was added and the biphasic mixture heated to 40-42° C. Distillation was started and a first fraction of 90 mL of dichloromethane was collected. When the temperature reached 50° C., a second fraction was collected until the batch temperature was 65° C. The mixture was heated at 65° C. for another 1 hour and then cooled to ambient temperature. Dichloromethane (90 mL) was added and the mixture stirred for 10 minutes before separation. The dichloromethane layer was concentrated under reduced pressure. The residue was dissolved in heptanes (15 mL) and concentrated under reduced pressure to remove the residual water. This azeotropic drying was repeated two more times. The resulting 4a was obtained as a light yellow liquid (20.9 g, 76% yield, 95.40% GC purity). A colorless sample was prepared by short path distillation (80-85° C. @ 15 mm Hg vacuum). Optical rotation c=1.00, ethanol, 25.0° C., +39.3°. $^1$H NMR (300 MHz, CDCl$_3$) δ 3.80 (s, 3H), 3.76 (s, 3H), 2.65-2.50 (m, 1H), 2.42-2.31 (m, 1H), 1.92 (dt, J=3.6, 1.2 Hz, 1H), 1.28 (dd, J=5.4, 1.2 Hz, 3H).

Chiral Process—Preparation of (S)-diethyl (2-methylaziridin-1-yl)phosphonate (4b)

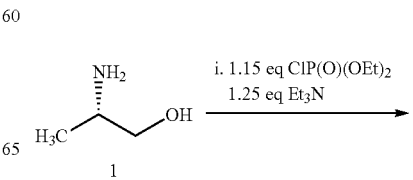

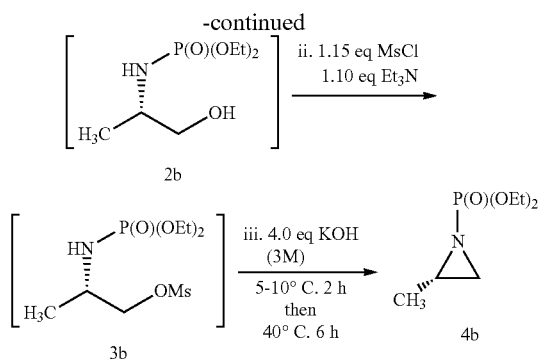

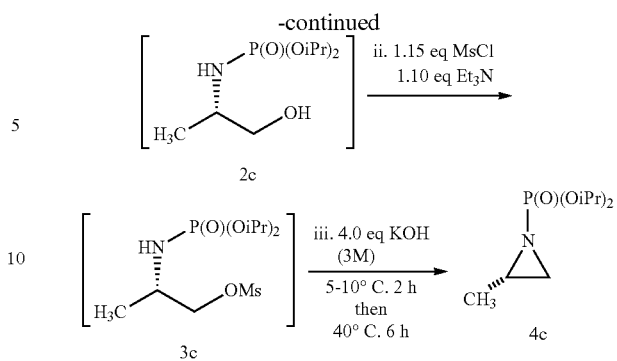

A 12 L 3-neck flask fitted with an overhead mechanical stirrer and 1 L pressure equalizing addition funnel was charged with L-alaninol (250.0 g, 3.33 mol), triethylamine (578 mL, 4.16 mol, 1.25 equiv) and dichloromethane (2.5 L). The stirred solution was cooled to +2° C. and diethoxyphosphoryl chloride (531 mL, 3.661 mol, 1.10 equiv) was added over 1.5 hour while maintaining an internal temperature <+8° C. The reaction mixture was stirred an additional 1 hour at which point the reaction was complete by TLC analysis (silica gel plate, 93:6:1 dichloromethane/MeOH/NH$_4$OH and 6/3/1 CHCl$_3$/MeOH/NH$_4$OH; KMnO$_4$ stain). Additional triethylamine (510 mL, 3.65 mol, 1.10 equiv) was added to the reaction mixture and methanesulfonyl chloride (297 mL, 3.82 mol, 1.15 equiv) was added dropwise over 1.5 hours while maintaining an internal temperature <+10° C. The resulting reaction mixture was stirred for 1.5 hours at which time TLC analysis (see above methods) indicated the reaction was complete. Potassium hydroxide solution (3 M solution, 4.40 L, 13 mol, 4.0 equiv) was slowly added to the stirred reaction mixture while maintaining an internal temperature <+16° C. The reaction was stirred for 6 hours, after which time the aqueous layer was separated. Saturated NaHCO$_3$ solution (700 mL) was added and the biphasic mixture was heated to 40-42° C. Distillation was started and a first fraction of 1.8 L of dichloromethane was collected. When the batch temperature reached 50° C., a second fraction was collected until the batch temperature was 65° C. The mixture was heated at 65° C. for another 1 hour and then cooled to ambient temperature. Dichloromethane (1.8 L) was added and the mixture stirred for 10 minutes before separation. The organic layer was concentrated under reduced pressure and heptane (250 mL) was added to the concentrate. The resulting mixture was concentrated under reduced pressure. The resulting 4b was obtained as a light yellow liquid (518.5 g, 80.6% yield, 98.90% GC purity). A colorless sample was prepared by short path distillation at 66-67° C., 0.9 mm Hg. Optical rotation c=1.01, ethanol, 22.5° C., +28.8°. $^1$H NMR (300 MHz, CDCl$_3$) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Chiral Process—Preparation of (S)-diisopropyl (2-methylaziridin-1-yl)phosphonate (4c)

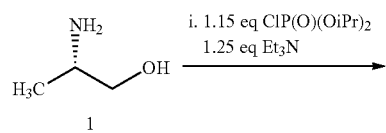

A 250 L, 3-neck flask fitted with an overhead mechanical stirrer and pressure equalizing addition funnel was charged with L-alaninol (4.2 g, 55.7 mmol), triethylamine (9.74 mL, 69.68 mmol, 1.25 equiv) and dichloromethane (50 mL). The stirred reaction solution was cooled to +2° C. and diisopropylphosphoryl chloride (12.3 g, 61.3 mmol, 1.10 equiv) was added drop-wise over 1.3 hours maintaining an internal temperature <+8° C. The reaction mixture was stirred at about 0° C. for 10 hours. At this point, the reaction was complete by TLC analysis (silica gel, 93:6:1 DCM/MeOH/NH$_4$OH and 6/3/1 CHCl$_3$/MeOH/NH$_4$OH; KMnO$_4$ stain). Additional triethylamine (8.6 mL, 61.3 mmol, 1.10 equiv) was added to the reaction mixture and methanesulfonyl chloride (4.96 mL, 64.1 mmol, 1.15 equiv) was added over 1.5 hours maintaining an internal temperature <+10° C. The resulting reaction mixture was stirred at about 0° C. for 1.5 hours after which time TLC analysis (see above) indicated the complete consumption of 2c and formation of 3c. Potassium hydroxide solution (3 M solution, 74 mL, 222.9 mmol, 4.0 equiv) was slowly added to the stirred reaction mixture while maintaining an internal temperature <+16° C. The reaction was continued with agitation for 6 hours, after which time the layers were separated. The organic layer was washed with 10% citric acid solution (40 mL) and saturated NaCl solution (2×40 mL). The organic layer was concentrated under reduced pressure and the residue was distilled (bulb-to-bulb; 79-82° C. @ 3 mm Hg vacuum) to afford 4c as a clear colorless liquid (5.2 g, 42.0% yield, 97.0% GC AUC purity). Optical rotation c=1.01, ethanol, 22.5° C., +28.8°. $^1$H NMR (300 MHz, CDCl$_3$) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H), 1.22 (dd, J=5.6, 1.2 Hz, 3H).

Chiral Process—Preparation of (S)-diphenyl (2-methylaziridin-1-yl)phosphonate (4d)

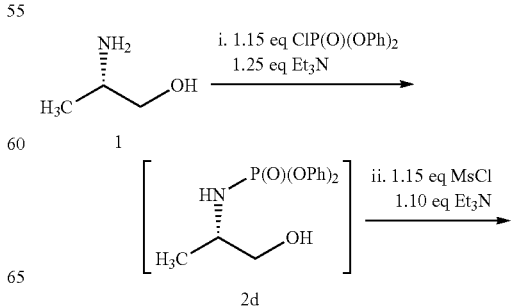

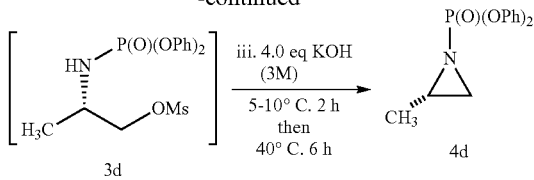

A 500 L 3-neck flask fitted with an overhead mechanical stirrer and a pressure equalizing addition funnel was charged L-alaninol (8.5 g, 113 mmol), triethylamine (19.5 mL, 139.36 mmol, 1.25 equiv) and dichloromethane (100 mL). The stirred reaction mixture was cooled to +2° C. and treated with diphenylchlorophosphate (33.4 g, 124.3 mmol, 1.10 equiv) over 1 hour while maintaining an internal temperature <+8° C. The reaction mixture was stirred for 10 hours at which point the reaction was complete by TLC analysis (silica gel, 93:6:1 DCM/MeOH/NH$_4$OH and 6/3/1 CHCl$_3$/MeOH/NH$_4$OH; KMnO$_4$ stain). Additional triethylamine (17.5 mL, 123 mmol, 1.10 equiv) was added to the reaction mixture and methanesulfonyl chloride (10 mL, 129.1 mmol, 1.15 equiv) was added over 50 minutes while maintaining an internal temperature <+10° C. The resulting reaction mixture was stirred with ice bath cooling for 1.5 hours after which time TLC analysis (see above) indicated the reaction was complete. Potassium carbonate (61.5 g, 445 mmol, 4.0 equiv) was added to the cooled, stirred reaction mixture while maintaining an internal temperature <+16° C. The reaction mixture was stirred for 6 hours at ambient temperature. The solid was filtered and the organic phase was washed with 10% citric acid solution (40 mL) and saturated NaCl solution (2×40 mL). The organic solution was concentrated under reduced pressure and the residue was purified by column chromatography. The resulting 4d was obtained as viscous oil (9.8 g, 30.0% yield, 97.0% GC purity). Optical rotation c=1.00, ethanol, 25.1° C., +34.8°. $^1$H NMR (300 MHz, CDCl$_3$) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H), 1.22 (dd, J=5.6, 1.2 Hz, 3H).

Referring now to the following chiral synthetic scheme, Chiral Scheme 2 provides:

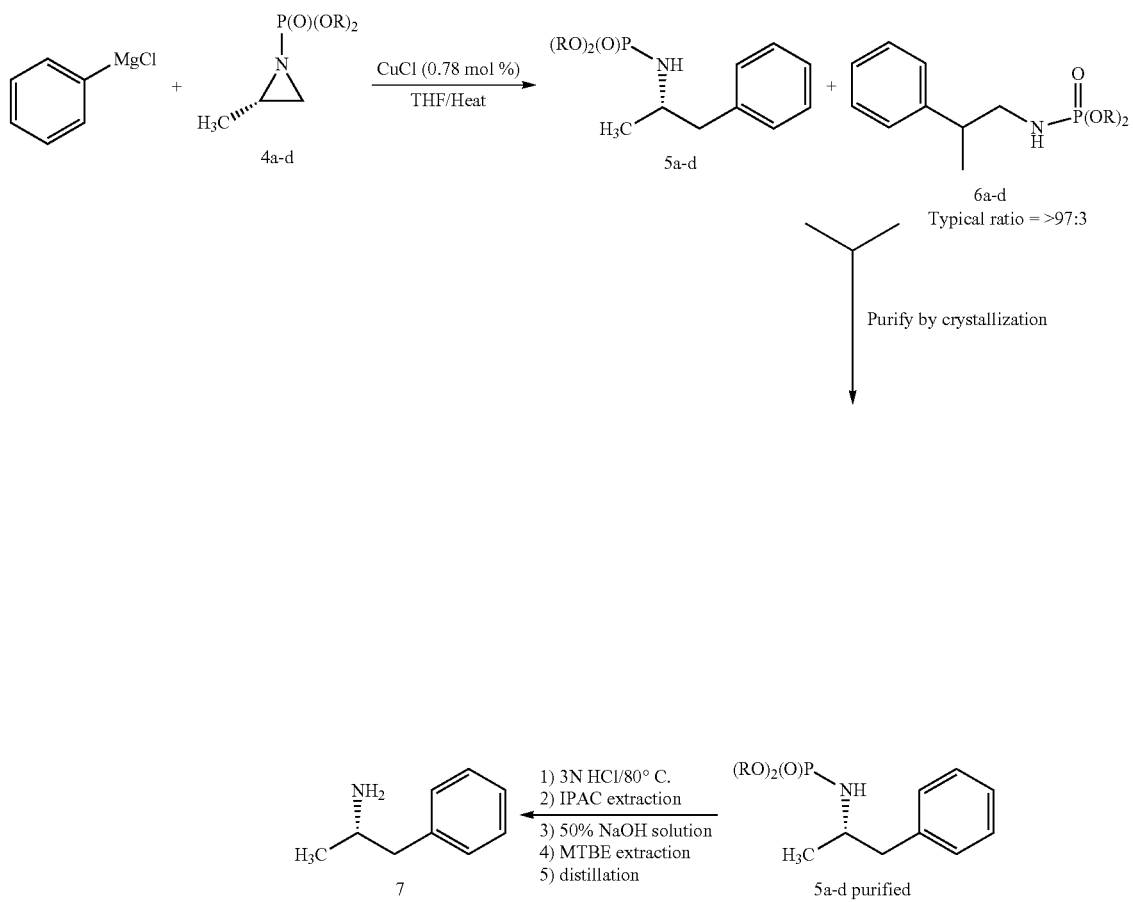

The phosphoryl chlorides were either purchased or prepared as per Posheus, Herweh, J. Am. Chem. Soc. 1957, 79, 6127-6129.

Chiral Process—Preparation of (S)-dimethyl (1-phenylpropan-2-yl)phosphoramidate (5a)

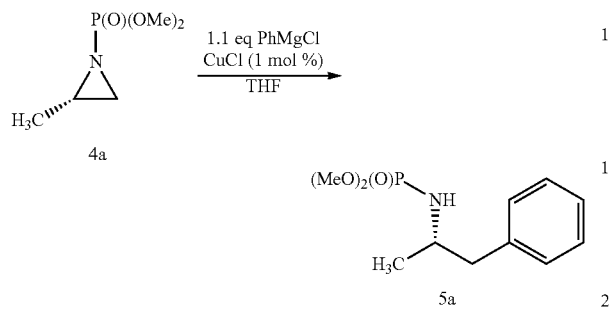

A 100 mL 3-neck flask was charged with 4a (4.0 g, 24.2 mmol), THF (25 mL) and CuCl (28 mg, 1 mol %) and the stirrer was started. The mixture was heated to 48° C. A pressure equalizing addition funnel was charged with PhMgCl (2M in THF, 13 mL) and the solution was added slowly while maintaining an internal temperature between 48-51° C. The reaction was stirred at 48-51° C. for an additional 30 minutes and then cooled to ambient temperature. The reaction was quenched by slow addition to a cooled (15° C.) solution of saturated aqueous ammonium chloride in water (50/50 v/v, 40 mL) while maintaining the temperature below 20° C. Heptanes (40 mL) was used to rinse the reactor and the rinse solution was transferred to the quenched reaction mixture. The mixture was agitated for 5 minutes, allowed to separate for 20 minutes then the aqueous phase was discarded. The organic phase washed with deionized water (10 mL) and the organic phase concentrated under reduced pressure to give an oil. The residue was dissolved in heptanes (50 mL) and the solution was concentrated under reduced pressure. The residue was crystallized from methyl tert-butyl ether (1 g/3 mL), filtered and dried to give 5a as white needles (3.29 g; 60.2% yield), with 99.89% GC purity containing 0.05% 6a. mp 86-88° C. Optical rotation c=1.00, ethanol, 25.0° C., +29.7° 0.1H NMR (300 MHz, CDCl$_3$) δ 7.32-7.17 (m, 5H), 3.66 (d, J=6.4 Hz, 3H), 3.50-3.83 (m, 1H), 2.71 (d, J=6.6 Hz, 2H), 2.45 (m, 1H), 1.15 (d, J=6.6 Hz, 3H).

Chiral Process—Preparation of Dexamphetamine (7) from 5a

A 50 mL flask was charged with 5a (4.80 g, 19.73 mmol) and 3 M HCl (15.0 mL) and the stirred reaction mixture was heated to 80° C. for 1 hour, then cooled to room temperature. The reaction mixture was washed with isopropyl acetate (2×20 mL) and the organic extracts were disposed. The aqueous layer was treated with sodium hydroxide solution (50%, 12.0 mL) keeping the internal temperature below 25° C. Methyl tert-butyl ether (15 mL) was added and the reaction mixture was agitated for 5 minutes then allowed to separate. The organic layer washed with water (10 mL) and concentrated under reduced pressure to give 7 as a colorless oil (2.51 g, 94.4% yield, >99.5% purity by GC and chiral HPLC).

Chiral Process—Preparation of (S)-diethyl (1-phenylpropan-2-yl) phosphor-amidate (5b)

A 12 L, jacketed, bottom outlet flask was charged with 4b (500 g, 2.58 mol), THF (2.5 L) and CuCl (2.0 g, 0.78 mol %) and the stirred mixture was heated to 46° C. A pressure equalizing addition funnel was charged with PhMgCl (2M in THF, 1.6 L) and the solution was added slowly while maintaining an internal temperature between 48-51° C. After the addition was complete, the reaction mixture was stirred at 48-51° C. for an additional 30 minutes and then cooled to ambient temperature. The reaction was quenched by slow addition to a cooled mixture of saturated aqueous ammonium chloride solution and water (50/50 v/v, 3.0 L) while maintaining an internal temperature below 20° C. The flask was rinsed with heptanes (2.0 L) and the rinse was transferred to the quenched reaction mixture. The biphasic mixture was stirred for 5 minutes, allowed to separate for 20 minutes and then the aqueous phase was removed. The organic phase washed with deionized water (500 mL) and the organic phase concentrated under vacuum to a volume of about 1.0 L. Heptanes (1000 mL) was added and the solution volume was adjusted by reduced pressure distillation to a total volume of about 1.5 L. The stirrer was slowed and the crystallization was allowed to proceed for about 24 hours. The slurry was cooled to 5° C. for about 1.5 hours. The resulting crystalline solid was collected by vacuum filtration and washed with cold heptanes (2×200 mL). After drying under vacuum at 35° C. for 48 hours the (S)-diethyl (1-phenylpropan-2-yl)phosphoramidate (5b) was obtained as a white crystalline solid (565.0 g, 80.5% yield; 99.66% GC purity with 0.04% 6b present). mp 64-65° C. Optical rotation c=1.10, ethanol, 22.5° C., +27.7°. $^1$H NMR (300 MHz, CDCl$_3$) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

Chiral Process—Alternate Preparation of (S)-diethyl (1-phenylpropan-2-yl)phosphoramidate (5b) Using Cu Nanoparticles

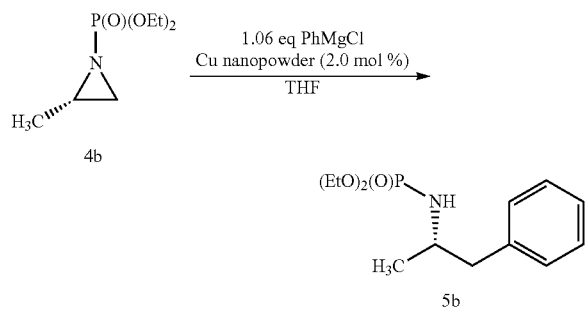

A 250 mL 3-necked flask was charged with 4b (10 g, 51.8 mmol), THF (50 mL) and copper nanopowder (65 mg, 2 mol %) and the stirred mixture was heated to 50° C. A pressure equalizing addition funnel was charged with PhMgCl (2M in THF, 29 mL) and the reagent was added while maintaining an internal temperature of 50-52° C. The reaction was allowed to stir at 50-52° C. for an additional 16 hours and then cooled to ambient temperature. The reaction was quenched by slow addition to a cooled (15° C.) solution of saturated aqueous ammonium chloride/water (50/50 v/v, 50 L) while maintaining an internal temperature below 20° C. Heptanes (50 L) was used to rinse the reactor and this rinse was transferred to the quenched mixture. The mixture was agitated for 5 minutes, allowed to separate and the aqueous phase was removed. The organic phase washed with deionized water (50 mL) and the organic phase concentrated under reduced pressure to a volume of about 15 mL. Heptanes (50 mL) were added and the solution was evaporated under reduced pressure volume to a total volume of about 15 mL. The solution was slowly stirred for about 24 hours affording a white slurry which was cooled to 5° C. for about 1.5 hours. The resulting crystalline solid was collected by filtration and washed with cold heptanes (2×10 mL). After drying under reduced pressure at 35° C. for 48 hours, 5b was obtained as a white crystalline solid (8.6 g, 60.5% yield, 99.90% GC purity).

Chiral Process—Alternate Preparation of (S)-diethyl (1-phenylpropan-2-yl)phosphoramidate (5b) Using Cu(II) chloride

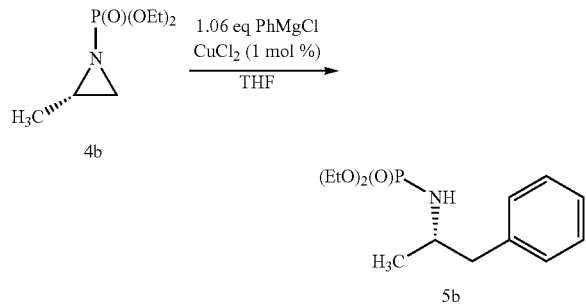

A 250 mL 3-neck flask was charged with 4b (10 g, 51.8 mol), THF (50 mL) and CuCl$_2$ (70 mg, 1 mol %) after which time the mixture was heated to about 50° C. A pressure equalizing addition funnel was charged with PhMgCl (2M in THF, 29 mL) and the reagent was added slowly while maintaining an internal temperature between 50-52° C. The reaction was allowed to stir at 50-52° C. for an additional 16 hours and then cooled to ambient temperature. The reaction was quenched by slow addition to a cooled (about 15° C.) solution of saturated aqueous ammonium chloride/water (50/50 v/v, 50 mL) while maintaining an internal temperature below 20° C. Heptanes (50 mL) was used to rinse the reactor and was transferred to the quench mixture, the mixture was agitated for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution was concentrated under reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 48 h, 5b was obtained as a white crystalline solid (8.7 g, 60.0% yield, 99.90% GC purity).

Chiral Process—Alternate Preparation of (S)-diethyl (1-phenylpropan-2-yl)phosphoramidate (5b) Using CuBr

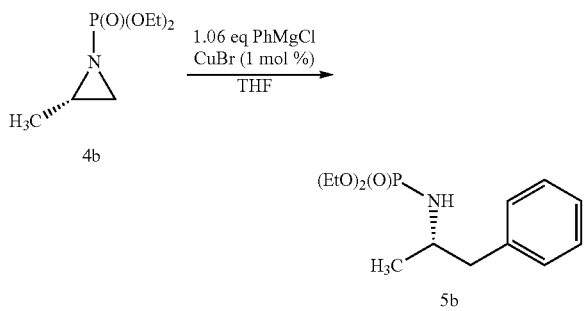

A 250 mL 3-neck flask was charged with 4 (10 g, 51.8 mol), THF (50 mL) and CuBr (74.4 mg, 1 mol %) after which time the mixture was heated to about 50° C. A pressure equalizing addition funnel was charged with PhMgCl (2M in THF, 29 mL) and the reagent was added slowly while maintaining an internal temperature between 48-52° C. The reaction was allowed to stir at 50-52° C. for an additional 16 hours and then cooled to ambient temperature. The reaction was quenched by slow addition to a cooled (about 15° C.) solution of saturated aqueous ammonium chloride/water (50/50 v/v, 50 mL) while maintaining an internal temperature below 20° C. Heptanes (50 mL) was used to rinse the reactor and was transferred to the quench mixture. The mixture was stirred for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution was adjusted by reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 48 h, 5b was obtained as a white crystalline solid (9.1 g, 65% yield, 99.90% GC purity).

The use of other copper salts (CuF, Cu(OAc)₂, Cu(acac)₂, Cu(OMe)₂ and Copper turnings) in conversion to 4b to 5b, conducted under the established procedure afforded 5b in comparable isolated yield, GC purity and devoid of the regioisomer 6b.

Chiral Process—Alternate Preparation of (S)-diethyl (1-phenylpropan-2-yl)phosphoramidate (5b) in THF-toluene Mixture

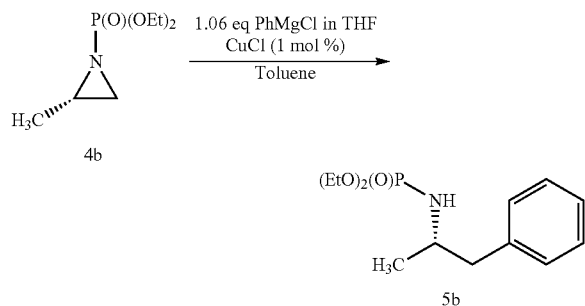

A 250 mL 3-neck flask was charged with 4b (10 g, 51.8 mol), toluene (50 mL) and CuCl (51 mg, 1 mol %) after which time the mixture was heated to about 50° C. A dropping addition funnel was charged with PhMgCl (2M in THF, 29 mL) and the reagent was added slowly while maintaining an internal temperature between 48-52° C. The reaction was allowed to stir at 50-52° C. for an additional 16 hours and then cooled to ambient temperature. The reaction was quenched by slow addition to a cooled (15° C.) solution of saturated aqueous ammonium chloride/water (50/50 v/v, 50 mL) while maintaining an internal temperature below 20° C. Heptanes (50 mL) was used to rinse the reactor and was transferred to the quench mixture, the mixture was agitated for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution volume was adjusted by reduced pressure to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 36 hours, 5b was obtained as a white crystalline solid (8.7 g, 62% yield, 99.92% GC purity).

Chiral Process—Alternate Preparation of (S)-diethyl (1-phenylpropan-2-yl)phosphoramidate (5b) in THF-methyl tert-butyl ether Mixture

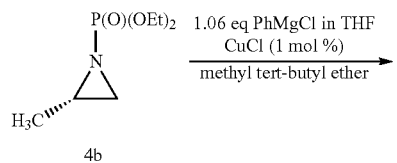

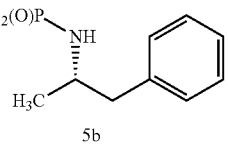

A 250 mL 3-neck flask was charged with 4 (10 g, 51.8 mol), methyl tert-butyl ether (50 mL) and CuCl (51 mg, 1 mol %) after which time the mixture was heated to about 50° C. A pressure equalizing addition funnel was charged with PhMgCl (2M in THF, 29 mL) and the reagent was added slowly while maintaining an internal temperature between 48-52° C. The reaction was allowed to stir at 50-52° C. for an additional 16 hours and then cooled to ambient temperature. The reaction was quenched by slow addition to a cooled (15° C.) solution of saturated aqueous ammonium chloride/water (50/50 v/v, 50 mL) while maintaining an internal temperature below 20° C. Heptanes (50 mL) was used to rinse the reactor and was transferred to the quench mixture. The mixture was agitated for 5 minutes, allowed to separate for 20 minutes and then the aqueous phase was removed. The organic phase washed with deionized water (50 mL) and the organic phase concentrated under reduced pressure to a volume of about 15 mL. Heptanes (50 mL) was added and the solution volume was adjusted by reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 24 hours, 5b was obtained as a white crystalline solid (8.8 g, 63% yield, 99.93% GC purity).

Chiral Process—Alternate Preparation of (S)-diethyl (1-phenylpropan-2-yl)phosphoramidate (5b) in THF-2 methyl THF Mixture

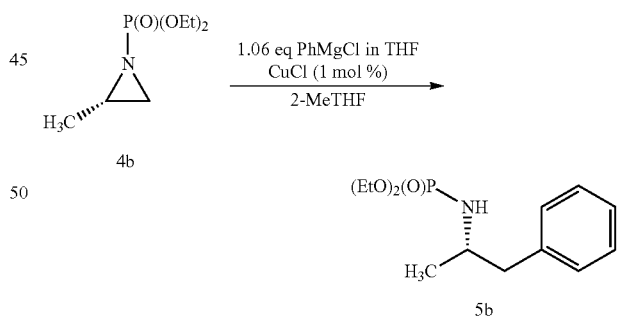

A 250 mL 3-neck flask was charged with 4 (10 g, 51.8 mol), 2-MeTHF (50 mL) and CuCl (51 mg, 1 mol %) after which time the mixture was heated to about 50° C. A pressure equalizing addition funnel was charged with PhMgCl (2M in THF, 29 mL) and the reagent was added slowly while maintaining an internal temperature between 48-52° C. The reaction was allowed to stir at 50-52° C. for an additional 12 hours and then cooled to ambient temperature. The reaction was quenched by slow addition to a cooled (15° C.) solution of saturated aqueous ammonium chloride/water (50/50 v/v, 50 mL) while maintaining an internal temperature below 20° C. Heptanes (50 mL) was used to rinse the reactor and was transferred to the quench mixture. The mixture was agitated for 5 minutes, allowed to separate for 20 minutes then the aqueous phase was removed. The organic phase washed with deionized water (50 mL) and the organic phase concentrated under reduced pressure to a volume of about 15 mL. Heptanes (50 mL) was added and the solution volume was adjusted by reduced pressure distillation to a total volume of about 15 mL. The solution was slowly stirred for 24 hours at ambient temperature to afford a white slurry which was then cooled to 5° C. for about 1.5 hours. The resulting crystalline solid was collected by filtration and washed with cold heptanes (2×10 mL). After drying under vacuum at 35° C. for 24 hours, 5b was obtained as a white crystalline solid (9.1 g, 65% yield, 99.89% GC purity).

Chiral Process—Preparation of Dexamphetamine (7) from 5b

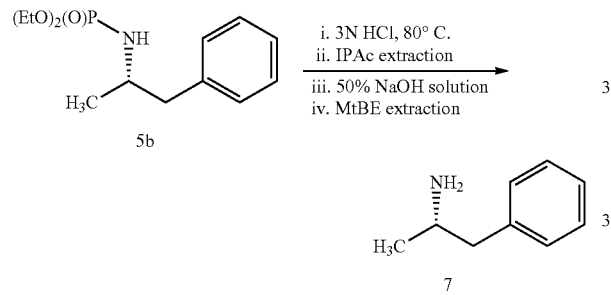

A 2 L, jacketed, bottom outlet valve flask was charged with 5b (209 g, 0.770 mol) and 3 M hydrochloric acid (510 mL) and the reaction mixture was heated to 80° C. for 1.5 hours and then cooled to room temperature. The orange solution was extracted with isopropyl acetate (500 mL) and the organic extract layer was discarded. Sodium hydroxide solution (50%, 175 mL) was slowly added to the remaining aqueous layer, keeping the internal temperature below 25° C. Methyl tert-butyl ether (200 mL) was added and the reaction mixture was agitated for 20 minutes then allowed to separate for 30 minutes. The aqueous layer was removed and the organic layer washed with water (100 mL) and concentrated under reduced pressure to afford a light brown oil. This oil was distilled (Distillation conditions: 1" wipe film still, T=65-90° C., vacuum=4-5 mmHg, wiper speed=490-520 rpm.) to give dexamphetamine (7) as a clear colorless oil (81 g, 78% yield; >99.8% pure by GC). Chiral HPLC analysis: 99.83% dextroampehtamine; 0.16% levoamphetamine; 99.67% ee. Optical rotation c=2.0, methanol, 22.0° C., +29.2°. $^1$H NMR (300 MHz, CDCl$_3$) δ 7.36-7.26 (m, 2H), 7.23-7.13 (m, 3H), 3.26-3.03 (m, 11H), 2.72 (dd, J=13.2, 5.4 Hz, 11H), 2.53 (dd, J=13.2, 8.0 Hz, 1H), 1.20 (br s, 2H), 1.13 (d, J=6.3 Hz, 3H).

Chiral Process—Preparation of (S)-diisopropyl (1-phenylpropan-2-yl)phosphoramidate (5c)

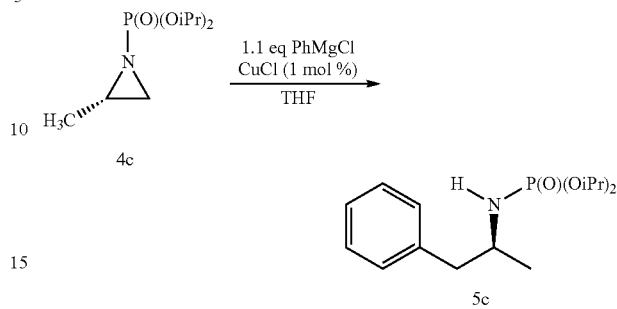

A 100 mL jacketed flask equipped with an overhead stirrer was charged with 4c (5.0 g, 22.6 mmol), THF (25 mL) and CuCl (23 mg, 1 mol %). The stirrer was started and the mixture was heated to 48° C. A pressure equalizing addition funnel was charged with PhMgCl (2M in THF, 12.4 mL) and this solution was added while maintaining the internal temperature of 48-51° C. The reaction was allowed to stir at 48-51° C. for 30 minutes after Grignard addition and then cooled to 20° C. The reaction was quenched by slow addition to a pre-cooled (15° C.) solution of saturated aqueous ammonium chloride solution in water (50/50 v/v, 40 mL) while maintaining an internal temperature below 20° C. Heptanes (40 mL) was used to rinse the reactor and the rinse solution was added to the quench mixture. The mixture was agitated for 5 minutes, allowed to separate for 20 minutes and then the aqueous phase was removed. The organic phase washed with deionized water (10 mL) and the organic phase concentrated under reduced pressure. The residue was dissolved in heptanes (50 mL) and the solution was concentrated to dryness under reduced pressure. The residue was purified by chromatography (120 g Combiflash Gold column eluting with 100% dichloromethane to 5% MeOH in dichloromethane over a 40 minute gradient). The appropriate fractions were concentrated to dryness under reduced pressure to give the desired product as a slow crystallizing solid (4.4 g, 65%, 92% GC purity). The GC analysis indicated the presence of 5% biphenyl as well as ~0.8% of 6c. A 1 g sample was removed and crystallized from 1 volume cold heptanes at −15° C. The resulting crystals of 5c (0.421 mg, 42% recovery) were found to be 99.75% pure by GC analysis with 0.09% of 6c. The crystalline 5c melted when the sample reached room temperature. Optical rotation c=1.10, ethanol, 22.5° C., +27.7°. $^1$H NMR (300 MHz, CDCl$_3$) δ 7.32-7.17 (m, 5H), 4.59-4.41 (m, 2H), 3.53-3.41 (m, 1H), 2.86-2.80 (m, 1H), 2.69-2.61 (m, 1H), 2.36 (t, J=9.6 Hz, 1H), 1.32-1.26 (m, 12H), 1.08 (d, J=10.1 Hz, 3H).

Chiral Process—Preparation of Dexamphetamine (7) from 5c

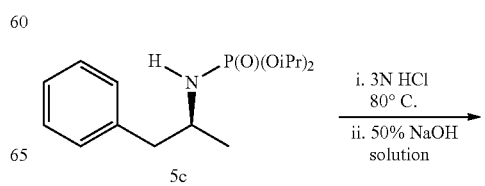

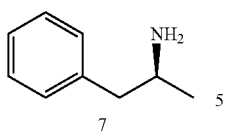

7

A 50 mL flask was charged with 5c (3.54 g, 11.82 mmol) and 3 M HCl (8.7 mL) and the stirred reaction mixture was heated to 80° C. for 12 hours, then cooled to room temperature. The aqueous solution was washed with isopropyl acetate (2×20 mL) and the organic extract was discarded. The aqueous layer was treated with sodium hydroxide solution (50%, 3.0 mL) keeping the internal temperature below 25° C. Methyl tert-butyl ether (40 mL) was added and the reaction mixture was agitated for 5 minutes then allowed to separate for 15 minutes. The aqueous layer was extracted with methyl tert-butyl ether (40 mL) and the combined organic layers were washed with water (10 mL) and concentrated under reduced pressure to give 7 as a colorless oil (1.28 g, 80.3% yield, >98.7% purity by GC and chiral HPLC).

Chiral Process—Preparation of (S)-diphenyl (1-phenylpropan-2-yl) phosphoramidate (5d)

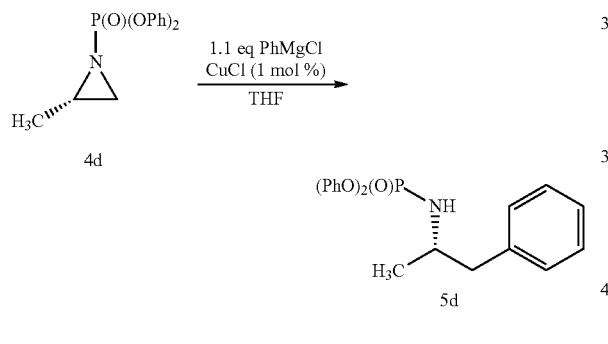

A 100 mL jacketed flask was charged with 4d (5.0 g, 17.3 mmol), THF (25 mL) and CuCl (21 mg, 1 mol %) and the stirred mixture was heated to 48° C. A pressure equalizing addition funnel was charged with PhMgCl (2M in THF, 8.7 mL) and the solution was added slowly while maintaining a reaction temperature of 48-51° C. The reaction was allowed to stir at 48-51° C. for an additional 30 minutes and then cooled to ambient temperature. The reaction was quenched by slow addition to a cooled (15° C.) solution of saturated aqueous ammonium chloride/water mixture (50/50 v/v, 30 mL) while maintaining the batch temperature below 20° C. Heptanes (30 mL) was used to rinse the reactor and was transferred to the quench mixture. The mixture was agitated for 5 minutes and the aqueous layer was removed. The organic layer washed with deionized water (8 mL) and the organic phase concentrated under reduced pressure to give an oil. This residue was dissolved in heptanes (30 mL) and the solution was concentrated under reduced pressure to afford a residue. The residue was crystallized from ethanol (1 g/5 mL) to give 5d as a white solid (3.14 g, 50% yield, 99.65% GC purity containing 0.05% of 6d). mp 102-103° C. (lit 101-102° C.). Optical rotation c=1.00, ethanol, 25.0° C., +18.4° 0.1H NMR (300 MHz, CDCl$_3$) δ 7.38-7.11 (m, 15H), 3.83-3.65 (m, 1H), 3.00-2.89 (m, 1H), 2.86-2.78 (m, 1H), 2.73-2.62 (m, 1H), 1.15 (d, J=10.1 Hz, 3H).

Chiral Process—Preparation of Dexamphetamine (7) from 5d

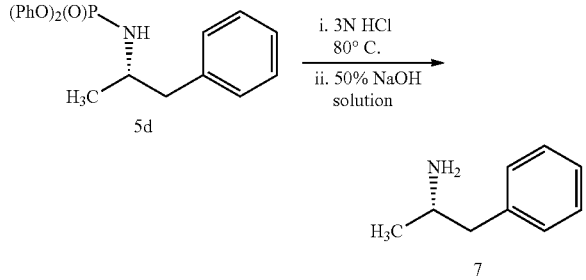

A 50 mL flask was charged with 5d (7.24 g, 19.71 mmol) and 3 M HCl (15.0 mL) and the stirred reaction mixture was heated to 80° C. for 32 hours, at which point it was cooled to room temperature. The organic layer was washed with isopropyl acetate (2×20 mL) and the organic extracts were discarded. The aqueous layer was treated with sodium hydroxide solution (50%, 3.0 mL) keeping the internal temperature below 25° C. Methyl tert-butyl ether (40 mL) was added and the reaction mixture was agitated for 5 minutes and then separated. A second portion of methyl tert-butyl ether (40 mL) was added and the reaction mixture was agitated for 5 minutes. The combined organic extracts were washed with water (10 mL) and concentrated under reduced pressure to give 7 as a colorless oil (2.05 g, 76.9% yield, >99% GC purity).

Chiral Process—Preparation of Impurities 6a-d

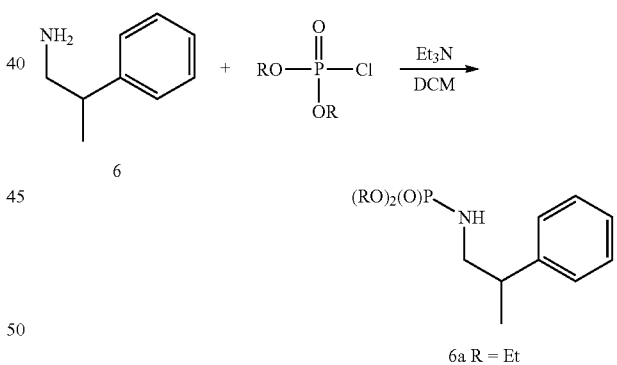

6a R = Et
6b R = Me
6c R = iPr
6d R = Ph

A 100 mL 3-neck flask was charged with 6 (1.0 g, 7.4 mmol), Et$_3$N (1.23 mL, 8.8 mmol), and dichloromethane (25 mL). The solution was cooled to 0-5° C. and a solution of chlorophosphate (8.15 mmol) in dichloromethane (5 mL) was added over 5 minutes. The reaction mixture was allowed to stir at ambient temperature overnight. The reaction mixture was then quenched by adding water (20 mL) and the organic layer was separated. The organic extract was washed with 1N HCl solution (10 mL), saturated NaHCO$_3$ solution (10 mL), and saturated sodium chloride solution (10 mL). The organic phase was concentrated to dryness to afford the desired product, 6a-d.

6a: 81% yield, colorless oil. 95.8% GC purity. $^1$H NMR (300 MHz, CDCl$_3$) δ 7.30-7.19 (m, 5H), 3.68 (d, J=11.1 Hz, 3H), 3.63 (d, J=11.1 Hz, 3H), 3.20-3.00 (m, 2H), 2.95-2.80 (m, 1H), 2.45 (s, br, 1H), 1.26 (d, J=6.9 Hz, 3H).

6b: 85% yield, colorless oil. 97.47% GC purity $^1$H NMR (300 MHz, CDCl$_3$) δ 7.32-7.19 (m, 5H), 4.04-3.91 (m, 4H), 3.20-3.95 (m, 2H), 2.92-2.80 (m, 1H), 2.45 (s, br, 1H), 1.26 (d, J=6.9 Hz, 3H).

6c: The residue was chromatographed on a 40 g Combiflash Gold column eluting with 100% heptanes to 100% ethyl acetate over a 20 minute gradient. Combined clean fractions we concentrated to dryness to give the desired product as a clear colorless oil in 42% yield, 97.3% purity GC. $^1$H NMR (300 MHz, CDCl$_3$) δ 7.37-7.10 (m, 5H), 4.61-4.44 (m, 2H), 3.20-2.91 (m, 2H), 2.90-2.78 (m, 1H), 2.41-2.28 (m, 1H), 1.35-1.16 (m, 15H).

6d: 91% yield, colorless oil. 95.16% GC purity. $^1$H NMR (300 MHz, CDCl$_3$) δ 7.26-7.04 (m, 15H), 3.48 (s, br, 1H), 3.35-3.22 (m, 1H), 3.03-2.90 (m, 2H), 1.21 (m, 3H).

Referring now to the following Chiral Scheme, Scheme 3 provides synthetic routes to the ethyl and methyl derivatives.

4.05 mmol, 1.1 eq) was added. The mixture was stirred at room temperature for 10 minutes followed by the addition of iodomethane (0.252 mL, 4.05 mmol, 1.1 eq). The reaction was followed by TLC analysis (silica gel plates; 1:1 hexanes/ethyl acetate and 95:5 dichloromethane/methanol) and additional base and iodomethane was added until the reaction was complete. The reaction was quenched with NaCl solution (20 mL) and extracted with ethyl acetate (40 mL). The organic extract was dried with anhydrous sodium sulfate, filtered and concentrated under reduced pressure. The residue was chromatographed (40 g Combiflash column, 100% heptane to 100% ethyl acetate eluent) and appropriate fractions were combined and evaporated to afford 8 as a colorless oil (0.511 g, 48% yield). Optical rotation c=1.10, ethanol, 25.2° C., +36.5°. $^1$H NMR (300 MHz, CDCl$_3$) δ 7.32-7.18 (m, 5H), 4.10-3.85 (m, 2H), 3.81-3.79 (m, 2H), 3.62-3.44 (m, 1H), 2.87-2.73 (m, 1H), 2.72-2.90 (m, 1H), 2.55 (d, J=9.6 Hz, 3H), 1.24 (t, J=6.8 Hz, 3H), 1.18-1.05 (m, 6H).

Scheme 3

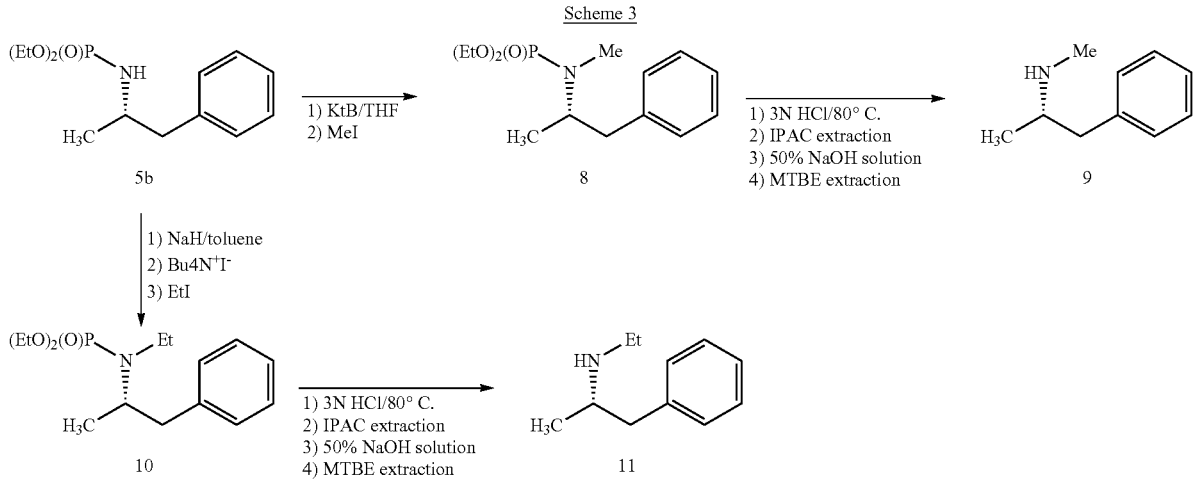

Note: both compounds isolated as their respective HCl salts mp and optical rotation matched the literature values Chiral Process—Preparation of (S)-diethyl methyl(1-phenylpropan-2-yl)phosphoramidate (8) from 5b

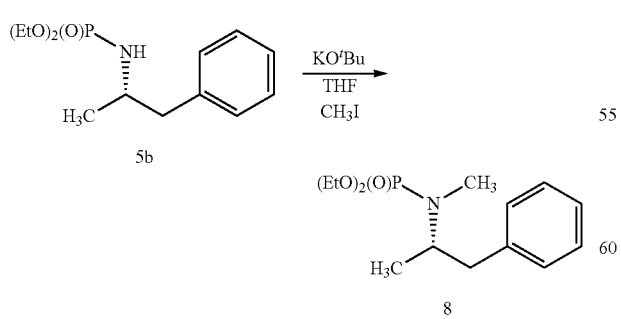

Chiral Process—Preparation of d-N-Methylamphetamine (9) from 8

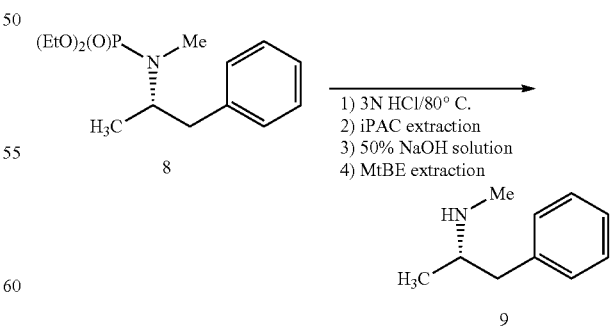

A 100 mL, 3 neck flask was charged with 5b (1.00 g, 3.68 mmol) and dry THF (40 mL). Stirring was started and once a solution was obtained, potassium tert-butoxide (0.455 g, A 50 mL, 3-necked round bottomed flask was charged with 8 (0.5 g, 1.75 mmol) and 3 M HCL (25 mL) and the stirred reaction mixture was heated to 80° C. for 2.5 hours and then cooled to room temperature. The orange solution was extracted with isopropyl acetate (25 mL) and the organic extract layer was discarded. Sodium hydroxide solution (50% solution, 10 mL) was slowly added to the remaining aqueous layer, keeping the internal temperature below 25° C. Methyl tert-butyl ether (20 mL) was added and the reaction mixture was agitated for 20 minutes then allowed to separate for 30 minutes. The aqueous layer was removed and the organic layer washed with water (10 mL), dried over anhydrous sodium sulfate, filtered and concentrated under reduced pressure to give a light brown oil. This oil was distilled (bulb-to-bulb at 65-67° C. @ 0.6 mm Hg vacuum) to afford 9 as a colorless oil (0.19 g, 75% yield). This distillate was converted to the known HCl salt for analysis. mp 172-175° C. Optical rotation c=1.00, water, 25.2° C., +16.3°.

Chiral Process—Preparation of (S)-diethyl ethyl(1-phenylpropan-2-yl)phosphoramidate (10) from 5b

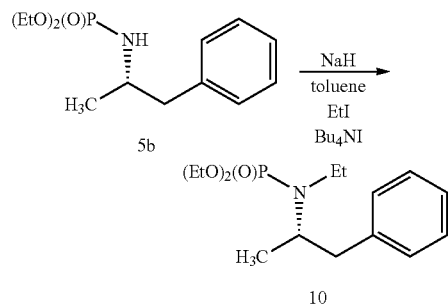

A 100 mL, 3-neck flask was charged with toluene (40 mL) and 5b (5.58 g, 20 mmol) and the mixture was stirred until a solution was obtained. To this solution was added sodium hydride (60% suspension in mineral oil, 0.880 g, 22.0 mmol, 1.1 eq) followed by tetrabutylammonium iodide (0.369 g, 1 mmol), and iodoethane (2.41 mL, 30 mmol). The mixture was heated to 80° C. for 4 hours. Additional portions of iodoethane (0.200 mL) and sodium hydride (0.100 g) were added which resulted in complete consumption of 5b. The reaction was cooled to room temperature, quenched with NaCl solution (20 mL). The layers were separated and the aqueous phase extracted with toluene (40 mL). The combined organic phases were dried with anhydrous sodium sulfate, filtered and concentrated to a brown oily residue. This residue was chromatographed (40 g Combiflash column, 100% heptane to 100% ethyl acetate eluent) and product fractions were combined and evaporated under reduced pressure to give 10 as a clear, pale yellow oil (3.78 g, 12.6 mmol, 63% yield). Optical rotation c=1.00, ethanol, 25.0° C., +35.6°. $^1$H NMR (300 MHz, CDCl$_3$) δ 7.31-7.10 (m, 5H), 4.08-3.62 (m, 5H), 3.11-2.88 (m, 3H), 2.76-2.67 (m, 1H), 1.32-1.21 (m, 6H), 1.20-1.10 (m, 6H).

Chiral Process—Preparation of d-N-Ethylamphetamine (11) from 10

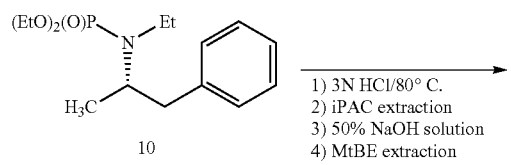

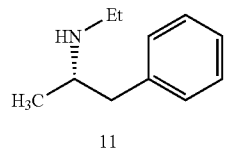

A 50 mL round bottomed flask was charged with 10 (2.5 g, 8.3 mmol) and 3 M HCl (25 mL) and the stirred reaction mixture was heated to 80° C. for 3.25 hours and cooled to room temperature. The orange solution was extracted with isopropyl acetate (25 mL) and the organic extract layer was discarded. Sodium hydroxide solution (50% solution, 25 mL) was slowly added to the remaining aqueous layer, keeping the internal temperature below 25° C. Methyl tert-butyl ether (20 mL) was added and the reaction mixture was agitated for 20 minutes and allowed to separate for 30 minutes. The aqueous layer was removed and the organic layer washed with water (10 mL) and concentrated under reduced pressure to give a brown oily residue. This residue was distilled (bulb-to-bulb; 105-106° C. @ 14.0 mm Hg vacuum) to give 11 as a colorless oil (1.10 g, 81% yield). Distillation: 105-106° C., 14.0 mm Hg. This oil was converted to the known HCl salt for analysis. mp 154-156° C. Optical rotation c=2.00, water, 20.0° C., +17.1°.

Racemic Processes

In one preferred aspect the invention provides a synthetic pathway to RACEMIC amphetamine mixtures or compositions by using an aziridine based process with an organometallic compound by heating the reactants in a first step, and then adding as a second step the Grignard reagent in a dosage controlled fashion. In a preferred embodiment, the reaction is heated to above 40 degrees C., preferably above about 45 degrees C., and more preferably above about 48 degrees C. In one embodiment, the temperature is maintained from 48-51 deg. C. for about 30 minutes and then brought to room temperature.

In another preferred racemic process embodiment, the invention provides a process of making the amphetamine, said process comprising:

providing a compound of Formula 6:

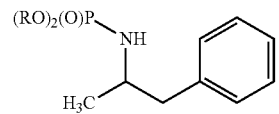

wherein R is alkyl or aryl; and
deprotecting the compound of Formula 6 under acidic conditions effective to produce amphetamine of Formula 7:

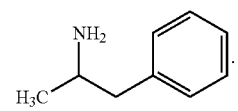

In preferred aspects, the amphetamine racemic process comprises wherein the acidic conditions are aqueous hydrochloric, sulfuric or phosphoric acids.

In preferred aspects, the amphetamine racemic process s comprises wherein the aqueous acid water content is in an amount of 50% to 90%

In preferred aspects, the amphetamine racemic process comprises wherein the R=methyl, ethyl, isopropyl or phenyl.

In preferred aspects, the amphetamine racemic process comprises wherein said providing a compound of Formula 6 comprises:

providing a compound of Formula 2:

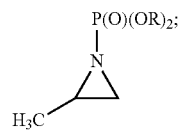

2 wherein R is alkyl or aryl and reacting the compound of Formula 2 with phenylmagnesium halide and a copper catalyst under solvent and temperature conditions effective to produce a compound of Formula 6 in a purity substantially free of any regioisomeric impurities.

In preferred aspects, the amphetamine racemic process comprises wherein the regioisomeric purity of Formula 6 is >99% and the regioisomer (Formula 8) is <0.1%.

In preferred aspects, the amphetamine racemic process comprises wherein the R=methyl, ethyl, isopropyl or phenyl.

In preferred aspects, the amphetamine racemic process comprises wherein the copper catalyst is CuCl, $CuCl_2$, CuBr, CuF, CuI, $Cu(OAc)_2$, Cu(OMe)2, Copper nanoparticles, Copper turnings, or combinations thereof.

In preferred aspects, the amphetamine racemic process comprises wherein the solvent is an organic ether or an organic ether-toluene mixture.

In preferred aspects, the amphetamine racemic process comprises wherein the organic ether solvent is diethyl ether, tetrahydrofuran or 2-methyltetrahydrofuran.

In preferred aspects, the amphetamine racemic process comprises wherein the phenylmagnesium halide is either phenylmagnesium chloride, phenylmagnesium bromide or phenylmagnesium iodide.

In preferred aspects, the amphetamine racemic process comprises wherein the phenylmagnesium halide solutions can either be commercially supplied or prepared in situ from the corresponding halobenzene and magnesium.

In preferred aspects, the amphetamine racemic process s comprises wherein the magnesium is be in the form of chips, granules, ribbon, turnings, dust, grit, blocks or chunks.

In preferred aspects, the amphetamine racemic process comprises wherein said treating is carried out at a temperature of from about −10° C. to about 70° C.

In preferred aspects, the amphetamine racemic process comprises wherein said treating is carried out at a temperature of from about 30° C. to about 60° C.

In preferred aspects, the amphetamine racemic process comprises wherein said providing a compound of Formula 2 comprises:

providing a compound of Formula 5:

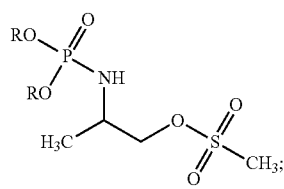

5 wherein R is alkyl or aryl; and reacting the compound of Formula 5 with the base under conditions effective to produce a compound of Formula 2.

In preferred aspects, the amphetamine racemic process comprises a compound of Formula 5 wherein the R=methyl, ethyl, isopropyl or phenyl.

In preferred aspects, the amphetamine racemic process comprises wherein the base is potassium hydroxide or potassium carbonate.

In preferred aspects, the amphetamine racemic process comprises wherein said providing a compound of Formula 5 comprises:

providing a compound of Formula 4:

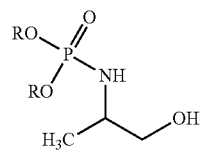

wherein R is alkyl or aryl; and reacting the compound of Formula 4 with methanesulfonyl chloride and a base under conditions effective to produce a compound of Formula 5.

In preferred aspects, the amphetamine racemic process comprises a compound of Formula 4 wherein the R=methyl, ethyl, isopropyl or phenyl.

In preferred aspects, the amphetamine racemic process comprises wherein said providing a compound of Formula 4 comprises:

providing a compound of Formula 3:

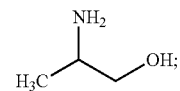

and reacting the compound of Formula 3 with the appropriate

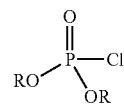

wherein R=alkyl or aryl under conditions effective to produce a compound of Formula 4.

In preferred aspects, the amphetamine racemic process involving Formula 4 comprises wherein the R=methyl, ethyl, isopropyl or phenyl.

In another preferred embodiment, the invention provides a compound of formula 6:

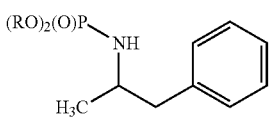

prepared according to one or more processes herein, in a regioisomeric purity of >1700:1 wherein:

R is alkyl or aryl

In preferred aspects of the racemic process, the invention further comprises a compound of formula 6:

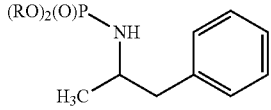

wherein the alkyl group is selected from the group consisting of methyl, ethyl or isopropyl.

In preferred aspects of the racemic process, the invention further comprises a compound of formula 6:

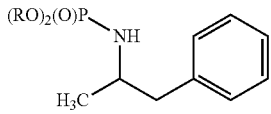

wherein the aryl group is phenyl.

Racemic Aziridine

In another preferred embodiment of the racemic process, the invention provides a compound of formula 2:

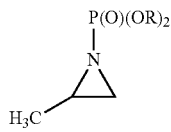

wherein: R is alkyl or aryl

In preferred aspects of the racemic process, the invention further comprises a compound of formula 2:

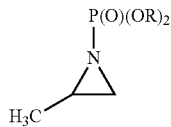

wherein the alkyl group is selected from the group consisting of methyl, ethyl or isopropyl.

In preferred aspects of the racemic process, the invention further comprises a compound of formula 2:

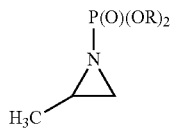

wherein the aryl group is phenyl.

General Racemic Process

In yet another preferred embodiment of the racemic process, there is provided a process for the synthesis of amphetamine derivatives comprising the step of performing an organo cuprate addition reaction upon an aziridine phosphoramidate compound to obtain an aryl or aryl-alkyl phosphoramidate amphetamine precursor.

Solvent Extraction of Racemic Mixture

In yet another preferred embodiment of the racemic process, there is provided a process for crystallization of compounds 6a-d from a mixture of compounds 6a-d and 8a-d, comprising the step of performing a crystallization using a mixture of two or more solvents wherein at least one of the two or more solvents is THF.

Accordingly, the present racemic process relates to processes for the synthesis of amphetamine, dexamphetamine, methamphetamine, derivatives of these, including their salts, and novel precursors and intermediates obtained thereby, by synthesizing aziridine phosphoramidate compounds in specified solvents at specified temperatures, and then converting to a novel aryl or aryl-alkyl phosphoramidate precursor using an organometallic compound such as a copper salt, where the novel aryl or aryl-alkyl phosphoramidate precursor is then easily converted to the target compounds using known reactions, e.g. acid dephosphorylation, alkylation of the nitrogen followed by acid dephosphorylation, etc.

Racemic Process Experimental Introduction:

Unless otherwise noted, reagents and solvents were used as received from commercial suppliers.

NMR spectra: Proton nuclear magnetic resonance spectra were obtained on a Bruker AV 300 or a Bruker AV 500 spectrometer at 300 MHz and 500 MHz, respectively. Spectra are given in ppm (δ) and coupling constants, J, are reported in Hertz. Tetramethylsilane was used as an internal standard for proton spectra.

HPLC analyses: Analyses were obtained on a Varian Prostar 210 HPLC system using a Prevail C18 column (53×7 mm, Alltech) with PDA detection at 208-210 nm and solvent gradient program Method A.

HPLC Method A:

| Time (min) | Flow (mL/min) | % A | % B |
|---|---|---|---|
| 0.0 | 2.0 | 95.0 | 5.0 |
| 10.0 | 2.0 | 5.0 | 95.0 |
| 11.5 | 2.0 | 5.0 | 95.0 |
| 11.6 | 2.0 | 95.0 | 5.0 |
| 13.0 | 2.0 | 95.0 | 5.0. |

A = Water with 0.05% v/v Trifluoroacetic Acid
B = Acetonitrile with 0.05% v/v Trifluoroacetic Acid HPLC Method B Flow rate: 0.7 mL/min Run time: 35 min Temp: ambient Mobile phase: 90% water pH=1.5 (perchloric acid): 10% Methanol GC (FID): Analyses were obtained on a Varian CP 3800 GC using a Supleco (Cat #24048) SPB-5 30×0.320; 0.25 μm column.

Column temperature initial: 50° C.

Column temperature final: 275° C.

Ramp profile: 20.0 deg/min

Injector temperature: 250° C.

Detector temperature: 250° C.

Carrier Gas/flow rate: Helium, 2 mL/min

Racemic Example 1: Preparation of diethyl (2methylaziridin-1-yl)phosphonate (2a)

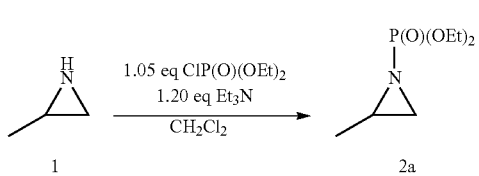

A 12 L 4-neck flask fitted with an overhead mechanical stirrer, temperature probe and 1 L pressure equalizing addition funnel was charged with 2-methylaziridine (300 g, 5.25 mol purchased from Menadiona SL of Barcelona, Spain), triethylamine (880 mL, 6.3 mol) and dichloromethane (3.0 L). The stirred solution was cooled to 5° C. and diethoxyphosphoryl chloride (804 mL, 5.51 mol) was added over 2.5 hours while maintain the internal temperature below 15° C. The reaction was then stirred for 18 hours, at which point the reaction was complete reaction was complete by TLC analysis (silica gel plate, 93:6:1 dichloromethane/MeOH/NH$_4$OH and 6/3/1 CHCl$_3$/MeOH/NH$_4$OH; KMnO$_4$ stain). Water (3 L) was charged and the biphasic mixture was stirred for 20 minutes. The layers were separated and the organic layer was concentrated under reduced pressure. The remaining yellow oil was clarified by filtration. The filtrate (1028 g) was purified by short path vacuum distillation at 66-67° C., 1.0 mm Hg. to afford 2a as a colorless liquid (864.8 g, 85% yield, 99.0% GC purity). $^1$H NMR (300 MHz, CDCl$_3$) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Racemic Example 2: Preparation of diphenyl (2methylaziridin-1-yl)phosphonate (2b)

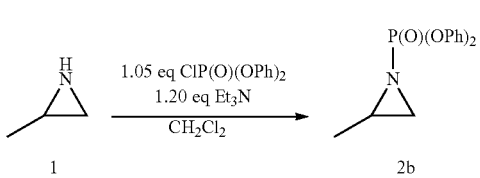

Compound 2b is prepared as described in Stephens, Moffett, Vaughan, Hill and Brown in the Journal of Chemical and Engineering Data, 1969, 14, 114-116, but substituting toluene for benzene, and is obtained as a thick colorless oil in about 55% yield after vacuum distillation. Expected $^1$H NMR (300 MHz, CDCl$_3$) δ 7.40-7.15 (m, 10H), 2.81-2.69 (m, 1H), 2.62-2.49 (dd, J=17.6, 5.6 Hz, 1H), 2.10-2.00 (dd, J=14.1, 4.9 Hz, 1H) and 1.28-1.24 ppm (m, 3H).

Racemic Example 3: Preparation of dimethyl (2methylaziridin-1-yl)phosphonate (2c)

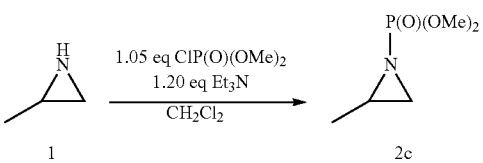

Compound 2c is prepared following the general procedure in Stephens, Moffett, Vaughan, Hill and Brown in the Journal of Chemical and Engineering Data, 1969, 14, 114-116 but substituting toluene for benzene, and is obtained as a colorless oil in about 73% yield after vacuum distillation (75-80° C. @ 10 mm Hg vacuum). Expected $^1$H NMR (300 MHz, CDCl$_3$) δ 3.80 (s, 3H), 3.76 (s, 3H), 2.65-2.50 (m, 1H), 2.42-2.31 (dd, J=17.6, 5.6 Hz, 1H), 1.92-1.85 (dd, J=14.1, 4.9 Hz, 1H), 1.28 (dd, J=5.4, 1.2 Hz, 3H).

Racemic Example 4: Preparation of diisopropyl (2methylaziridin-1-yl)phosphonate (2d)

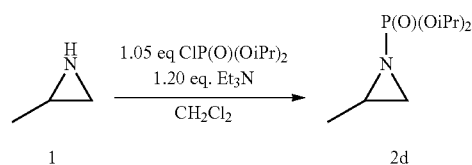

Compound 2d is prepared following the general procedure in Stephens, Moffett, Vaughan, Hill and Brown in the Journal of Chemical and Engineering Data, 1969, 14, 114-116 but substituting toluene for benzene, and is obtained as a colorless oil in about 80% yield after vacuum distillation (79-82° C. @ 3 mm Hg vacuum). Expected $^1$H NMR (300 MHz, CDCl$_3$) δ 4.71 (m, 2H), 2.64-2.41 (m, 1H), 2.28 (dd, J=17.6, 5.6 Hz, 1H), 1.81 (dd, J=14.1, 4.9 Hz, 1H), 1.34 (m, 12H) and 1.22 (dd, J=5.6, 1.2 Hz, 3H).

Racemic Example 5: Preparation of diethyl (2methylaziridin-1-yl)phosphonate (2a), Alternate Route

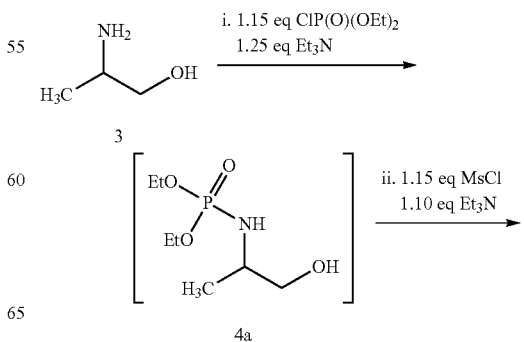

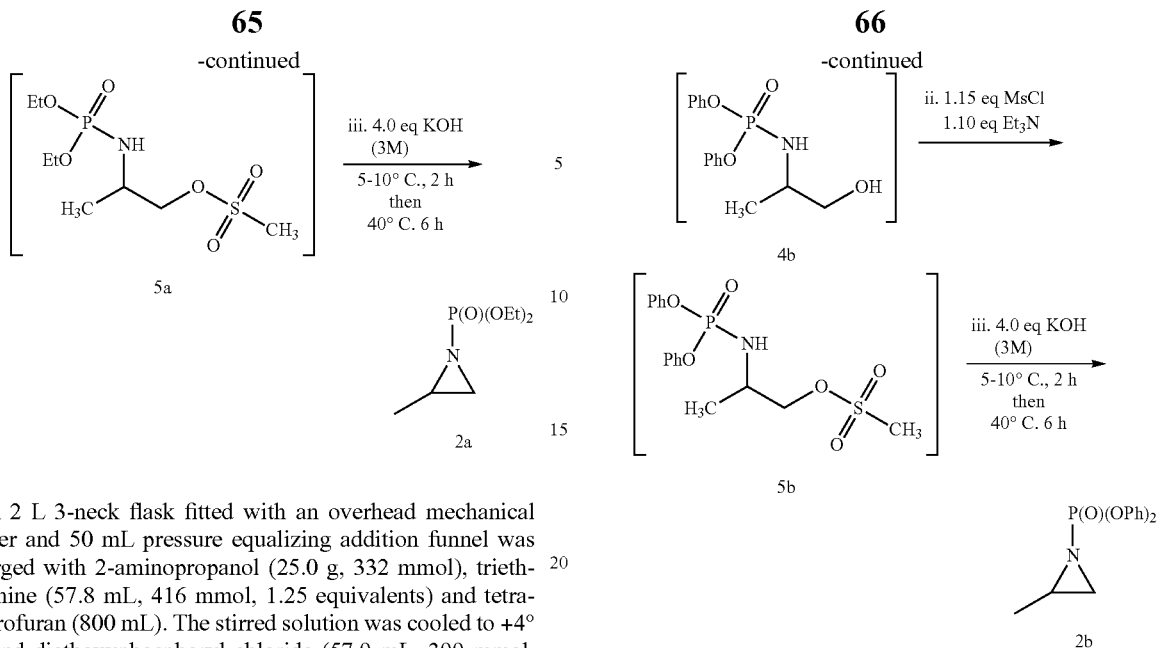

A 2 L 3-neck flask fitted with an overhead mechanical stirrer and 50 mL pressure equalizing addition funnel was charged with 2-aminopropanol (25.0 g, 332 mmol), triethylamine (57.8 mL, 416 mmol, 1.25 equivalents) and tetrahydrofuran (800 mL). The stirred solution was cooled to +4° C. and diethoxyphosphoryl chloride (57.9 mL, 399 mmol, 1.20 equivalents) was added over 20 minutes while maintaining an internal temperature <+15° C. The reaction mixture was stirred an additional 30 minutes at which point the reaction was complete by TLC analysis (silica gel plate, 93:6:1 dichloromethane/MeOH/NH$_4$OH and 6/3/1 CHCl$_3$/MeOH/NH$_4$OH; KMnO$_4$ stain). Additional triethylamine (57.8 mL, 416 mmol, 1.10 equivalents) was added to the reaction mixture and methanesulfonyl chloride (32.3 mL, 416 mmol, 1.25 equivalents) was added drop-wise over 25 minutes while maintaining an internal temperature <+18° C. The resulting reaction mixture was stirred for 1.5 hours at which time TLC analysis (see above methods) indicated the reaction was complete. Potassium hydroxide solution (3 M solution, 555 mL, 1.6 mol, 5.0 equivalents) was slowly added to the stirred reaction mixture while maintaining an internal temperature <+20° C. The reaction was stirred for 30 minutes and diluted with ethyl acetate (300 mL). The layers were separated and the aqueous layer was extracted with ethyl acetate (300 mL). The combined organic extract was washed with saturated sodium chloride solution (300 mL) and dried over anhydrous sodium sulfate. The solution was clarified and then concentrated under reduced pressure to afford crude 2 as an orange oil. The oil was purified by short path distillation (72-74° C., 10 mm Hg vacuum) to afford purified 2a as a colorless oil (48.2 g, 75% yield, 99.0% GC purity). $^1$H NMR (300 MHz, CDCl$_3$) δ 4.15 (dq, J=8.0, 7.1 Hz, 4H), 2.64-2.45 (m, 1H), 2.33 (ddd, J=17.9, 5.9, 1.3 Hz, 1H), 1.91-1.81 (m, 1H), 1.34 (dt, J=7.1, 0.9 Hz, 6H), 1.28 (dd, J=5.4, 1.4 Hz, 3H).

Racemic Example 6: Preparation of diphenyl (2methylaziridin-1-yl)phosphonate (2b) Alternate Route

Following the procedure for the alternate preparation of 2a, diphenyl (2methylaziridin-1-yl)phosphonate (2b) is prepared as a thick colorless oil in about 30% yield (expected minimum 97% GC purity). Expected $^1$H NMR (300 MHz, CDCl$_3$) δ 7.40-7.15 (m, 10H), 2.81-2.69 (m, 1H), 2.62-2.49 (dd, J=17.6, 5.6 Hz, 1H), 2.10-2.00 (dd, J=14.1, 4.9 Hz, 11H) and 1.28-1.24 ppm (m, 3H).

Racemic Example 7: Preparation of dimethyl (2methylaziridin-1-yl)phosphonate (2c) Alternate Route Following the procedure for the alternate preparation of 2a, dimethyl (2methylaziridin-1-yl)phosphonate (2c) is prepared as a viscous colorless oil in about 70% yield (expected 95% GC minimum purity). Expected $^1$H NMR (300 MHz, CDCl$_3$) δ 3.80 (s, 3H), 3.76 (s, 3H), 2.65-2.50 (m, 1H), 2.42-2.31 (dd, J=17.6, 5.6 Hz, 1H), 1.92-1.85 (dd, J=14.1, 4.9 Hz, 11H), 1.28 (dd, J=5.4, 1.2 Hz, 3H).

Racemic Example 8: Preparation of diisopropyl (2methylaziridin-1-yl)phosphonate (2d) Alternate Route

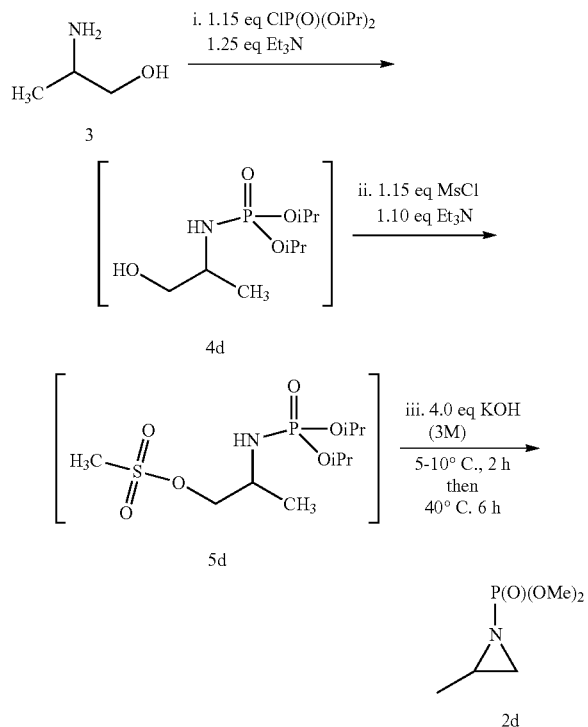

Following the procedure for the alternate preparation of 2a, diisopropyl (2methylaziridin-1-yl)phosphonate (2d) is prepared as a viscous colorless oil in about 50% yield (expected 95% GC minimum purity). Expected $^1$H NMR (300 MHz, CDCl$_3$) δ 4.71 (m, 2H), 2.64-2.41 (m, 1H), 2.28 (ddd, J=17.6, 5.6, 1.3 Hz, 1H), 1.81 (dd, J=14.1, 4.9, 1.3 Hz, 1H), 1.34 (m, 12H) and 1.22 (dd, J=5.6, 1.2 Hz, 3H).

Racemic Example 9: Preparation of diethyl (1-phenylpropan-2-yl)phosphoramidate (6a) [CuI Catalyst)

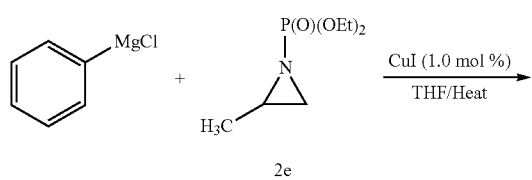

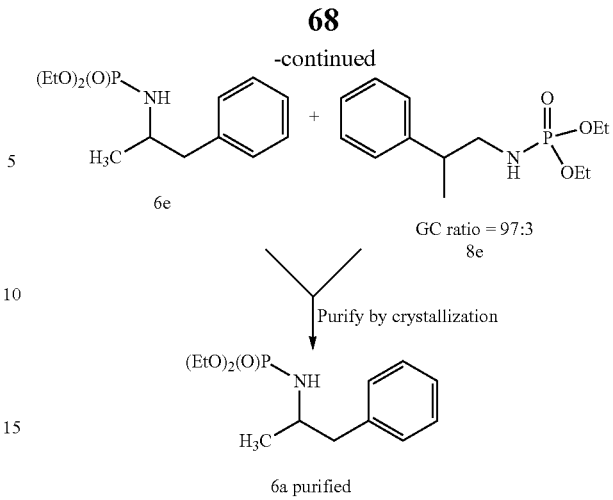

A 250 mL, jacketed, three necked flask equipped with an overhead stirrer, 50 mL pressure equalizing addition funnel and a temperature probe was charged with 2a (10 g, 51.7 mmol), THF (50 mL) and CuI (98 mg, 1.0 mol %) and the stirred mixture was heated to 30° C. The pressure equalizing addition funnel was charged with PhMgCl (2M in THF, 32.36 mL) and the solution was added over 20 minutes while maintaining an internal temperature of 30-32° C. After the addition was complete, the reaction mixture was heated to 45-50° C. for an additional 30 minutes and then cooled to ambient temperature. The reaction was quenched by slow addition to a cooled mixture of saturated aqueous ammonium chloride solution and water (50/50 v/v, 100 mL) while maintaining an internal temperature below 20° C. The flask was rinsed with methyl t-butyl ether (100 mL) and the rinse was transferred to the quenched reaction mixture. The biphasic mixture was stirred for 5 minutes, allowed to separate for 20 minutes and then the aqueous phase was removed. The organic phase washed with saturated sodium chloride solution (50 mL) and the organic phase was dried over sodium sulfate. The solution (a 97:7 mixture of 6a: 8a by GC analysis) was filtered and concentrated under reduced pressure until the product began to crystallize. Heptane (40 mL) was added to the slurry and the mixture was heated until a solution was obtained. The stirred solution allowed to cool to room temperature and stirred for 18 hours. The solid was collected by filtration and dried under reduced pressure at 30° C. for 18 hours affording diethyl (1-phenylpropan-2-yl) phosphoramidate (6a) as a white crystalline solid (9.12 g, 65% yield; 99.72% GC purity with 0.04% 8a present). Mp 66-67° C. (lit$^1$ 57-58° C.). $^1$H NMR (300 MHz, CDCl$_3$) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

Racemic Example 10: Preparation of diethyl (1-phenylpropan-2-yl)phosphoramidate (6a) [CuCl Catalyst]

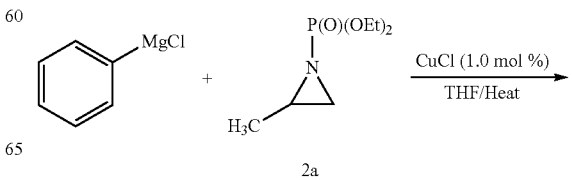

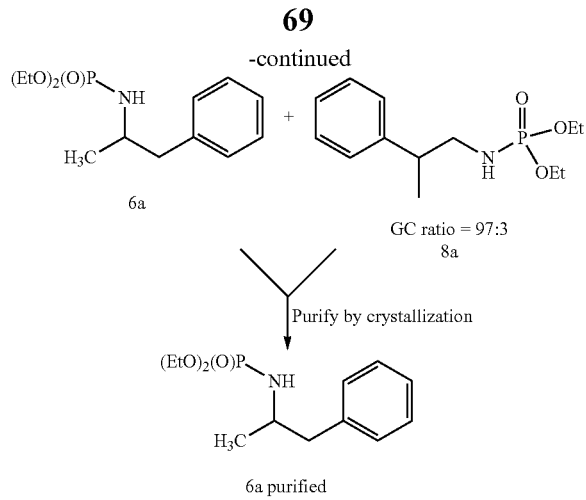

6a

+

GC ratio = 97:3
8a

Purify by crystallization 6a purified

A 12 L, jacketed, bottom outlet flask was charged with 2a (700 g, 3.62 mol), THF (3.5 L) and CuCl (3.58 g, 1.0 mol %) and the stirred mixture was heated to 45° C. A pressure equalizing addition funnel was charged with PhMgCl (2M in THF, 2.26 L) and the solution was added slowly while maintaining an internal temperature below 52° C. After the addition was complete, the reaction mixture was stirred at 48-51° C. for an additional 30 minutes. GC analysis indicated the consumption of 2a (<1.0%) and the reaction mixture was cooled to ambient temperature. The reaction was quenched by slow addition to a cooled mixture of saturated aqueous ammonium chloride solution and water (50/50 v/v, 4.2 L) while maintaining an internal temperature below 25° C. The flask was rinsed with heptanes (3.5 L) and the rinse was transferred to the quenched reaction mixture. The biphasic mixture was stirred for 5 minutes, allowed to separate for 20 minutes and then the aqueous phase was removed. The organic phase was concentrated under reduced pressure to a volume of about 1.0 L. The organic solution was azeotropically dried by two separate charges of heptanes (2×2.0 L) was added and the solution volume was adjusted by reduced pressure distillation to a total volume of about 2.5 L. The slurry was heated to 60-65° C. until the solids dissolved and then stirrer was slowed and the crystallization was allowed to proceed for about 24 hours as the batch cooled to ambient temperature. The slurry was cooled to 5° C. for about 1.5 hours. The resulting crystalline solid was collected by vacuum filtration and washed with cold heptanes (2×350 mL). After drying under vacuum at 35° C. for 48 hours the diethyl (1-phenylpropan-2-yl)phosphoramidate (6a) was obtained as a white crystalline solid (806.1 g, 82% yield; 99.90% GC purity with 0.04% 8a present). Mp 64-65° C. (lit[1] 57-58° C.). $^1$H NMR (300 MHz, CDCl$_3$) δ 7.36-7.08 (m, 5H), 4.14-3.85 (m, 3H), 3.85-3.66 (m, 1H), 3.58-3.32 (m, 1H), 2.81-2.61 (m, 2H), 2.38 (t, J=9.8 Hz, 1H), 1.38-1.18 (m, 6H), 1.15 (d, J=6.4 Hz, 3H).

Phenyl Grignard

The phenyl Grignard can be either be purchased commercial solutions, at about 2 moles of active reagent per liter of solution, or prepared in situ from the corresponding halobenzene and magnesium metal turnings. For phenylmagnesium chloride, the solvents of choice are either THF or 2-methylTHF. For phenylmagnesium bromide, the solvents of choice are either THF, 2-methylTHF or diethyl ether. For phenylmagnesium iodide the solvent of choice is diethyl ether. The use of any of these ether solvents (alone or mixed with toluene) in conversion to 2a to 6a, following the established procedure, affords 6a in comparable isolated yield, GC purity and devoid of the regioisomer 8a.

Other Copper

The use of other copper sources CuCl2, CuBr, CuF, Cu(OAc)2, Cu(acac)2, Cu(Ome)2, copper nanoparticles, copper turnings, copper grit, copper powder, copper shot, copper foil, copper flake, copper disk, copper precipitate, copper mist, copper dust, copper granules, and copper slug, in conversion to 2a to 6a, following the established procedure, affords 6a in comparable isolated yield, GC purity and devoid of the regioisomer 8a.

Racemic Example 11: Preparation of diphenyl (1-phenylpropan-2-yl)phosphoramidate (6b)

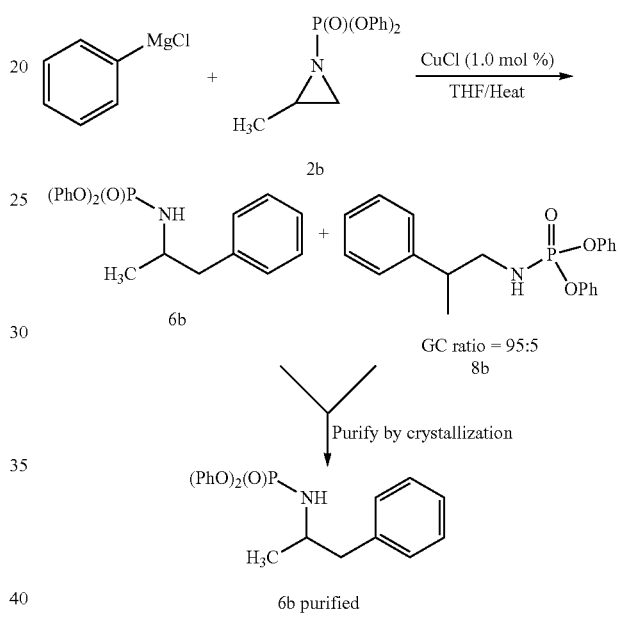

2b

6b

+

GC ratio = 95:5
8b

Purify by crystallization 6b purified

A 100 mL, 3-necked flask equipped with an overhead stirrer, reflux condenser and pressure equalizing addition funnel was charged with 2b (10.0 g, 34.6 mmol), THF (50 mL) and CuCl (42 mg, 1 mol %) and the stirrer was started. The stirred mixture was heated to 48° C. and the pressure equalizing addition funnel was charged with PhMgCl (2M in THF, 17.4 mL). This solution was added slowly while maintaining a reaction temperature of 48-51° C. The reaction was allowed to stir at 48-51° C. for an additional 2 hours until the GC analysis indicated the consumption of 2b (<1.0%) and the reaction mixture was cooled to ambient temperature. The reaction was quenched by slow addition to a cooled solution of saturated aqueous ammonium chloride/ water mixture (50/50 v/v, 60 mL) while maintaining the batch temperature below 20° C. Heptanes (60 mL) was used to rinse the reactor and was transferred to the quench mixture. The biphasic mixture was agitated for 15 minutes and the aqueous layer was removed. The organic layer washed with deionized water (20 mL) and the organic phase concentrated under reduced pressure to give viscous oil. This residue was dissolved in heptanes (50 mL) and the solution was concentrated under reduced pressure. The residue was crystallized from ethanol (1 g/5 mL) to give 6b as a white solid (9.05 g, 72% yield, 99.85% GC purity containing 0.05% of 8b). Mp 102-103° C. (lit[1] 101-102° C.).

$^1$H NMR (300 MHz, CDCl$_3$) δ 7.38-7.11 (m, 15H), 3.83-3.65 (m, 11H), 3.00-2.89 (m, 11H), 2.86-2.78 (m, 1H), 2.73-2.62 (m, 1H), 1.15 (d, J=10.1 Hz, 3H).

Racemic Example 12: Preparation of dimethyl (1-phenylpropan-2-yl)phosphoramidate (6c)

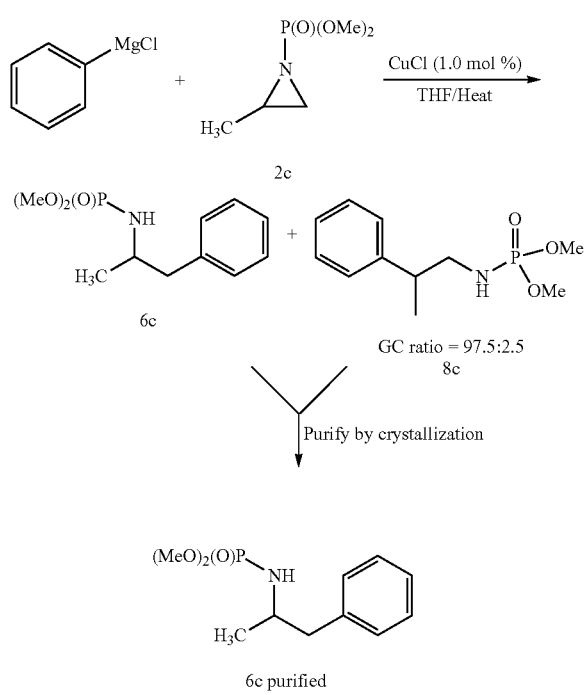

A 100 mL, 3-necked flask equipped with an overhead stirrer, reflux condenser and pressure equalizing addition funnel was charged with 2c (10.0 g, 60.5 mmol), THF (60 mL) and CuCl (70 mg, 1 mol %) and the stirrer was started. The mixture was heated to 48° C. and the pressure equalizing addition funnel was charged with PhMgCl (2M in THF, 13 mL). This solution was added slowly while maintaining an internal temperature of 48-51° C. The reaction was stirred at 48-51° C. for an additional 30 minutes until the GC analysis indicated the consumption of 2c (<1.0%) and the reaction mixture was cooled to ambient temperature. The reaction was quenched by slow addition to a cooled solution of saturated aqueous ammonium chloride in water (50/50 v/v, 100 mL) while maintaining the temperature below 20° C. Heptanes (100 mL) was used to rinse the reactor and the rinse solution was transferred to the quenched reaction mixture. The mixture was agitated for 15 minutes, allowed to separate for 30 minutes then the aqueous phase was discarded. The organic phase washed with deionized water (30 mL) and the organic phase concentrated under reduced pressure to give an oil. The residue was dissolved in heptanes (100 mL) and the solution was concentrated under reduced pressure. The residue was crystallized from methyl tert-butyl ether (1 g/3 mL), filtered and dried to give 6c as white needles (10.2 g; 74.8% yield), with 99.90% GC purity containing 0.06% 8c. Mp 86-88° C. $^1$H NMR (300 MHz, CDCl$_3$) δ 7.32-7.17 (m, 5H), 3.66 (d, J=6.4 Hz, 3H), 3.50-3.83 (m, 1H), 2.71 (d, J=6.6 Hz, 2H), 2.45 (m, 1H), 1.15 (d, J=6.6 Hz, 3H).

Racemic Example 13: Preparation of diisopropyl (1-phenylpropan-2-yl)phosphoramidate (6d)

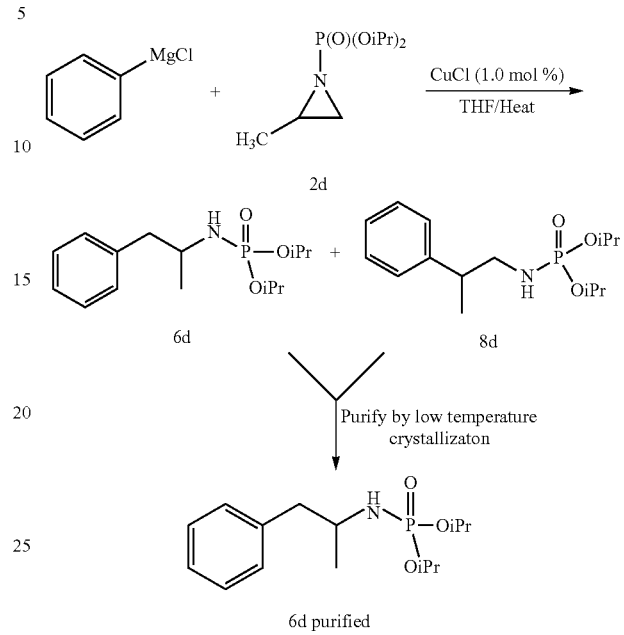

Following the procedure for the alternate preparation of 6a, diisopropyl (1-phenylpropan-2-yl)phosphoramidate (6d) is prepared as a viscous colorless oil in about 50% yield (expected GC purity: >99.7% 6d with <0.1% 8d). Expected $^1$H NMR (300 MHz, CDCl$_3$) δ 7.32-7.17 (m, 5H), 4.59-4.41 (m, 2H), 3.53-3.41 (m, 1H), 2.86-2.80 (m, 1H), 2.69-2.61 (m, 1H), 2.36 (t, J=9.6 Hz, 1H), 1.32-1.26 (m, 12H), 1.08 (d, J=10.1 Hz, 3H).

Racemic Example 14: Preparation of Amphetamine (7) from 6a

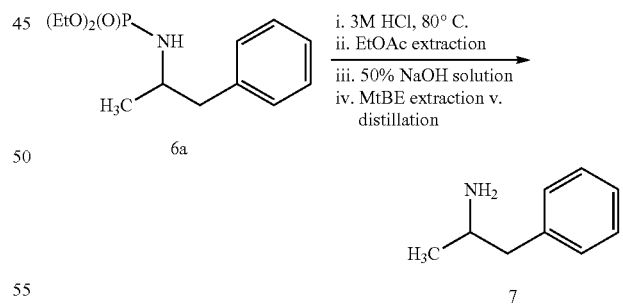

A 12 L, jacketed, bottom outlet valve flask was charged with 6a (800 g, 2.95 mol) and 3 M hydrochloric acid (3.0 L) and the reaction mixture was heated to 80° C. for 1.5 hours at which point HPLC analysis indicated that the reaction was complete, and then cooled to room temperature. The brown solution was washed with ethyl acetate (1.5 L) and the organic extract layer was discarded. Sodium hydroxide solution (50% solution, 560 mL) was slowly added to the remaining aqueous layer, keeping the temperature below 25° C. Methyl tert-butyl ether (1.0 L) was added and the mixture was agitated for 20 minutes then allowed to separate for 30 minutes. The aqueous layer was removed and the organic layer was concentrated under reduced pressure to afford a light yellow oil. This oil was short path distilled (75-78° C. at 10 mmHg vacuum) to give racemic amphetamine (7) as a clear colorless oil (335.76 g, 84.3% yield; 99.93% pure by GC). $^1$H NMR (300 MHz, CDCl$_3$) δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H).

Racemic Example 15: Preparation of Amphetamine (7) from 6b

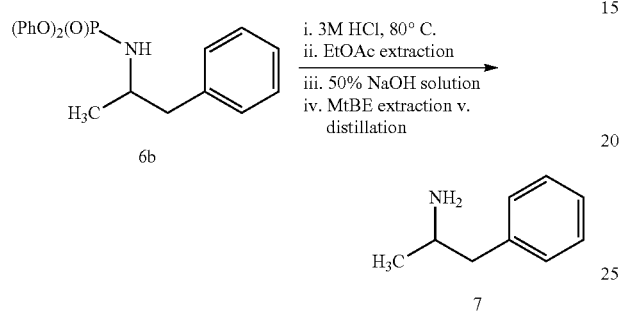

A 50 mL flask is charged with 6b (7.5 g, 20.41 mmol) and 3 M HCl (20.0 mL) and the stirred reaction mixture is heated to 80° C. for 32 hours, at which point HPLC analysis should indicate the reaction is complete, and it is cooled to room temperature. The organic layer is washed with ethyl acetate (2×25 mL) and the organic extracts are discarded. The aqueous layer is treated with sodium hydroxide solution (50%, 12.0 mL) keeping the temperature below 25° C. Methyl tert-butyl ether (50 mL) is added and the reaction mixture is agitated for 5 minutes and then separated. A second portion of methyl tert-butyl ether (50 mL) is added and the reaction mixture is agitated for 5 minutes. The combined organic extracts are washed with water (10 mL) and the organic layer is concentrated under reduced pressure to give 7 as a colorless oil in about 80% yield. The expected purity is >99% by GC purity and 99% by HPLC. The expected $^1$H NMR spectra (300 MHz, CDCl$_3$) is δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H) and matches the reference spectra.

Racemic Example 16: Preparation of Amphetamine (7) from 6c

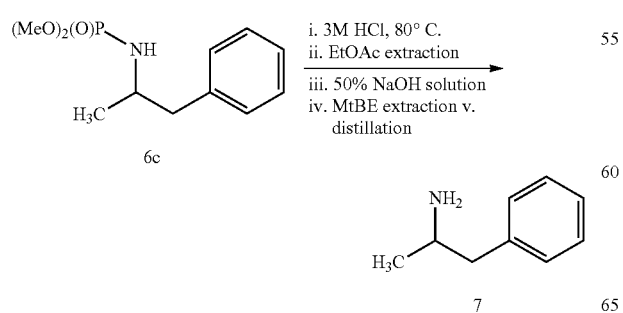

A 50 mL flask is charged with 6c (5.0 g, 20.6 mmol) and 3 M HCl (20.0 mL) and the stirred reaction mixture is heated to 80° C. for 1 hour, at which point HPLC analysis indicates the reaction is complete, and it is cooled to room temperature. The reaction mixture is washed with ethyl acetate (2×20 mL) and the organic extracts are disposed. The aqueous layer is treated with sodium hydroxide solution (50%, 12.0 mL) keeping the internal temperature below 25° C. Methyl tert-butyl ether (15 mL) is added and the reaction mixture is agitated for 15 minutes then allowed to separate. The organic layer is washed with water (10 mL) and organic layer is concentrated under reduced pressure to give 7 as a colorless oil in about 88.0% yield. The expected purity is >99.5% by GC and >99% by HPLC. The expected $^1$H NMR spectra (300 MHz, CDCl$_3$) is δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H) and matches the reference spectra.

Racemic Example 17: Preparation of Amphetamine (7) from 6d

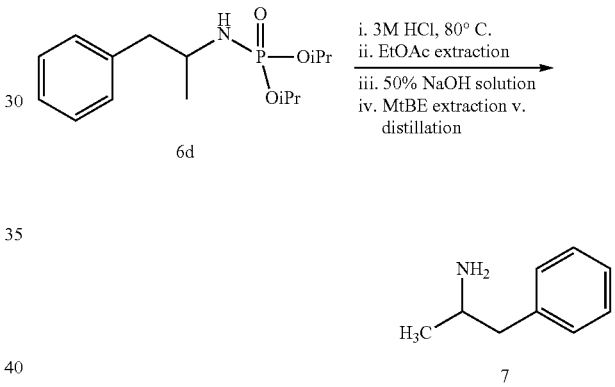

Following the procedure for the preparation of amphetamine (7) from 6a, amphetamine (7) is prepared from diisopropyl (1-phenylpropan-2-yl)phosphoramidate (6d) as a colorless oil. The expected $^1$H NMR spectra (300 MHz, CDCl$_3$) is δ 7.36-7.26 (m, 2H), 7.23-7.13 (m, 3H), 3.26-3.03 (m, 1H), 2.72 (dd, J=13.2, 5.4 Hz, 1H), 2.53 (dd, J=13.2, 8.0 Hz, 1H), 1.20 (br s, 2H), 1.13 (d, J=6.3 Hz, 3H) and matches the reference spectra.

Racemic Example 18: Preparation of Impurities 8a-d

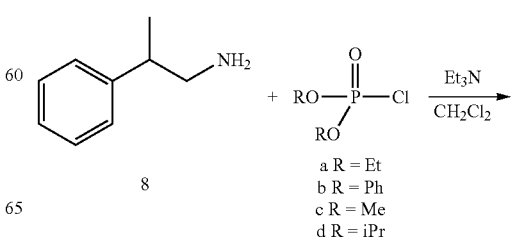

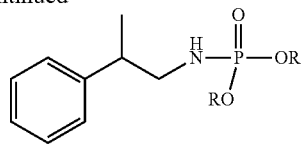

a R = Et
b R = Ph
c R = Me
d R = iPr

A 100 mL 3-neck flask was charged with commercial 8 (1.0 g, 7.4 mmol, from Aldrich Chemical), Et$_3$N (1.23 mL, 8.8 mmol), and dichloromethane (25 mL). The solution was cooled to 0-5° C. and a solution of the appropriate chlorophosphate (8.15 mmol of a through d) in dichloromethane (5 mL) was added over 5 minutes. The reaction mixture was allowed to stir at ambient temperature overnight. The reaction mixture was then quenched by adding water (20 mL) and the organic layer was separated. The organic extract was washed with 1N HCl solution (10 mL), saturated NaHCO$_3$ solution (10 mL), and saturated sodium chloride solution (10 mL). The organic phase was concentrated to dryness to afford the desired product, 8a-d.

8a: 81% yield, colorless oil. 95.8% GC purity. $^1$H NMR (300 MHz, CDCl$_3$) δ 7.30-7.19 (m, 5H), 3.68 (d, J=11.1 Hz, 3H), 3.63 (d, J=11.1 Hz, 3H), 3.20-3.00 (m, 2H), 2.95-2.80 (m, 1H), 2.45 (s, br, 1H), 1.26 (d, J=6.9 Hz, 3H).

8b: 91% yield, colorless oil. 95.16% GC purity. $^1$H NMR (300 MHz, CDCl$_3$) δ 7.26-7.04 (m, 15H), 3.48 (s, br, 1H), 3.35-3.22 (m, 1H), 3.03-2.90 (m, 2H), 1.21 (m, 3H).

8c: 85% yield, colorless oil. 97.47% GC purity $^1$H NMR (300 MHz, CDCl$_3$) δ 7.32-7.19 (m, 5H), 4.04-3.91 (m, 4H), 3.20-3.95 (m, 2H), 2.92-2.80 (m, 1H), 2.45 (s, br, 1H), 1.26 (d, J=6.9 Hz, 3H).

8d: The residue was chromatographed on a 40 g Combiflash Gold column eluting with 100% heptanes to 100% ethyl acetate over a 20-minute gradient. Combined clean fractions we concentrated to dryness to give the desired product as a clear colorless oil in 42% yield, 97.3% purity GC. $^1$H NMR (300 MHz, CDCl$_3$) δ 7.37-7.10 (m, 5H), 4.61-4.44 (m, 2H), 3.20-2.91 (m, 2H), 2.90-2.78 (m, 1H), 2.41-2.28 (m, 1H), 1.35-1.16 (m, 15H).

1) Cates, L. A.; Lawrence, W. H.; McClain, R. J. Journal of Pharmaceutical Sciences, 1966, 55, 1400-1403.

Standard amphetamine processes are known to contain trace amounts of synthetic impurities as a consequence of their method of manufacturing, including potentially genotoxic compounds, metals, and unwanted isomers, enantiomers, regioisomers, and so forth. The process provided herein. by taking an entirely different chemical route, is by definition devoid and free of such standard-process synthetic impurities, metals, and unwanted isomers, enantiomers, regioisomers. Accordingly, in view of impurity-free compositions, the present invention provides an important new generation of dosage forms and compositions.

Dosage Form Examples—Immediate Release

Example 1

The table below lists the ingredients and amount for the formulation of aziridine impurity-free and regioisomer impurity-free amphetamine immediate-release blend used to produce amphetamine immediate-release tablets, 5 mg.

| Ingredients | (%) | mg/Tablet |
|---|---|---|
| impurity-free d-Amphetamine Sulfate | 1.25 | 1.3 |
| impurity-free d,l-Amphetamine Aspartate | 1.25 | 1.3 |
| impurity-free d-Amphetamine Saccharate | 1.25 | 1.3 |
| impurity-free d,l-Amphetamine Sulfate | 1.25 | 1.3 |
| and disintegrate(s), bulking agent(s), glidant (s), lubricants(s), and/or other inactives to total 100% | | |

Example 2

The table below lists the ingredients and amount for the formulation of aziridine impurity-free and regioisomer impurity-free amphetamine immediate-release blend used to produce amphetamine immediate-release tablets, 10 mg.

| Ingredients | (%) | mg/Tablet |
|---|---|---|
| impurity-free d-Amphetamine Sulfate | 1.25 | 2.5 |
| impurity-free d,l-Amphetamine Aspartate | 1.25 | 2.5 |
| impurity-free d-Amphetamine Saccharate | 1.25 | 2.5 |
| impurity-free d,l-Amphetamine Sulfate | 1.25 | 2.5 |
| and disintegrate(s), bulking agent(s), glidant (s), lubricants(s), and/or other inactives to total 100% | | |

Example 3

The table below lists the ingredients and amount for the formulation of aziridine impurity-free and regioisomer impurity-free amphetamine immediate-release blend used to produce amphetamine immediate-release tablets, 20 mg.

| Ingredients | (%) | mg/Tablet |
|---|---|---|
| impurity-free d-Amphetamine Sulfate | 1.25 | 5.0 |
| impurity-free d,l-Amphetamine Aspartate | 1.25 | 5.0 |
| impurity-free d-Amphetamine Saccharate | 1.25 | 5.0 |
| impurity-free d,l-Amphetamine Sulfate | 1.25 | 5.0 |
| and disintegrate(s), bulking agent(s), glidant (s), lubricants(s), and/or other inactives to total 100% | | |

Example 4

The table below lists the ingredients and amount for the formulation of aziridine impurity-free and regioisomer impurity-free amphetamine immediate-release blend. The blend is then compressed on a rotary tablet press to produce amphetamine immediate-release tablets, 30 mg.

| Ingredients | (%) | mg/Tablet |
|---|---|---|
| impurity-free d-Amphetamine Sulfate | 1.25 | 7.5 |
| impurity-free d,l-Amphetamine Aspartate | 1.25 | 7.5 |
| impurity-free d-Amphetamine Saccharate | 1.25 | 7.5 |
| impurity-free d,l-Amphetamine Sulfate | 1.25 | 7.5 |
| and disintegrate(s), bulking agent(s), glidant (s), lubricants(s), and/or other inactives to total 100% | | |

Example 5

The table below lists the ingredients and amount for the formulation of aziridine impurity-free and regioisomer impurity-free amphetamine immediate-release blend. The blend is then filled into hard gelatin capsules using an automatic capsule-filling machine to produce amphetamine immediate-release capsules, 20 mg.

| Ingredients | (%) | mg/Tablet |
|---|---|---|
| impurity-free d-Amphetamine Sulfate | 1.25 | 5.0 |
| impurity-free d,l-Amphetamine Aspartate | 1.25 | 5.0 |
| impurity-free d-Amphetamine Saccharate | 1.25 | 5.0 |
| impurity-free d,l-Amphetamine Sulfate | 1.25 | 5.0 |
| and disintegrate(s), bulking agent(s), glidant (s), lubricants(s), and/or other inactives to total 100% | | |

Example 6

The formulation of this embodiment is prepared using a wet granulation method. The active agent, disintegrant(s), and other excipients are granulated with a granulating fluid, e.g., isopropyl alcohol, ethyl alcohol, and water, in a planetary mixer, high shear mixer or fluidized bed granulator. Binding agents are in granulating fluid or in dry mix. The wet granules are dried in an oven or fluidized-bed dryer, subsequently sieved through a suitable screen to obtain free-flowing granules. The resulting granules are blended with a suitable lubricant and glidant and lubricated granules are compressed into tablets on a rotary press using appropriate tooling. If desired, a coating is applied onto compressed tablets.

The table below lists the ingredients and amount for the formulation of aziridine impurity-free and regioisomer impurity-free amphetamine immediate-release granulates. The blend is compressed on a rotary tablet press to produce amphetamine immediate-release tablets, 30 mg.

| Ingredients | (%) | mg/Tablet |
|---|---|---|
| impurity-free d-Amphetamine Sulfate | 1.25 | 7.5 |
| impurity-free d,l-Amphetamine Aspartate | 1.25 | 7.5 |
| impurity-free d-Amphetamine Saccharate | 1.25 | 7.5 |
| impurity-free d,l-Amphetamine Sulfate | 1.25 | 7.5 |
| and disintegrate(s), bulking agent(s), glidant (s), lubricants(s), and/or other inactives to total 100% | | |

Dosage Form Examples—Sustained Release Formulations for Aziridine Impurity-Free and Regioisomer Impurity-Free Amphetamine Compositions

Example 7

| impurity-free mixed amphetamine salts loaded beads (MASL) | 500 grams |
|---|---|
| Ethyl cellulose (Ethocel N-10, Dow Chemical) | 15.46 grams |
| Ethyl acetate | 515 grams |

Ethyl cellulose (15.46 gram) is dissolved in 515 grams of ethyl acetate. Into a Wurster column is charged 500 grams of MASL beads which are then coated with the coating mixture under conditions of 40° C., spray pressure 1 bar, and spray rate of 10 grams/min. The line is rinsed with ethyl acetate and the pellets are dried for approximately twenty minutes and recovered to give a product of 97% by weight MASL beads and 3% by weight ethyl cellulose coating.

Example 8

| impurity-free mixed amphetamine salts loaded beads | 500 grams |
|---|---|
| Ethyl cellulose (Ethocel N-10, Dow Chemical) | 37.78 grams |
| Hydroxypropyl cellulose (Klucel LF, Aqualon) | 8.70 grams |
| Methylene chloride | 744 grams |
| Methanol | 186 grams |

Ethyl cellulose (37.78 grams) and hydroxypropyl cellulose (8.70 grams) are dissolved in a mixture of methylene chloride and methanol (4:1). Into a Wurster column is charged 500 grams of MASL beads which are then coated with the coating mixture under conditions of 40° C., spray pressure 1 bar, and spray rate 10 grams/min. The line is rinsed with methanol and the pellets are dried for approximately twenty minutes and recovered to give a product of 92% by weight MASL beads and 8% by weight ethyl cellulose/hydroxypropyl cellulose coating.

Example 9

| impurity-free mixed amphetamine salts loaded beads | 500 grams |
|---|---|
| Surelease (Ethyl cellulose-based dispersion, Colorcon) | 173.92 grams |
| Water | 43.48 grams |

Surelease (173.92 grams) is diluted with 43.48 grams of water. Into a Wurster column (Versa-Glatt. Glatt Air Techniques) is charged 500 grams of MASL beads which are then coated with the coating mixture under conditions of 60° C. inlet temperature, spray pressure 1 bar, and spray rate 6 grams/min. The line is rinsed with water and the pellets are dried for approximately twenty minutes and recovered to give a product of 92% by weight MASL beads and 8% by weight ethyl cellulose coating.

Example 10

| impurity-free mixed amphetamine salts loaded beads | 500 grams |
|---|---|
| Eudragit RS30D | 111.49 grams |
| Triethyl citrate | 10.03 grams |
| Water | 115.94 grams |

Triethyl citrate is mixed into Eudragit RS30D for 30 min. The plasticized Eudragit RS30D is diluted with water and filtered through a 60-mesh screen. Into a Wurster column is charged 500 grams of MASL beads which are then coated with the coating mixture under conditions of 40° C. inlet temperature, spray pressure 1 bar, and spray rate 6 grams/min. The line is rinsed with ethyl acetate and the pellets are dried for approximately twenty minutes and recovered to give a product of 92% by weight MASL beads and 8% by weight Eudragit RS30D coating.

Example 11

| | |
|---|---|
| impurity-free mixed amphetamine salts loaded beads | 500 grams |
| impurity-free mixed amphetamine salts | 48.5 grams |
| Glyceryl behenate (Compritol 888, Gattefosse) | 436.5 grams |

Mixed amphetamine salts are dispersed in the molten glyceryl behenate. The drug-containing hot melt is sprayed onto the mixed amphetamine salts loaded beads in a Wurster column under conditions of 30° C. inlet temperature, spray pressure 2 bar, and a spray rate of 10 grams/min.

Example 12

| | |
|---|---|
| impurity-free mixed amphetamine salts loaded beads | 500 grams |
| Eudragit L100 | 25.25 grams |
| Ethyl cellulose (Ethocel N-10, Dow Chemical) | 25.25 grams |
| Triethyl citrate | 5.05 grams |
| Acetone | 833.4 grams |
| Methanol | 277.8 grams |

Eudragit L100 and ethyl cellulose are dissolved in the mixture of acetone and methanol. Subsequently, methyl citrate is added to the polymer solution. Into the Wurster column is charged 500 grams of MASL beads which are then coated with the coating mixture under conditions of 40° C., spray pressure 1 bar, and spray rate 10 grams/min. The line is rinsed with methanol and the pellets are dried for approximately twenty minutes and recovered to give a product of 90% by weight MASL beads and 10% by weight ethyl cellulose Eudragit L100 coating.

SR Matrix Beads/Tablets

Example 13

| | |
|---|---|
| impurity-free Amphetamine Aspartate | 50 grams |
| impurity-free Amphetamine Sulfate | 50 grams |
| impurity-free Dextroamphetamine saccharate | 50 grams |
| impurity-free Dextroamphetamine sulfate | 50 grams |
| Microcrystalline cellulose | 400 grams |
| Poly(ethylene oxide), Polyox WSR 303 | 1380 grams |
| Magnesium stearate | 20 grams |

All the impurity-free amphetamine salts, microcrystalline cellulose, and poly(ethylene oxide) are sieved through a 60 mesh screen and loaded into a V-shaped blender with an intensifier bar. The powder mixture is blended for 15 min, with the intensifier bar on for 3 min. at the middle of the blending process. The powder blend is unloaded and screened through a 60 mesh sieve. The screened powder blend is lubricated with magnesium stearate in the V-shaped blender for 3 min. The lubricated powder blend is compacted in a roller compactor to form granules.

Example 14

| | |
|---|---|
| impurity-free Amphetamine Aspartate | 50 grams |
| impurity-free Amphetamine Sulfate | 50 grams |
| impurity-free Dextroamphetamine saccharate | 50 grams |
| impurity-free Dextroamphetamine sulfate | 50 grams |
| Microcrystalline cellulose | 1780 grams |
| Magnesium stearate | 20 grams |

All the impurity-free amphetamine salts and microcrystalline cellulose are sieved through a 60 mesh screen and loaded into a V-shaped blender with an intensifier bar. The powder mixture is blended for 15 min, with the intensifier bar on for 3 min, at the middle of the blending process. The powder blend is unloaded and screened through a 60 mesh sieve. The screened powder blend is lubricated with magnesium stearate in the V-shaped blender for 3 min. The lubricated powder blend is compressed into tablets using 3/32" tooling.

Example 15

| | |
|---|---|
| Mini-tablets | 500 grams |
| Surelease | 127.7 grams |
| water | 85.1 grams |

Surelease (127.7 grams) is diluted with 85.1 grams of water. Into the Wurster column (Versa-Glatt, Glatt Air Techniques) is charged 500 grams of the mini-tablets which are then coated with the coating mixture under conditions of 60 C. inlet temperature, spray pressure 1 bar, and spray rate 6 grams/min. The line is rinsed with water and the pellets are dried for approximately twenty minutes and recovered to give a product of 94% by weight MASL minitablets and 6% by weight ethyl cellulose coating.

Example 16

| | |
|---|---|
| impurity-free mixed amphetamine salts loaded beads | 500 grams |
| Surelease (Ethyl cellulose-based dispersion, Colorcon) | 272.7 grams |
| Water | 68.2 grams |

Surelease (272.7 grams) is diluted with 68.2 grams of water. Into Wurster column (Versa-Glatt, Glatt Air Techniques) is charged 500 grams of MASL beads which are then coated with the coating mixture under conditions of 60 degree C. inlet temperature, spray pressure 1 bar, and spray rate 6 grams/min. The line is rinsed with water and the pellets are dried for approximately twenty minutes and recovered to give a product of 88% by weight MASL beads and 12% by weight ethyl cellulose coating.

The dissolution data for 8% and 12% coating levels are estimated as follows:

| | 1 hour | 2 hours | 4 hours | 6 hours | 8 hours |
|---|---|---|---|---|---|
| 8% coating | 45% | 74% | 93% | 98% | 100% |
| 12% coating | 25% | 47% | 70% | 81% | 87% |

Examples—Abuse Deterrent

General Synthesis of amino acid-amphetamine Conjugates

Amino acid conjugates were synthesized by the known general method described in U.S. Pat. No. 7,223,735 and elsewhere.

Example 17

Synthesis of Aziridine-Free and Regioisomer Impurity Free L-Lysine-d-Amphetamine L-lysine-d-amphetamine was synthesized by (a) Coupling, followed by (b) Deprotection.

(A) Coupling

| Reagents | MW | Weight | mmoles | Equivalents |
| --- | --- | --- | --- | --- |
| impurity-free d-amphetamine freebase | 135.2 | 4.75 g | 35.13 | 1 |
| Boc-Lys(Boc)-OSu | 443.5 | 15.58 g | 35.13 | 1 |
| Di-iPr-Et-Amine | 129 | 906 mg | 7.03 | 0.2, |
| 1,4-Dioxane | — | 100 mL | — | — |

To a solution of Boc-Lys(Boc)-OSu (15.58 g, 35.13 mmol) in dioxane (100 mL) under an inert atmosphere is added impurity-free d-amphetamine freebase (4.75 g, 35.13 mmol) and DiPEA (0.9 g, 1.22 mL, 7.03 mmol). The resulting mixture is allowed to stir at room temperature overnight. Solvent and excess base is then removed using reduced pressure evaporation. The crude product is dissolved in ethyl acetate and loaded on to a flash column (7 cm wide, filled to 24 cm with silica) and eluted with ethyl acetate. The product is isolated; the solvent is reduced by rotary evaporation and the purified protected amide is dried by high-vac to obtain a white solid.

b. Deprotection

| Reagents | MW | Weight | mmoles | Equivalents |
| --- | --- | --- | --- | --- |
| 4M HCl in dioxane | 4 mmol/mL | 50 mL | 200 | 6.25 |
| Boc-Lys(Boc)-Amp | 463.6 | 14.84 g | 32 | 1 |
| 1,4-Dioxane | — | 50 mL | — | — |

The protected amide is dissolved in 50 mL of anhydrous dioxane and stirred while 50 mL (200 mmol) of 4M HCl/dioxane is added and stirred at room temperature overnight. The solvents are then reduced by rotary evaporation to afford a viscous oil. Addition of 100 mL MeOH followed by rotary evaporation results in a golden colored solid material that is further dried by storage at room temperature under high vacuum.

Example 18 Synthesis of Impurity-Free Ser-Amp

Ser-Amp is synthesized by a similar method except the amino acid starting material is Boc-Ser(O-tBu)-OSu and the deprotection is done using a solution of trifluoroacetic acid instead of HCl.

Example 19 Synthesis of Impurity-Free Phe-Amp

Phe-Amp is synthesized by a similar method except the amino acid starting material is Boc-Phe-OSu.

Example 20 Synthesis of Impurity-Free Gly3-Amp

Gly3-Amp is synthesized by a similar method except the amino acid starting material is Boc-GGG-OSu.

Example 21 Synthesis of Impurity-Free Gly2-Amp

Gly2-Amp is synthesized by a similar method except the amino acid starting material is Boc-Gly-Gly-OSu.

Example 22 Synthesis of Impurity-Free Glu2-Phe-Amp

Glu2-Phe-Amp is synthesized by a similar method except the amino acid starting material is Boc-Glu(OtBu)-Glu(OtBu)-OSu and the starting drug conjugate is Phe-Amp (see Phe-Amp synthesis).

Example 23 Synthesis of Impurity-Free His-Amp

His-Amp is synthesized by a similar method except the amino acid starting material is Boc-His(Trt)-OSu.

Example 24 Synthesis of Impurity-Free Lys-Gly-Amp

Lys-Gly-Amp is synthesized by a similar method except the amino acid starting material is Boc-Lys(Boc)-OSu and the starting drug conjugate is Gly-Amp (see Gly-Amp synthesis).

Example 25 Synthesis of Impurity-Free Lys-Glu-Amp

Lys-Glu-Amp is synthesized by a similar method except the amino acid starting material is Boc-Lys(Boc)-OSu and the starting drug conjugate is Glu-Amp.

Example 26 Synthesis of Impurity-Free Glu-Amp

Glu-Amp is synthesized by a similar method except the amino acid starting material is Boc-Glu(OtBu)-OSu.

Example 27 Synthesis of Impurity-Free (d)-Lys-(l)-Lys-Amp (d)-Lys-(l)-Lys-Amp is synthesized by a similar method except the amino acid starting material is Boc-(d)-Lys(Boc)-(l)-Lys(Boc)-OSu.

Example 28 Synthesis of Impurity-Free Gulonic Acid-Amp

Gul-Amp is synthesized by a similar method except the carbohydrate starting material is gulonic acid-OSu.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

The invention claimed is:

1. A process for preparing a drug substance comprising the steps of:
   (i) providing a substituted amphetamine or a pharmaceutically acceptable salt, solvate, or mixture of two or more thereof, as an active pharmaceutical ingredient, wherein the substituted amphetamine comprises not more than 0.1% by weight of amphetamine-process related impurity,
   wherein the substituted amphetamine is produced by a process that comprises the steps of performing a stereospecific cuprate addition reaction upon an aziridine phosphoramidate compound to obtain a aryl or aryl-alkyl phosphoramidate amphetamine precursor, and deprotecting the aryl or aryl-alkyl phosphoramidate amphetamine precursor under acidic conditions effective to produce a substituted amphetamine,
   wherein the substituted amphetamine is selected from the group consisting of: dex-amphetamine, dex-N-methylamphetamine, and dex-N-ethylamphetamine, and a racemic mixture of amphetamine isomers, wherein the dex-amphetamine, dex-N-methylamphetamine, dex-N-ethylamphetamine, and racemic mixture of amphetamine isomers is made according to the process comprising the steps 1a and 2a:
   (1a) providing a compound of Formula 5:

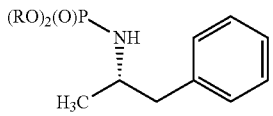

wherein R is alkyl or aryl; and
   (2a) deprotecting the compound of Formula 5 under acidic conditions effective to produce (2S)-1-phenylpropan-2-amine of Formula I:

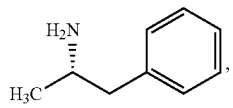

and wherein the racemic mixture of amphetamine isomers is made according to the process comprising the steps 1b and 2b:
   (1b) providing a compound of Formula 6:

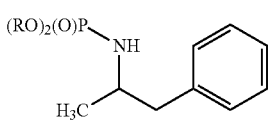

wherein R is alkyl or aryl; and
   (2b) deprotecting the compound of Formula 6 under acidic conditions effective to produce a racemic mixture of amphetamine isomers of Formula 7:

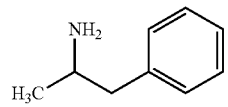

further comprising the step of formulating the drug substance with one or more excipients to produce a pharmaceutical composition
   wherein the regioisomeric purity of Formula 5 is >99% and the regioisomer is <0.1%.

2. The process according to claim 1, wherein the amphetamine-process related impurity is 2-methyl-3-phenyl-aziridine.

3. The process according to claim 1, further comprising the steps:
   using the process to obtain a dextroamphetamine and reacting dextroamphetamine with sulfuric acid under conditions to obtain dextroamphetamine sulfate;
   using the process to obtain amphetamine and reacting amphetamine with sulfuric acid under conditions to obtain amphetamine sulfate;
   using the process to obtain amphetamine and reacting amphetamine with aspartic acid under conditions to obtain amphetamine aspartate monohydrate;
   using the process to obtain dextroamphetamine and reacting dextroamphetamine with saccharic acid under conditions to obtain dextroamphetamine saccharate; and
   combining as a mixture
   equal parts amphetamine aspartate monohydrate (25%), amphetamine sulfate (25%), dextroamphetamine saccharate (25%), and dextroamphetamine sulfate (25%).

4. The process according to claim 1, wherein the substituted amphetamine is (2S)-1-phenylpropan-2-amine.

5. The process according to claim 1, wherein the pharmaceutical composition is a tablet formulated to orally administer at least about 5 mg of the active pharmaceutical ingredient, or the molar equivalent amount of a salt thereof.

6. The process according to claim 1, wherein the pharmaceutical composition is a tablet formulated to orally administer between about 1 mg and about 100 mg of the active pharmaceutical ingredient, or the molar equivalent amount of a salt thereof.

7. The process according to claim 1, wherein the amphetamine process-related impurity comprises drug substance prepared according to the process of claim 1, further comprising not more than about 1000 ppm of the amphetamine process-related impurity.

8. The process according to claim 1, wherein the amphetamine process-related impurity comprises not more than about 500 ppm of the substituted amphetamine.

9. The process according to claim 1, wherein the amphetamine process-related impurity comprises a residual solvent in an amount of not more than about 0.3%, by weight, diethyl ether, tetrahydrofuran or 2-methyltetrahydrofuran.

10. The process according to claim 1, wherein the amphetamine process-related impurity comprises a residual metal selected from a copper impurity, a magnesium impurity, and a mixture thereof, in an amount of not more than about 20 ppm.

11. The process according to claim 1, wherein the pharmaceutical composition is a unit dosage form comprising 55-90%, by weight, of the drug substance prepared according to the process of claim 1 and 10-45% total, by weight, of one or more excipients, wherein said unit dosage form contains at least about 5 mg of the active pharmaceutical ingredient, or the molar equivalent amount of a salt thereof.

12. The process according to claim 1, wherein the substituted amphetamine is selected from the group consisting of: dex-amphetamine, dex-N-methylamphetamine, and dex-N-ethylamphetamine, and a racemic mixture of amphetamine isomers, wherein the dex-amphetamine, dex-N-methylamphetamine, dex-N-ethylamphetamine, and racemic mixture of amphetamine isomers is made according to the process comprising the steps 1a and 2a:

(1a) providing a compound of Formula 5:

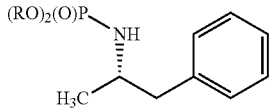

wherein R is alkyl or aryl; and (2a) deprotecting the compound of Formula 5 under acidic conditions effective to produce (2S)-1-phenyl-propan-2-amine of Formula I:

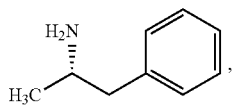

and wherein the racemic mixture of amphetamine isomers is made according to the process comprising the steps 1b and 2b:

(1b) providing a compound of Formula 6:

6

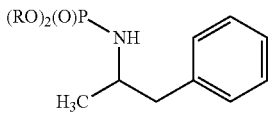

wherein R is alkyl or aryl; and (2b) deprotecting the compound of Formula 6 under acidic conditions effective to produce a racemic mixture of amphetamine isomers of Formula 7:

7

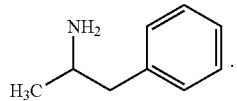

13. The process according to claim 12, wherein the racemic mixture of amphetamine isomers is comprised of equal parts amphetamine aspartate monohydrate (25%), amphetamine sulfate (25%), dextroamphetamine saccharate (25%), and dextroamphetamine sulfate (25%).

14. The process according to claim 12, wherein the racemic mixture of amphetamine isomers is comprised of equal parts amphetamine aspartate hemihydrate (25%), amphetamine sulfate (25%), dextroamphetamine saccharate (25%), and dextroamphetamine sulfate (25%).

15. The process according to claim 1, wherein the acidic conditions of step 2a or 2b are aqueous hydrochloric, sulfuric or phosphoric acids.

16. The process according to claim 1, wherein the acidic conditions of step 2a or 2b are aqueous hydrochloric, sulfuric or phosphoric acids and wherein the aqueous acid water content is in an amount of 50% to 90%.

17. The process according to claim 1, wherein R in step 1a or 1b is R=methyl, ethyl, isopropyl or phenyl.

18. The process according to claim 1, wherein the step 1a of providing a compound of Formula 5 comprises the steps of:

Step (1)(a)(1) providing a compound of Formula 4:

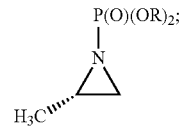

wherein R is alkyl or aryl and

Step (1)(a)(2) reacting the compound of Formula 4 with phenylmagnesium halide and a copper halide catalyst under solvent and temperature conditions effective to produce a compound of Formula 5 in a purity substantially free of any regioisomeric impurities.

19. The process according to claim 18 wherein R in Step (1)(a)(1) is R=methyl, ethyl, isopropyl or phenyl.

20. The process according to claim 18 wherein the copper halide catalyst in Step (1)(a)(2) is CuCl, CuCl2, CuBr, CuF, Cu(OAc)2, Cu(acac)2, Cu(Ome)2, copper nanoparticles, copper turnings, copper grit, copper powder, copper shot, copper foil, copper flake, copper disk, copper precipitate, copper mist, copper dust, copper granules, and copper slug.

21. The process according to claim 18 wherein the solvent in Step (1)(a)(2) is selected from the group consisting of an organic ether, a solvent that contains an organic ether, tetrahydrofuran, tetrahydrofuran mixed with 2-methyltetrahydrofuran, tetrahydrofuran mixed with methyl tert-butyl ether, and tetrahydrofuran mixed with toluene.

22. The process according to claim 18 wherein the temperature in Step (1)(a) (2) is a temperature of from about −10° C. to about 70° C.

23. The process of claim 18, wherein said providing a compound of Formula 4 comprises the steps:

Step (1)(a)(1)(a)—providing a compound of Formula 3:

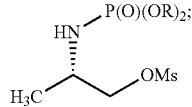

wherein R is alkyl or aryl; and

Step (1)(a)(1)(b)—reacting the compound of Formula 3 with the base under conditions effective to produce a compound of Formula 4.

24. The process according to claim 23 wherein the R in Step (1)(a)(1)(a) is R=methyl, ethyl, isopropyl or phenyl.

25. The process according to claim 23, wherein the base in Step (1)(a)(1)(b) is potassium hydroxide or potassium carbonate.

26. The process according to claim 23 wherein the Step (1)(a)(1)(a) of providing a compound of Formula 3 comprises the steps of:

Step (1)(a)(1)(a)(1)—providing a compound of Formula 2:

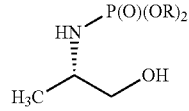

wherein R is alkyl or aryl; and

Step (1)(a)(1)(a)(2)—reacting the compound of Formula 2 with methanesulfonyl chloride and a base under conditions effective to produce a compound of Formula 3.

27. The process according to claim 26 wherein the R in Step 1a1a1 is R=methyl, ethyl, isopropyl or phenyl.

28. The process according to claim 26 wherein said providing a compound of Formula 2 comprises the steps:

Step (1)(a)(1)(a)(1)(a) providing a compound of Formula 1:

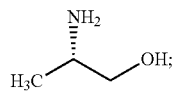

and

Step (1)(a)(1)(a)(1)(b) reacting the compound of Formula II with the appropriate

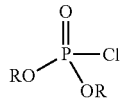

wherein R=alkyl or aryl under conditions effective to produce a compound of Formula 2.

29. The process according to claim 28 wherein the R in Step (1)(a)(1)(a)(1)(b) is R=methyl, ethyl, isopropyl or phenyl.

30. The process according to claim 26 wherein the acidic conditions are aqueous hydrochloric, sulfuric or phosphoric acids.

31. The process according to claim 18, wherein the amphetamine-process related impurity is 2-methyl-3-phenyl-aziridine.

32. The process according to claim 1, wherein the active pharmaceutical ingredient is selected from the group consisting of: (S)-dimethyl (1-phenylpropan-2-yl)phosphoramidate (5a); (S)-diethyl (1-phenylpropan-2-yl)phosphoramidate (5b); (S)-diisopropyl (1-phenylpropan-2-yl) phosphoramidate (5c); (S)-diphenyl (1-phenylpropan-2-yl) phosphoramidate (5d); diethyl (1-phenylpropan-2-yl) phosphoramidate (6a); diphenyl (1-phenylpropan-2-yl) phosphoramidate (6b); dimethyl (1-phenylpropan-2-yl) phosphoramidate (6c); and diisopropyl (1-phenylpropan-2-yl)phosphoramidate (6d).

* * * * *